US012286400B2

(12) United States Patent
Reisch et al.

(10) Patent No.: US 12,286,400 B2
(45) Date of Patent: Apr. 29, 2025

(54) ISOFAGOMINE SALTS, METHODS OF USE AND FORMULATIONS

(71) Applicant: TAKEDA PHARMACEUTICAL COMPANY LIMITED, Osaka (JP)

(72) Inventors: Helge Reisch, Westerly, RI (US); Jeffrey Scott Depue, Windham, NH (US); Fritz Blatter, Reinach BL (CH); Jennifer Robin, Waldighoffen (FR); Michael Peter Hahn, Lexington, MA (US); Gaozhong Zhu, Weston, MA (US); Muthuraman Meiyappan, Lexington, MA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 728 days.

(21) Appl. No.: 17/605,979

(22) PCT Filed: Apr. 24, 2020

(86) PCT No.: PCT/US2020/029810
§ 371 (c)(1),
(2) Date: Oct. 22, 2021

(87) PCT Pub. No.: WO2020/219874
PCT Pub. Date: Oct. 29, 2020

(65) Prior Publication Data
US 2023/0110129 A1    Apr. 13, 2023

Related U.S. Application Data

(60) Provisional application No. 62/838,445, filed on Apr. 25, 2019.

(51) Int. Cl.
C07D 211/46    (2006.01)
A61K 31/445   (2006.01)
A61K 45/06    (2006.01)
A61P 3/00     (2006.01)
C07D 211/42   (2006.01)

(52) U.S. Cl.
CPC ........... C07D 211/42 (2013.01); A61K 45/06 (2013.01); C07B 2200/13 (2013.01)

(58) Field of Classification Search
CPC ....... C07D 211/46; A61K 31/445; A61P 3/11; A61P 3/00
See application file for complete search history.

(56) References Cited

U.S. PATENT DOCUMENTS

| 5,844,102 A | 12/1998 | Sierks et al. |
| 2007/0281975 A1 | 12/2007 | Mugrage et al. |
| 2011/0027254 A1 | 2/2011 | Daniel et al. |

FOREIGN PATENT DOCUMENTS

| CA | 2763464 A1 | 12/2010 |
| EP | 2444102 | 8/2015 |
| WO | 95/24391 A1 | 9/1995 |
| WO | 2007/150064 A2 | 12/2007 |
| WO | 2007140212 A2 | 12/2007 |
| WO | 2007140212 A3 | 12/2007 |
| WO | 2012071451 A2 | 5/2012 |
| WO | 2012071451 A3 | 5/2012 |
| WO | 2013/130963 A1 | 9/2013 |
| WO | 2019084309 | 5/2019 |

OTHER PUBLICATIONS

International Search Report mailed Jul. 1, 2020 in connection with PCT/US20/029810.
Written Opinion mailed Jul. 1, 2020 in connection with PCT/US20/029810.
Elstein, et al. Oral maintenance clinical trial with miglustat for type I Gaucher disease: switch from or combincation with intravenous enzyme replacement, Blood, vol. 110, No. 7, Oct. 1, 2007, pp. 2296-2301.
European Search Report issued Dec. 7, 2022 in connection with EP Application No. 20795852.
Office Action issued in JP Application No. 2021-562868 dated May 28, 2024.
K. Ashizawa, et al., Polymorphic Phenomena of Pharmaceuticals and the Science of Crystallization, Maruzen Planet, Sep. 20, 2002, pp. 305-317.
H. Nagase, Latest Drug Discovery Chemistry (The Practice of Medicinal Chemistry), vol. 2, Technomic Corporation, 1999, pp. 347-354.
R. Hirayama, Handbook of Organic Compound Crystal Preparation—Principles and Know-How-, 2008, pp. 36-43.
K. Ashizawa, Optimization of salt and crystal forms and crystallization techniques, Pharm Tech Japan, 2002, vol. 18, No. 10, pp. 81-96.

*Primary Examiner* — Bruck Kifle
(74) *Attorney, Agent, or Firm* — Troutman Pepper Locke LLP

(57) ABSTRACT

The present invention relates generally to the field of pharmaceuticals, and specifically relates to isofagomine (IFG), novel salts thereof and preparation methods and uses of these, for example, in formulating pharmaceutical compositions for the treatment of Gaucher disease. Also provided are novel crystalline forms of isofagomine salts, methods for preparing the crystalline forms, and their use in formulating pharmaceutical compositions.

18 Claims, 31 Drawing Sheets

FIG. 22

ISOFAGOMINE SALTS, METHODS OF USE AND FORMULATIONS

CROSS-REFERENCE TO RELATED APPLICATIONS

This application is a 371 National Stage of International PCT/US20/29810, filed Apr. 24, 2020, which claims priority to U.S. Provisional Patent Application No. 62/838,445, filed on Apr. 25, 2019, the entire contents of which are incorporated herein by reference.

FIELD OF THE INVENTION

The present invention relates to isofagomine, pharmaceutically acceptable isofagomine salts, pharmaceutical compositions comprising them, and to their use in formulating compositions for treatment of Gaucher disease.

BACKGROUND OF THE INVENTION

Gaucher disease is an autosomal recessive disorder caused by mutations in the GBA gene, which results in a deficiency of the lysosomal enzyme β-glucocerebrosidase (alternatively GCase). GCase hydrolyzes the glycolipid glucocerebroside formed after degradation of glycosphingolipids in the membranes of white blood cells and red blood cells.

This accumulation causes a range of clinical manifestations including splenomegaly, hepatomegaly, skeletal disorder, thrombocytopenia and anemia. (Beutler et al. "Gaucher disease" *The Metabolic and Molecular Bases of Inherited Disease*. McGraw-Hill, Inc., New York, 1995, pp. 2625-2639.) In Gaucher disease, various forms of mutant GCase have reduced, little, or no glucosylceramide cleavage activity, depending upon the mutated amino acid or amino acids. The severity of this disorder is correlated with relative levels of residual enzyme activity and the resulting extent of accumulation of the substrate.

It was found that specific GCase enzyme inhibitors could bind with specificity to the enzyme during its synthesis, stabilizing protein folding in the ER, and would subsequently dissociate from the enzyme at its native location in the lysosome, thereby increasing enzyme activity by increasing the level of enzyme that is processed instead of degraded. Isofagomine, (3R,4R,5R)-3,4-dihydroxy-5-hydroxymethylpiperidine, also known as IFG, is such a GCase enzyme inhibitor that binds in the active site of both wildtype and mutant GCase and stabilizes the enzyme during synthesis and processing and has been shown to be effective at increasing the activity of mutant forms of GCase. In the absence of the "pharmacological chaperone," the mutated enzyme protein misfolds in the ER, is retarded in its maturation to a final product and is subsequently degraded by the ER-associated degradation mechanism. In vitro, IFG was shown to increase the activity of mutant GCase in fibroblasts from Gaucher patients. Synthesis of this compound is described in U.S. Pat. No. 5,844,102 to Sierks et al. and U.S. Pat. No. 5,863,903 to Lundgren et al.

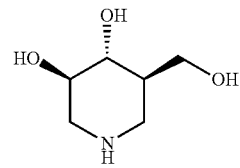

IFG
Isofagomine
(3R, 4R, 5R)-3,4-dihydroxy-5-hydroxymethyl-piperidine

IFG has also been shown to increase the stability of GCase pharmaceutical formulations such as VPRIV® (a formulation of velaglucerase alfa used to treat Gaucher disease). The combination of IFG, e.g., as an isofagomine salt, with GCase in liquid compositions, where the high protein concentration may contribute to aggregation, has been shown to improve the stability of GCase in vitro. In particular, liquid compositions with a molar ratio of at least 1:2.5 (GCase:IFG) have substantially less GCase aggregation and degradation and provide a formulation with higher GCase activity. See, PCT/US18/57575, the contents of which are incorporated herein by reference.

The physicochemical properties of a pharmaceutical ingredient can be improved by selecting an appropriate salt form. Further, a single pharmaceutical ingredient or a salt thereof, may exist in a plurality of crystalline, i.e., polymorphic, forms including hydrates and solvates thereof. In this regard, alternative forms of pharmaceutical ingredient may have widely different properties such as, for example, enhanced thermodynamic stability, higher purity or improved bioavailability (e.g. better absorption, dissolution patterns). Specific compound forms could also facilitate the manufacturing (e.g. enhanced flowability), handling and storage (e.g. non-hygroscopic, long shelf life) of the compound formulations or allow the use of a lower dose of the therapeutic agent, thus decreasing its potential side effects and ensuring the equivalence of the pharmaceutical ingredient batch to batch. Thus, it is important to provide novel forms, including salts and polymorphs thereof, of a pharmaceutical ingredient thereby providing the potential for improved properties for manufacturing, formulating, storage and pharmaceutical use.

To carry out the pharmaceutical development of IFG and to realize its potential, there is a need in the art for additional forms of IFG, including various salts and polymorphic forms thereof, that will facilitate the preparation of improved formulations of this pharmaceutical ingredient for its use as an active pharmaceutical ingredient or its use as a stabilizing agent for GCase in formulations. There remains a need for additional salt and crystalline polymorphic forms that can provide a greater range of solubility, stability and physical properties that facilitate storage, subsequent processing and improvement of the bioavailability of GCase.

SUMMARY OF THE INVENTION

After extensive research on different solid forms of isofagomine, it is surprisingly found and demonstrated that some of its salts, including crystalline, hydrate and/or solvate forms thereof, provide advantageous production, handling, storage, stability, solubility and/or therapeutic properties.

Thus, in one aspect the present disclosure relates to an isofagomine salt, and crystalline, hydrate or solvate forms thereof, wherein the isofagomine salt is prepared from an organic acid. In a further embodiment, the isofagomine salt is selected from isofagomine quinate, isofagomine malate, isofagomine fumarate, isofagomine oxalate, isofagomine malonate, isofagomine succinate, isofagomine D-tartrate, isofagomine cyclamate and isofagomine ascorbate. In another embodiment the isofagomine salt is in a crystalline form. In a further embodiment, the crystalline isofagomine salt is selected from isofagomine quinate, isofagomine fumarate, isofagomine oxalate, isofagomine D-tartrate. Optionally, the crystalline form of isofagomine is characterized by three or more very strong, strong and medium intensity XRPD peaks listed in Tables 1, 3, 5, and 7, respectively.

In a further aspect, the present disclosure relates to a crystalline form of isofagomine quinate characterized by the x-ray diffraction pattern having one or more characteristic peaks at 2theta values of 9.5°±0.2°, 15.0°±0.2°, 17.4°±0.2°, 18.1°±0.2°, 20.3°±0.2°, 23.8°±0.2°, 24.8°±0.2° and 25.4°±0.2°.

In a further aspect, the present disclosure relates to a crystalline form of isofagomine fumarate characterized by the x-ray diffraction pattern having one or more characteristic peaks at 2theta values of 16.1°±0.2°, 18.3°±0.2°, 18.6°±0.2°, 21.9°±0.2°, 23.6°±0.2°, 23.8°±0.2°, and 25.5°±0.2°.

In a further aspect, the present disclosure relates to a crystalline form of isofagomine oxalate characterized by the x-ray diffraction pattern having one or more characteristic peaks at 2theta values of 27.8°, ±0.2°, 32.2°, ±0.2°, 35.3°, ±0.2°, 36.6°, ±0.2°, 37.4°, ±0.2°, 38.4°, ±0.2°, 18.5°±0.2°, 19.2°±0.2°, 21.4°±0.2°, 22.6°±0.2°, 24.5°±0.2°, 24.8°±0.2°, 26.8°±0.2°, 20.2°±0.2° and 23.7°±0.2°.

In a further aspect, the present disclosure relates to a crystalline form of isofagomine D-tartrate characterized by the x-ray diffraction pattern having one or more characteristic peaks at 2theta values of 9.8°, ±0.2°, 10.5°, ±0.2°, 15°, ±0.2°, 15.3°, ±0.2°, 15.8°, ±0.2°, 17.4°, ±0.2°, 17.9°±0.2°, 18.5°±0.2°, 18.9°±0.2°, 19.6°±0.2°, 21.1°±0.2°, 21.7°±0.2°, 22°±0.2°, 24.2°±0.2°, 24.8°±0.2°, 26.6°±0.2°, 27.1°±0.2°, 27.4°±0.2°, 33.8°±0.2°, 35.7°±0.2°, 36.5θ±0.2θ and 37.5°±0.2°.

An additional aspect of the present disclosure includes pharmaceutical compositions comprising isofagomine (IFG) and at least one pharmaceutically acceptable carrier. In some embodiments of the pharmaceutical compositions of the present disclosure, IFG is a stabilizing agent for a GCase active ingredient. In certain embodiments, IFG is in a free base or salt form (including crystalline, hydrate and solvate forms thereof). In another aspect, isofagomine is present in an amount sufficient to reduce degradation of the GCase active ingredient; the amount may be considerably less than the therapeutically effective amount of IFG alone or when IFG is administered in a therapeutically effective amount in combination with the GCase active ingredient in conventional combination therapy. In some embodiments, the composition comprises 60-180 mg/mL of a glucocerebrosidase (GCase). In some embodiments, the GCase is velaglucerase alfa. In a further aspect is provided a composition comprising a GCase and IFG in a molar ratio of at least about 1:>2.5 (i.e., 1:x, where x is greater than 2.5), about 1:3 or about 1:2.5 to about 1:3.5. In additional embodiments, the composition further comprises a sodium citrate buffer, sucrose and a surfactant selected from PS20, PS80 or poloxamer 188. In additional embodiments of pharmaceutical compositions, the isofagomine salt is at least 95% pure.

In another aspect of the disclosure is provided a method of preparing any of the pharmaceutical compositions described herein comprising the steps of combining IFG and a pharmaceutically acceptable carrier. Some embodiments comprise the steps of combining IFG, a GCase and a pharmaceutically acceptable carrier. Further embodiments of the methods provided herein comprise dissolving the isofagomine in water, adjusting the pH to about 6.0, and adding the glucocerebrosidase to yield the composition.

In another aspect is provided a method of treating a disorder related to a dysfunction in a GCase pathway, or of preventing the manifestation of symptoms associated with a dysfunction in a GCase pathway, the method comprising administering a therapeutically effective amount of any one of the compositions described herein. In some embodiments, the composition is administered intravenously or subcutaneously. In some embodiments, the composition is administered subcutaneously, e.g., by subcutaneous injection. In some embodiments, the composition is administered twice weekly, once weekly, less often than once weekly, or once every other week.

Another aspect of this present disclosure relates to a method of treating Gaucher disease which method comprises administering to a patient in need of such a treatment i) a therapeutically effective amount of an isofagomine salt as above defined or a pharmaceutical composition thereof or ii) a therapeutically effective amount of a composition comprising isofagomine and a GCase, wherein isofagomine is a stabilizing excipient for the GCase. The treatment may be as a monotherapy or combination therapy. In another aspect the present disclosure relates to an isofagomine salt for use as a medicament, preferably for the use in treatment of Gaucher disease.

In another aspect the present disclosure is directed to methods of producing isofagomine salts comprising the steps of: i) dissolving an organic acid in a polar protic solvent to produce a solution 1; ii) dissolving isofagomine free base in a polar protic solvent to produce a solution 2; iii) combining solution 1 and solution 2, thereby forming a precipitate; iv) isolating the precipitate corresponding to the organic acid salt of isofagomine. In further embodiments, the organic acid is selected from quinic acid, fumaric acid, oxalic acid, malonic acid, D-tartaric acid, L-tartaric acid, succinic acid, cyclamic acid and ascorbic acid. In some embodiments, the isofagomine salt is in a crystalline form. In additional embodiments, the isofagomine free base is at least about 98% pure.

These aspects and preferred embodiments thereof are additionally also defined in the claims.

BRIEF DESCRIPTION OF THE DRAWINGS

FIG. 22 is a characteristic 1H NMR of isofagomine D-(−)-tartrate (1:1).

DETAILED DESCRIPTION

Definitions

Figure 1:
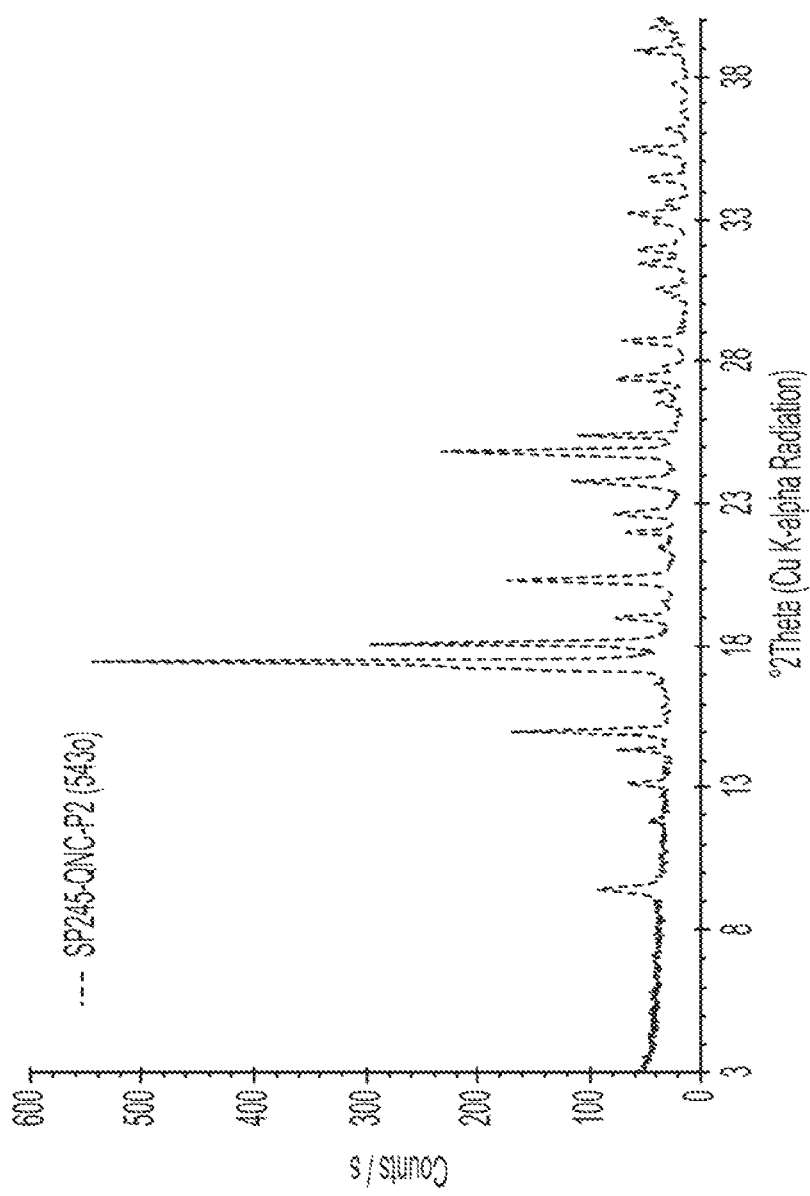
FIG. 1 is a characteristic x-ray powder diffraction (XRPD) spectrum of isofagomine quinate.

Novel forms and formulations provide an opportunity to improve manufacturing, formulation and performance characteristics of a pharmaceutical product. The present disclosure includes new forms of isofagomine with improved physicochemical properties, such as improved stability, flowability, and purity.

The terms used in this specification generally have their ordinary meanings in the art, within the context of this present disclosure and in the specific context where each term is used. Certain terms are discussed below or elsewhere in the specification, to provide additional guidance to the practitioner in describing the compositions and methods of the present disclosure as well as how to make and use them.

The terms "isofagomine" and "IFG", as used interchangeably herein, include reference to isofagomine as the free base form as well as any of the salt forms disclosed herein, unless particularly specified otherwise. The terms further include wherein the material may be in an amorphous or crystalline form, unless particularly specified.

The term "crystalline", as the term is used herein, refers to a material which may be hydrated and/or solvated, that has sufficient ordering of the chemical moiety to exhibit a discernable diffraction pattern by XRPD or other diffraction techniques. Often, a crystalline material that is obtained by direct crystallization of a compound dissolved in a solution or by interconversion of crystals obtained under different crystallization conditions, will have crystals that contain the solvent used in the crystallization, termed a crystalline solvate. Also, the specific solvent system and physical embodiment in which the crystallization is performed, collectively termed crystallization conditions, may result in the crystalline material having physical and chemical properties that are unique to the crystallization conditions, generally due to the orientation of the chemical moieties of the compound with respect to each other within the crystal and/or the predominance of a specific polymorphic form of the compound in the crystalline material. The scientists in this field are able to understand that physical and chemical properties discussed herein can be characterized, wherein the experimental errors depend on the conditions of instruments, the sample preparations and the purity of samples. In particular, the scientists in this field generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, generally, the experimental errors of the peak angles are 5% or less, so such errors shall be considered and generally the allowed errors are ±0.2° theta. In addition, due to the effect of the experimental factors including sample height, peak angles may have an overall shifting; generally, certain shifting is allowed. Hence, the scientists in this field may understand that, it is unnecessary that the X-ray diffraction pattern of a crystal form in the present disclosure should be exactly the same with X-ray diffraction patterns of the example shown herein. Any crystal forms whose X-ray diffraction patterns have the same or similar characteristic peaks should be within the scope of the present disclosure. The scientists in this field can compare the patterns shown in the present disclosure with that of an unknown crystal form in order to identify whether these two groups of patterns reflect the same or different crystal forms.

"Crystalline form" and "polymorphic form" as well as other related terms in the present disclosure refer to the solid compounds whose crystal structure is being in a special crystal form state. The difference in the physical and chemical properties of the polymorphs may be embodied in storage stability, compressibility, density, dissolution rate, etc. In extreme cases, the difference in solubility or dissolution rate may result in inefficient drugs, even developing toxicity.

The term "amorphous", as the term is used herein, refers to a composition comprising a compound that contains too little crystalline content of the compound to yield a discernable pattern by XRPD or other diffraction techniques. Glassy materials are a type of amorphous material. Glassy materials do not have a true crystal lattice, and technically resembling very viscous non-crystalline liquids. Rather than being true solids, glasses may better be described as quasi-solid amorphous material.

The term "volume(s) of solvent" as used herein refers to the milliliters of solvent used per gram of material to be dissolved. For example, 1 g of tartaric acid dissolved in 8 volumes of solvent would be dissolved in 8 milliliters of solvent.

The term "Gaucher disease" includes Type 1, Type 2 and Type 3 (including 3 a, 3b and 3 c), and intermediates and subgroups thereof based on phenotypic manifestations.

The terms "effective amount" and "amount effective" refer to the amount that is sufficient to result in a therapeutic response. A therapeutic response may be any response that a user (e.g., a clinician) will recognize as an effective response to the therapy, including improvements in one or more symptoms and surrogate clinical markers. Thus, a therapeutic response in a subject with Gaucher disease will generally be an amelioration of one or more symptoms of Gaucher disease. The "therapeutically effective amount" will vary depending on the formulation used, the type of Gaucher disease and its severity, and the age, weight, physical condition and responsiveness of the mammal to be treated. A therapeutic response will also be an amelioration of one or more, symptoms of Parkinson's disease, or other α-synucleinopathies such as Lewy Body Dementia, for which a composition herein is contemplated for treatment.

The phrase "pharmaceutically acceptable" refers to molecular entities and compositions that are physiologically tolerable and do not typically produce untoward reactions at an unacceptable level when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "about" refers to up to +/−10% of the value qualified by this term. For example, about 50 mM refers to 50 mM+/−5 mM; about 4% refers to 4%+/−0.4%.

As used herein, the singular forms "a," "an," and "the," include the plural unless the context clearly indicates otherwise. Thus, for example, reference "a" carrier includes one or more carriers.

The expressions "ambient temperature" and "room temperature," as used herein, are understood in the art and refer generally to a temperature, e.g., a reaction temperature, that is about the temperature of the room in which the reaction is carried out, e.g., typically a temperature from about 20 to 22° C. (68 to 72° F.). More specifically, the material or reaction mixture is not heated or cooled.

The term "subject" refers to any mammal, including but not limited to, any animal classified as such, including humans, non-human primates, primates, baboons, chimpanzees, monkeys, rodents (e.g., mice, rats), rabbits, cats, dogs, horses, cows, sheep, goats, pigs, etc. The term "subject" can be used interchangeably with the term "patient."

The phrases "parenteral administration", "administered parenterally" and "administer parenterally" as used herein refer to modes of administration other than enteral and topical administration, usually by injection, and include, without limitation, intravenous (IV), intramuscular, intraarterial, intrathecal, intracapsular, intraorbital, intracardiac, intradermal, intraperitoneal, transtracheal, subcutaneous (SC), subcuticular, intraarticular, subcapsular, subarachnoid, intraspinal, epidural, and intrasternal injection and infusion.

The terms "therapeutically effective dose," and "therapeutically effective amount," refer to that amount of a compound that results in prevention of symptoms, for example, prevention of 80%, 85%, 90%, 95%, 96%, 97%, 98%, or 99% of symptoms, e.g., symptoms of Gaucher disease in a subject diagnosed as having Gaucher disease), delay of onset of symptoms, or amelioration of symptoms of Gaucher disease. A therapeutically effective amount will, for example, be sufficient to treat, prevent, reduce the severity, delay the onset, and/or reduce the risk of occurrence of one or more symptoms of a disorder associated with Gaucher disease. The effective amount can be determined by methods well known in the art and as described in subsequent sections of this description.

The terms "treatment" and "therapeutic method" refer to treatment of an existing disorder and/or prophylactic/preventative measures for preventing occurrence or reduction of symptoms associated the disorder. Those in need of treatment may include individuals already having a particular medical disorder, such as a dysfunction in a GCase pathway, as well as those at risk of having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder or symptoms thereof.

The term "treating" refers to administering a therapy in an amount, manner, and/or mode effective to improve or prevent a condition, symptom, or parameter associated with a disorder (e.g., a disorder described herein) or to prevent onset, progression, or exacerbation of the disorder, to either a statistically significant degree or to a degree detectable to one skilled in the art. Accordingly, treating can achieve therapeutic benefits. An effective amount, manner, or mode can vary depending on the subject and may be tailored to the subject. In certain embodiments, treatment of a disorder related to a dysfunction in a GCase pathway (e.g., Gaucher disease), is a treatment which results in one or more of an increase in hemoglobin concentration, an increase in platelet level, a decrease in liver volume, a decrease in spleen volume, or a change in a skeletal parameter (e.g., an increase in bone mineral density), e.g., in a subject who has not been treated for the dysfunction in a GCase pathway. In certain embodiments, treatment of a disorder related to a dysfunction in a GCase pathway (e.g., Gaucher disease), is a treatment which results in one or more of an increase in hemoglobin concentration, an increase in platelet level, a decrease in liver volume, a decrease in spleen volume, or a change in a skeletal parameter (e.g., an increase in bone mineral density), or maintenance of one or more of these parameters, e.g., in a subject who has been treated for the dysfunction in a GCase pathway.

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order.

The terms "sustained release", "sustained release delivery" and "sustained release drug delivery" as used herein mean that a single administration of drug maintains the effective concentration of the drug in blood for a long period, for example, 12 hours or longer. For example, the general administration route of polypeptides is subcutaneous, intramuscular or intravenous (IV) injection.

The terms "individuals," "subject" or "patient" may be used interchangeably and refers to any mammal, including but not limited to, any animal classified as such, including humans, non-human primates, primates, baboons, chimpanzees, monkeys, rodents (e.g., mice, rats), rabbits, cats, dogs, horses, cows, sheep, goats, pigs, etc.

An "individual in need of treatment" is an individual that has developed, or is likely to develop, Gaucher disease or an α-synucleinopathy such as Parkinson's disease. In one embodiment, the individual is a member of the Ashkenazi Jewish population who has been diagnosed with or who has been identified as having an increased risk of developing Gaucher disease due to inherited mutations in the Gba gene. However, the term "individual" encompasses anyone in the world having, or genetically at risk of developing, Gaucher disease, or having at risk of developing an α-synucleinopathy such as Parkinson's disease.

The phrase "substantially pure," as used herein to describe an isofagomine salt, means that the isofagomine salt contains no more than about 2% of another compound. Preferably, the "substantially pure" isofagomine salt contains about 2% or less of any other compound, about 1.8% or less of any other compound, about 1.6% or less of any other compound, about 1.5% or less of any other compound, about 1.3% or less of any other compound. Even more preferably, the "substantially pure" isofagomine salt contains about 1% or less of any other compound, about 0.8% or less of any other compound, about 0.6% or less of any other compound, about 0.5% or less of any other compound, about 0.3% or less of any other compound.

Percent purity can be determined by those of skill in the art, including by HPLC analysis or analytical thin layer chromatography. Other methods are known to those of ordinary skill in the art and include the chromatographic methods and spectrophotometric methods.

The term "unit" with respect to GCase, velaglucerase, or velaglucerase alfa refers to the amount of these that is required to convert one micromole of p-nitrophenyl beta-D-glucopyranoside to p-nitrophenol, or 4-methylumbelliferone beta-D-glucopyranoside to 4-methylumbelliferone, per minute at 37° C.

In accordance with the present disclosure, specific salt forms of isofagomine are provided. The provided isofagomine salts, and crystalline forms thereof, have improved characteristics compared with previously described forms of isofagomine, which include improved synthetic manufacturability. For example, it may be easier to purify the described organic acid salts of IFG in solvents such as water and ethanol. Also, some of the provided forms, e.g., IFG-fumarate, have similar or greater stability than other known salt forms of isofagomine. IFG salts provided herein are also particularly suitable for industrial scale production, e.g., production of greater than 1 kg of product.

In some embodiments of the present disclosure, isofagomine salts of organic acids are prepared by the following general protocol:

Solution 1 is prepared as follows: an organic acid is dissolved in a polar protic organic solvent. The amount of solvent is not particularly limited. Preferably, the organic acid is dissolved in the solvent. Typically, 2 to 10 volumes of solvent, e.g., 2, 2.5, 3, 3.5, 4, 4.5, 5, 5.5, 6, 6.5, 7, 7.5, 8, 8.5, 9, 9.5 or 10 volumes of solvent, or any amount therebetween, may be used.

In one embodiment, the amount of solvent used is the minimal amount necessary to achieve complete dissolution at room temperature. Typically, the solution is prepared at room temperature, but embodiments are contemplated wherein the solvent is heated, for example, to accelerate dissolution or to produce a super saturated solution. The solution may be filtered to remove any undissolved material prior to the next step. Alternately, a slurry method may be used wherein the material is not completely dissolved prior to combination with solution 2 in the subsequent step.

Solution 2 is prepared as follows: an equimolar amount of isofagomine relative to the organic acid used in the preparation of solution 1 is dissolved in a polar protic organic solvent. The amount of solvent is not particularly limited. Preferably, isofagomine is dissolved in the solvent. Typically, 2 to 10 volumes of solvent, e.g., 2, 2.5, 3, 3.5, 4, 4.5, 5, 5.5, 6, 6.5, 7, 7.5, 8, 8.5, 9, 9.5 or 10 volumes of solvent, or any amount therebetween, may be used.

In one embodiment, the amount of solvent used is the minimal amount necessary to achieve complete dissolution at room temperature. Typically, the solution is prepared at room temperature, but embodiments are contemplated wherein the solvent is heated, for example, to accelerate dissolution or to produce a super saturated solution. The solution may be filtered to remove any undissolved material prior to the next step. Alternately, a slurry method may be used wherein the material is not completely dissolved prior to combination with solution 1 in the subsequent step.

In particular embodiments, solution 1 is prepared with an organic acid. Suitable organic acids for use with the present embodiments include quinic acid, maleic acid, fumaric acid, oxalic acid, malonic acid, D-tartaric acid, L-tartaric acid, succinic acid, cylamic acid and ascorbic acid.

Solution 2 is then added slowly to Solution 1, whereupon precipitate is formed. After agitation at room temperature, the obtained slurry is filtered, and the resultant solid material is washed with an alcoholic solvent, deliquored and then dried in vacuo. Isolated yields typically range between 40 and 80% of the theoretical yield.

In certain embodiments, the isofagomine obtained is selected from isofagomine quinate, isofagomine malate, isofagomine fumarate, isofagomine oxalate, isofagomine malonate, isofagomine succinate, isofagomine D-tartrate, isofagomine cyclamate and isofagomine ascorbate. In particular embodiments, the obtained isofagomine salt is crystalline as confirmed by measurement of diffraction peaks using, e.g., x-ray powder diffraction techniques or other diffraction techniques known in the art.

In a further embodiment, the isofagomine is selected from isofagomine quinate, isofagomine fumarate, isofagomine oxalate, isofagomine D-tartrate, is in a crystalline form characterized by three or more very strong, strong and medium intensity XRPD peaks listed in Tables 1, 3, 5, and 7, respectively.

In a particular embodiment IFG is isofagomine quinate characterized by the x-ray diffraction pattern having one or more, two or more or three or more characteristic peaks at 2theta values listed in Table 1, e.g., at least one, at least two or at least three selected from: $9.5°±0.2°$, $15.0°±0.2°$, $17.4°±0.2°$, $18.1°±0.2°$, $20.3°±0.2°$, $23.8°±0.2°$, $24.8°±0.2°$ and $25.4°±0.2°$. In a further embodiment, IFG is isofagomine quinate characterized by the x-ray diffraction pattern having at least one, at least two or at least three characteristic peaks at 2theta values of $17.4°±0.2°$, $15.0°±0.2°$, $18.1°±0.2°$, $20.3°±0.2°$ and $24.8°±0.2°$; In a particular embodiment, IFG is isofagomine quinate characterized by the x-ray diffraction pattern having at least one, at least two or at least three characteristic peaks at 2theta values of $15.0°±0.2°$, $17.4°±0.2°$, $18.1°±0.2°$ and $20.3°±0.2°$.

In a particular embodiment IFG is isofagomine fumarate characterized by the x-ray diffraction pattern having one or more, two or more or three or more characteristic peaks at 2theta values listed in Table 3, e.g., at least one, at least two or at least three selected from: $16.1°±0.2°$, $18.3°±0.2°$, $18.6°±0.2°$, $21.9°±0.2°$, $23.6°±0.2°$, $23.8°±0.2°$, and $25.5°±0.2°$. In a particular embodiment, IFG is isofagomine fumarate characterized by the x-ray diffraction pattern having at least one, at least two or at least three characteristic peaks at 2theta values of $23.6°±0.2°$, $23.8°±0.2°$ and $25.5°±0.2°$.

In a particular embodiment, IFG is isofagomine oxalate characterized by the x-ray diffraction pattern having one or more, two or more or three or more characteristic peaks at 2theta values listed in Table 5, e.g., at least one, at least two or at least three selected from: 27.8°±0.2°, 32.2°±0.2°, 35.3°±0.2°, 36.6°±0.2°, 37.4°±0.2°, 38.4°±0.2°, 18.5°±0.2°, 19.2°±0.2°, 21.4°±0.2°, 22.6°±0.2°, 24.5°±0.2°, 24.8°±0.2°, 26.8°±0.2°, 20.2°±0.2° and 23.7°±0.2°. In a particular embodiment, IFG is isofagomine oxalate characterized by the x-ray diffraction pattern having at least one, at least two or at least three characteristic peaks at 2theta values of 18.5°±0.2°, 19.2°±0.2°, 21.4°±0.2°, 22.6°±0.2°, 24.5°±0.2°, 24.8°±0.2°, 26.8°±0.2°, 20.2°±0.2° and 23.7°±0.2°. In a particular embodiment, IFG is isofagomine oxalate characterized by the x-ray diffraction pattern having at least one, at least two or at least three characteristic peaks at 2theta values of 20.2°±0.2°, and 23.7° 0.2°.

In a particular embodiment, IFG is isofagomine D-tartrate characterized by the x-ray diffraction pattern having one or more, two or more or three or more characteristic peaks at 2theta values listed in Table 5, e.g., at least one, at least two or at least three selected from: 9.8°±0.2°, 10.5°±0.2°, 15.0°±0.2°, 15.3°±0.2°, 15.8°±0.2°, 17.4°±0.2°, 17.9°±0.2°, 18.5°±0.2°, 18.9°±0.2°, 19.6°±0.2°, 21.1°±0.2°, 21.7°±0.2°, 22°±0.2°, 24.2°±0.2°, 24.8°±0.2°, 26.6°±0.2°, 27.1°±0.2°, 27.4°±0.2°, 33.8°±0.2°, 35.7°±0.2°, 36.5°±0.2° and 37.5°±0.2°. In a further embodiment, IFG is isofagomine D-tartrate characterized by the x-ray diffraction pattern having at least one, at least two or at least three characteristic peaks at 2theta values of 10.5°±0.2°, 15.0°±0.2°, 15.3°±0.2°, 18.5°±0.2°, 26.6°±0.2°, 21.1°±0.2°, 21.7°±0.2° and 24.2°±0.2°. In a particular embodiment, IFG is isofagomine D-tartrate characterized by the x-ray diffraction pattern having at least one, at least two or at least three characteristic peaks at 2theta values of 21.1°±0.2°, 21.7°±0.2° and 24.2°±0.2°.

The polar protic organic solvent for use with the present disclosure typically comprises one or more lower aliphatic alcohols, such as methanol, ethanol, n-propanol, isopropanol etc. and may also include water. Preferably, methanol and/or ethanol are used.

In one embodiment, the acid solution (solution 1) is seeded with previously obtained crystalline material of the desired isofagomine salt, e.g., in order to obtain a higher yield or to produce crystal growth more rapidly.

In certain embodiments, isofagomine free base is purified before dissolution for use in solution 2. Purification techniques are those known in the art and include chromatography. In one embodiment, purification of isofagomine includes chromatography on silica gel or via an ion exchange resin system. These chromatographic methods remove a variety of impurities, such as intermediates that formed during isofagomine synthesis, e.g., during the step of hydrogenation of (3R,4R,5S,6S)-6-(benzyloxy)-4,5-dihydroxytetrahydro-2H-pyran-3-carbonitrile to produce isofagomine. Some impurities that are removed by purification of isofagomine free base include dimeric amine species, a cyclic imine intermediate and other unidentified intermediates or byproducts. Specific impurities that are removed by purification of isofagomine free base include those identified below:

In an embodiment, the IFG free base for use in the presently described methods of making IFG salts contains less than 2%, 1.8%, 1.6%, 1.4% 1.2%, 1%, 0.8%, 0.6%, 0.4% 0.2%, of impurities. More specifically, the IFG free base for use in the presently described methods of making IFG salts contains less than 2%, 1.8%, 1.6%, 1.4% 1.2%, 1%, 0.8%, 0.6%, 0.4% 0.2%, of any one of the impurities SRD006961, SRD006927, SRD006987 and SRD006925. In further embodiments, the IFG free base does not comprise one or more of SRD006961, SRD006927, SRD006987 and SRD006925.

In a further embodiment, the IFG free base for use in the presently described methods of making IFG salts is at least 90%, 95%, 96%, 97%, 98%, 98.2%, 98.4%, 98.6%, 98.8%, 99%, 99.2%, 99.4%, 99.6%, 99.8% or 100% (w/w) pure.

In another embodiment, the produced IFG salt is at least 95%, 96%, 97%, 98%, 98.2%, 98.4%, 98.6, 98.8%, 99%, 99.2%, 99.3%, 99.4%, 99.5%, 99.6%, 99.7%, 99.8%, 99.9% or 100% (w/w) pure.

Glucocerebrosidase

Velaglucerase is human β-glucocerebrosidase (GCase) produced by gene-activation in a human cell line, such as by targeted recombination with a promoter that activates the endogenous β-glucocerebrosidase gene in the selected human cell line. Velaglucerase is secreted as a monomeric glycoprotein of approximately 63 kDa. Velaglucerase is composed of 497 amino acids with a sequence identical to the natural human protein. See Zimran et al., Blood Cells Mol Dis, 2007, 39: 115-118.

The glycosylation of velaglucerase alfa may be altered by using kifunensine, a mannosidase I inhibitor, during cell culture so as to produce a secreted protein containing primarily high-mannose type glycans having 6-9 mannose units per glycan, as described in more detail in WO 2013/130963.

Imiglucerase (Cerezyme®) is another form of recombinant human (3-glucocerebrosidase. Imiglucerase is recombinantly produced in Chinese Hamster Ovary (CHO) cells.

Taliglucerase alfa (Elelyso® or Uplyso®) is a recombinant glucocerebrosidase (prGCase) expressed in plant cells. Plant recombinant glucocerebrosidase can be obtained by methods described at least in U.S. Patent Publication Nos. 2009/0208477 and 2008/0038232 and PCT Publication Nos. WO 2004/096978 and WO 2008/132743.

Any of the recombinant GCase can be produced using bioreactors and production scale synthesis methods known in the art. Any number of production scale purification systems can be used.

Pharmaceutical Compositions

In certain embodiments, a pharmaceutical composition comprising isofagomine (IFG) and at least one pharmaceutically acceptable carrier is provided. In some embodiments, IFG is an organic acid salt form. In further embodiments, IFG is selected from isofagomine quinate, isofagomine formate, isofagomine malate, isofagomine oxalate, isofagomine malonate, isofagomine succinate, isofagomine cyclamate, isofagomine D-tartrate and isofagomine ascorbate. In additional embodiments, the isofagomine is selected from isofagomine quinate, isofagomine fumarate, isofagomine oxalate, isofagomine D-tartrate and is in a crystalline form. In further embodiments, the crystalline form is characterized by three or more very strong, strong and medium intensity XRPD peaks listed in Tables 1, 3, 5, and 7, respectively.

In certain embodiments, a composition comprising IFG is provided where IFG is effective as a novel excipient that stabilizes a glucocerebrosidase (GCase) enzyme in a formulation for injection as described herein and further stabilizes the GCase enzyme at the injection site and in vivo, i.e., IFG is a stabilizing agent for a GCase active ingredient. In some embodiments, the composition is an aqueous solution. In some embodiments, the composition is a lyophilizate. In another aspect, IFG is present in an amount sufficient to reduce degradation of the GCase active ingredient; in certain embodiments, the amount of IFG may be considerably less than the therapeutically effective amount of IFG alone or when IFG is administered in a therapeutically effective amount in combination with the GCase active ingredient in conventional combination therapy. In certain embodiments, IFG is in at least about a 2.5, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5-fold molar excess to the GCase. In further embodiments, the IFG in the composition comprises an amount which does not increase endogenous serum GCase activity if administered as a single active agent. In certain embodiments, IFG is present in an amount sufficient to maintain the stability of the GCase in the composition. In some embodiments, IFG is present in an amount sufficient to maintain the stability of the GCase in the composition for at least three days at 0-50° C. In some embodiments, IFG is present in an amount sufficient to maintain the stability of the GCase in the composition for at least 6 months at 0-40° C.

In a further aspect is provided a composition comprising a glucocerebrosidase (GCase) and IFG in a molar ratio of about 1:2.5 to about 1:5 or about 1:>2.5 (i.e., 1:x, where x is greater than 2.5). In further embodiments, x is greater than 2.5 and less than an amount that would increase endogenous serum GCase activity if administered as a single active agent. In some embodiments, the GCase is velaglucerase alfa. In some embodiments, the molar ratio of the GCase to the IFG is from about 1:1 to about 1:30. In some embodiments of IFG/GCase compositions described herein, the IFG is an IFG salt described herein.

In some embodiments of IFG/GCase compositions described herein, a composition is a dosage form that comprises from 0.5 to 5.0 mg/kg bodyweight GCase and also comprises IFG (including the freebase, salt and crystalline forms described herein), e.g., wherein IFG is in at least about a 1, 1.25, 1.5, 2, 2.5, 3, 4, or 5-fold molar excess to the GCase. In some embodiments, the IFG in the composition comprises an amount which does not increase endogenous serum GCase activity if administered as a single agent. In some embodiments, the composition comprises from 0.8 to 4.0 mg/kg GCase. In some embodiments, the composition comprises from 1.0 to 3.0 mg/kg GCase. In some embodiments, the composition comprises from 1.2 to 2.0 mg/kg GCase. In some embodiments, the composition comprises about 1.5 mg/kg GCase. In some embodiments, the composition comprises 1.5 mg/kg GCase. In some embodiments, the composition comprises 2.0 to 5.0 mg/kg GCase. In some embodiments, the composition comprises 2.25 to 4.5 mg/kg GCase. In some embodiments, the composition comprises 2.25 to 3.75 mg/kg GCase. In some embodiments, the composition comprises 3.5 to 5.0 mg/kg GCase. In some embodiments, the IFG is in a 1 to 5 or a 1 to 10-fold molar ratio to the GCase. In some embodiments, the IFG is in a 2 to 10-fold molar ratio of GCase. In some embodiments, the IFG is in a 10 to 30-fold molar ratio to the GCase. In some embodiments, the IFG is in a 30 to 100-fold molar ratio to the GCase. In some embodiments, the IFG is in a 2.5 to 3.5-fold molar ratio to the GCase. In some embodiments, the IFG is in a 3-fold molar ratio to the GCase.

The concentration of GCase in any of the provided compositions, e.g., a lyophilized composition upon reconstitution, can be from about 60 mg/ml to about 180 mg/ml, from about 65 mg/ml to about 175 mg/ml, from about 70 mg/ml to about 170 mg/ml, from about 75 mg/ml to about 165 mg/ml, from about 80 mg/ml to about 160 mg/ml, from about 85 mg/ml to about 155 mg/ml, from about 90 mg/ml to about 150 mg/ml, from about 95 mg/ml to about 145 mg/ml, from about 100 mg/ml to about 140 mg/ml, from about 105 mg/ml to about 135 mg/ml, from about 110 mg/ml to about 130 mg/ml, or from about 115 mg/ml to about 125 mg/ml. In alternative embodiments, the concentration of GCase in any of the provided compositions can be in a range between any two concentrations selected from: 60 mg/ml, 63 mg/ml, 66 mg/ml, 69 mg/ml, 72 mg/ml, 75 mg/ml, 78 mg/ml, 81 mg/ml, 84 mg/ml, 87 mg/ml, 90 mg/ml, 93 mg/ml, 96 mg/ml, 99 mg/ml, 102 mg/ml, 105 mg/ml, 108 mg/ml, 111 mg/ml, 114 mg/ml, 117 mg/ml, 120 mg/ml, 123 mg/ml, 126 mg/ml, 129 mg/ml, 132 mg/ml, 135 mg/ml, 138 mg/ml, 141 mg/ml, 144 mg/ml, 147 mg/ml, 150 mg/ml, 153 mg/ml, 156 mg/ml, 159 mg/ml, 162 mg/ml, 165 mg/ml, 168 mg/ml, 171 mg/ml, 174 mg/ml, 177 mg/ml, and 180 mg/ml. In certain embodiments, the concentration of GCase in any of the provided compositions from about 120 mg/ml to about 160 mg/ml, from about 125 mg/ml to about 155 mg/ml, from about 130 mg/ml to about 150 mg/ml, from about 135 mg/ml to about 145 mg/ml, or about 140 mg/ml.

In an alternative embodiment, the concentration of GCase in any of the compositions disclosed herein, e.g., a lyophilized composition upon reconstitution, can be from about 30 mg/ml to about 200 mg/ml, from about 40 to about 180 mg/ml, from about 40 mg/ml to about 180 mg/ml, from about 50 mg/ml to about 160 mg/ml, from about 55 mg/ml to about 140 mg/ml, from about 60 to about 120 mg/ml, from about 0.5 to about 10 mg/ml, from about 5 to about 15 mg/ml, from about 10 to about 20 mg/ml, from about 15 to about 25 mg/ml, from about 20 to about 30 mg/ml, from about 25 to about 35 mg/ml, from about 30 to about 40 mg/ml, from about 2 to about 8 mg/ml, from about 5 to about 11 mg/ml, from about 8 to about 14 mg/ml, from about 11 to about 17 mg/ml, from about 14 to about 20 mg/ml, from about 17 to about 23 mg/ml, from about 20 to about 26 mg/ml, from about 23 to about 29 mg/ml, from about 26 to about 32 mg/ml, from about 29 to about 35 mg/ml, from about 32 to about 38 mg/ml, from about 2 to about 5 mg/ml, from about 5 to about 8 mg/ml, from about 8 to about 11 mg/ml, from about 11 to about 14 mg/ml, from about 14 to about 17 mg/ml, from about 17 to about 20 mg/ml, from about 20 to about 23 mg/ml, from about 23 to about 26 mg/ml, from about 26 to about 29 mg/ml, from about 29 to about 32 mg/ml, from about 32 to about 35 mg/ml, from about 35 to about 38 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, or about 40 mg/ml.

The concentration of GCase can be from 50 Units/ml to 200 Units/ml, 70 Units/ml to 160 Units/ml, 80 Units/ml to 175 Units/ml, 90 Units/ml to 190 Units/ml, 60 Units/ml to 145 Units/ml, 50 Units/ml to 130 Units/ml, 80 Units/ml to 140 Units/ml, 70 Units/ml to 120 Units/ml, 60 Units/ml to 100 Units/ml, 50 Units/ml to 85 Units/ml, 90 Units/ml to 160 Units/ml, 100 Units/ml to 180 Units/ml, 120 Units/ml to 200 Units/ml, 90 Units/ml to 125 Units/ml, 60 Units/ml to 105 Units/ml, 70 Units/ml to 100 Units/ml, 60 Units/ml to 90 Units/ml, 50 Units/ml to 80 Units/ml, 100 Units/ml to 140 Units/ml, 115 Units/ml to 160 Units/ml, 130 Units/ml to 180 Units/ml, 145 Units/ml to 200 Units/ml, 100 Units/ml to 115 Units/ml, 90 Units/ml to 105 Units/ml, 80 Units/ml to 95 Units/ml, 70 Units/ml to 85 Units/ml, 60 Units/ml to 75 Units/ml, 50 Units/ml to 65 Units/ml, 110 Units/ml to 125 Units/ml, 120 Units/ml to 135 Units/ml, 130 Units/ml to 145 Units/ml, 140 Units/ml to 160 Units/ml, 160 Units/ml to 180 Units/ml, 180 Units/ml to 200 Units/ml, about 50 Units/ml, about 60 Units/ml, about 70 Units/ml, about 80 Units/ml, about 90 Units/ml, about 100 Units/ml, about 110 Units/ml, about 120 Units/ml, about 130 Units/ml, about 140 Units/ml, about 150 Units/ml, about 160 Units/ml, about 170 Units/ml, about 180 Units/ml, about 190 Units/ml, about 200 Units/ml, 50 Units/ml, 60 Units/ml, 70 Units/ml, 80 Units/ml, 90 Units/ml, 100 Units/ml, 110 Units/ml, 120 Units/ml, 130 Units/ml, 140 Units/ml, 150 Units/ml, 160 Units/ml, 170 Units/ml, 180 Units/ml, 190 Units/ml, or 200 Units/ml.

In various embodiments, the composition comprises a glucocerebrosidase (GCase) and an isofagomine (IFG), wherein IFG can be a freebase, salt or crystalline form provided herein, wherein IFG is present in a molar ratio of at least about 1:1, 1:1.5, 1:2, or 1:2.5 (GCase:IFG). The molar ratio of GCase to IFG, can be in a range between any two values selected from: 1:1, 1:1.5, 1:2, 1:2.5, 1:2.6, 1:2.7, 1:2.8, 1:2.9, 1:3.0, 1:3.1, 1:3.2, 1:3.3, 1:3.4, 1:3.5, 1:3.6, 1:3.7, 1:3.8, 1:3.9, 1:4.0, 1:4.1, 1:4.2, 1:4.3, 1:4.4, 1:4.5, 1:4.6, 1:4.7, 1:4.8, 1:4.9, 1:5.0, 1:5.1, 1:5.2, 1:5.3, 1:5.4, 1:5.5, 1:5.6, 1:5.7, 1:5.8, 1:5.9, 1:6.0, 1:6.1, 1:6.2, 1:6.3, 1:6.4, 1:6.5, 1:6.6, 1:6.7, 1:6.8, 1:6.9, 1:7.0, 1:7.1, 1:7.2, 1:7.3, 1:7.4, 1:7.5, 1:7.6, 1:7.7, 1:7.8, 1:7.9, 1:8.0, 1:8.1, 1:8.2, 1:8.3, 1:8.4, 1:8.5, 1:8.6, 1:8.7, 1:8.8, 1:8.9, 1:9.0, 1:9.1, 1:9.2, 1:9.3, 1:9.4, 1:9.5, 1:9.6, 1:9.7, 1:9.8, 1:9.9, 1:10.0, 1:10.1, 1:10.2, 1:10.3, 1:10.4, 1:10.5, 1:10.6, 1:10.7, 1:10.8, 1:10.9, 1:11.0, 1:11.1, 1:11.2, 1:11.3, 1:11.4, 1:11.5, 1:11.6, 1:11.7, 1:11.8, 1:11.9, 1:12.0, 1:12.1, 1:12.2, 1:12.3, 1:12.4, 1:12.5, 1:12.6, 1:12.7, 1:12.8, 1:12.9, 1:13.0, 1:13.1, 1:13.2, 1:13.3, 1:13.4, 1:13.5, 1:13.6, 1:13.7, 1:13.8, 1:13.9, 1:14.0, 1:14.1, 1:14.2, 1:14.3, 1:14.4, 1:14.5, 1:14.6, 1:14.7, 1:14.8, 1:14.9, 1:15.0, 1:15.1, 1:15.2, 1:15.3, 1:15.4, 1:15.5, 1:15.6, 1:15.7, 1:15.8, 1:15.9, 1:16.0, 1:16.1, 1:16.2, 1:16.3, 1:16.4, 1:16.5, 1:16.6, 1:16.7, 1:16.8, 1:16.9, 1:17.0, 1:17.1, 1:17.2, 1:17.3, 1:17.4, 1:17.5, 1:17.6, 1:17.7, 1:17.8, 1:17.9, 1:18.0, 1:18.1, 1:18.2, 1:18.3, 1:18.4, 1:18.5, 1:18.6, 1:18.7, 1:18.8, 1:18.9, 1:19.0, 1:19.1, 1:19.2, 1:19.3, 1:19.4, 1:19.5, 1:19.6, 1:19.7, 1:19.8, 1:19.9, 1:20.0, 1:20.1, 1:20.2, 1:20.3, 1:20.4, 1:20.5, 1:20.6, 1:20.7, 1:20.8, 1:20.9, 1:21.0, 1:21.1, 1:21.2, 1:21.3, 1:21.4, 1:21.5, 1:21.6, 1:21.7, 1:21.8, 1:21.9, 1:22.0, 1:22.1, 1:22.2, 1:22.3, 1:22.4, 1:22.5, 1:22.6, 1:22.7, 1:22.8, 1:22.9, 1:23.0, 1:23.1, 1:23.2, 1:23.3, 1:23.4, 1:23.5, 1:23.6, 1:23.7, 1:23.8, 1:23.9, 1:23.9, 1:24.0, 1:24.1, 1:24.2, 1:24.3, 1:24.4, 1:24.5, 1:24.6, 1:24.7, 1:24.8, 1:24.9, 1:25.0, 1:25.1, 1:25.2, 1:25.3, 1:25.4, 1:25.5, 1:25.6, 1:25.7, 1:25.8, 1:25.9, 1:26.0, 1:26.1, 1:26.2, 1:26.3, 1:26.4, 1:26.5, 1:26.6, 1:26.7, 1:26.8, 1:26.9, 1:27.0, 1:27.1, 1:27.2, 1:27.3, 1:27.4, 1:27.5, 1:27.6, 1:27.7, 1:27.8, 1:27.9, 1:28.0, 1:28.1, 1:28.2, 1:28.3, 1:28.4, 1:28.5, 1:28.6, 1:28.7, 1:28.8, 1:28.9, 1:29.0, 1:29.1, 1:29.2, 1:29.3, 1:29.4, 1:29.5, 1:29.6, 1:29.7, 1:29.8, 1:29.9, or 1:30.0.

The molar ratio of GCase to IFG, can be from 1:2.5 to 1:3.5, from 1:2.6 to 1:3.4, from 1:2.7 to 1:3.5, from 1:2.7 to 1:3.4, from 1:2.5 to 1:3.3, from 1:2.8 to 1:3.5, from 1:2.8 to 1:3.3, from 1:2.7 to 1:3.2, from 1:2.6 to 1:3.1, from 1:2.5 to 1:3.0, from 1:2.9 to 1:3.3, from 1:2.8 to 1:3.2, from 1:2.7 to 1:3.1, from 1:2.6 to 1:3.0, from 1:2.5 to 1:2.9, from 1:3.0 to 1:3.4, or from 1:3.1 to 1:3.5.

The molar ratio of GCase to IFG, can be from 1:7 to 1:33, from 1:8 to 1:32, from 1:9 to 1:33, from 1:7 to 1:31, from 1:9 to 1:31, from 1:8 to 1:30, from 1:7 to 1:29, from 1:10 to 1:32, from 1:11 to 1:33, from 1:7 to 1:29, from 1:10 to 1:30, from 1:9 to 1:29, from 1:8 to 1:28, from 1:7 to 1:27, from 1:11 to 1:31, from 1:12 to 1:32, from 1:13 to 1:33, from 1:11 to 1:29, from 1:10 to 1:28, from 1:9 to 1:27, from 1:8 to 1:26, from 1:7 to 1:25, from 1:12 to 1:30, from 1:13 to 1:31, from 1:14 to 1:32, from 1:15 to 1:33, from 1:13 to 1:29, from 1:12 to 1:28, from 1:11 to 1:27, from 1:10 to 1:26, from 1:9 to 1:25, from 1:8 to 1:24, from 1:7 to 1:23, from 1:14 to 1:30, from 1:15 to 1:31, from 1:16 to 1:32, from 1:17 to 1:33, from 1:14 to 1:28, from 1:13 to 1:27, from 1:12 to 1:26, from 1:11 to 1:25, from 1:10 to 1:24, from 1:9 to 1:23, from 1:8 to 1:22, from 1:7 to 1:21, from 1:15 to 1:29, from 1:16 to 1:30, from 1:17 to 1:31, from 1:18 to 1:32, from 1:19 to 1:33, from 1:15 to 1:27, from 1:14 to 1:26, from 1:13 to 1:25, from 1:12 to 1:24, from 1:11 to 1:23, from 1:10 to 1:22, from 1:9 to 1:21, from 1:8 to 1:20, from 1:7 to 1:19, from 1:16 to 1:28, from 1:17 to 1:29, from 1:18 to 1:30, from 1:19 to 1:31, from 1:20 to 1:32, or from 1:21 to 1:33.

The molar ratio of GCase to IFG, can be from 1:16 to 1:26, from 1:15 to 1:25, from 1:14 to 1:24, from 1:13 to 1:23, from 1:12 to 1:22, from 1:11 to 1:31, from 1:10 to 1:30, from 1:9 to 1:29, from 1:8 to 1:28, from 1:7 to 1:27, from 1:17 to 1:27, from 1:18 to 1:28, from 1:19 to 1:29, from 1:20 to 1:30, from 1:21 to 1:31, from 1:22 to 1:32, from 1:23 to 1:33, from 1:17 to 1:25, from 1:14 to 1:24, from 1:13 to 1:23, from 1:12 to 1:22, from 1:11 to 1:21, from 1:10 to 1:20, from 1:9 to 1:19, from 1:18 to 1:26, from 1:19 to 1:27, from 1:20 to 1:28, from 1:21 to 1:29, from 1:22 to 1:30, from 1:23 to 1:31, from 1:18 to 1:24, from 1:17 to 1:23, from 1:16 to 1:22, from 1:15 to 1:21, from 1:14 to 1:20, from 1:13 to 1:19, from 1:12 to 1:18, from 1:11 to 1:17, from 1:19 to 1:25, from 1:20 to 1:26, from 1:21 to 1:27, from 1:22 to 1:28, from 1:23 to 1:29, from 1:24 to 1:30, from 1:19 to 1:23, from 1:17 to 1:21, from 1:15 to 1:19, from 1:13 to 1:17, from 1:11 to 1:15, from 1:9 to 1:13, from 1:7 to 1:11, from 1:21 to 1:25, from 1:23 to 1:27, from 1:25 to 1:29, from 1:27 to 1:31, from 1:29 to 1:33, from 1:20 to 1:23, from 1:18 to 1:21, from 1:16 to 1:19, from 1:14 to 1:17, from 1:12 to 1:15, from 1:10 to 1:13, from 1:8 to 1:11, from 1:22 to 1:25, from 1:24 to 1:27, from 1:26 to 1:29, from 1:28 to 1:31, or from 1:30 to 1:33.

The molar ratio of GCase to IFG, can be 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:35, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, or 1:100.

The molar ratio of GCase to IFG, can be from 1:30 to 1:100, from 1:30 to 1:80, from 1:40 to 1:90, from 1:50 to 1:100, from 1:30 to 1:60, from 1:40 to 1:70, from 1:50 to 1:80, from 1:60 to 1:90, from 1:70 to 1:100, from 1:30 to 1:50, from 1:40 to 1:60, from 1:50 to 1:70, from 1:60 to 1:80, from 1:70 to 1:90, from 1:80 to 1:100, from 1:30 to 1:40, from 1:40 to 1:50, from 1:50 to 1:60, from 1:60 to 1:70, from 1:70 to 1:80, from 1:80 to 1:90, or from 1:90 to 1:100.

In other various embodiments described herein, the composition comprises a glucocerebrosidase (GCase) and an IFG fumarate in a molar ratio of 1:2.5-1:3.5.

In other various embodiments described herein, the composition comprises a glucocerebrosidase (GCase) and an IFG quinate in a molar ratio of 1:2.5-1:3.5.

In other various embodiments described herein, the composition comprises a glucocerebrosidase (GCase) and an IFG oxalate in a molar ratio of 1:2.5-1:3.5.

In other various embodiments described herein, the composition comprises a glucocerebrosidase (GCase) and an IFG succinate in a molar ratio of 1:2.5-1:3.5.

In other various embodiments described herein, the composition comprises a glucocerebrosidase (GCase) and an IFG cyclamate in a molar ratio of 1:2.5-1:3.5.

In another aspect is provided a method of preparing any of the of IFG or IFG/GCase compositions described herein. In one aspect, the method comprises dissolving IFG, or salt thereof as described herein, in a solvent, e.g., water), adjusting the pH to about 6.0, and adding the glucocerebrosidase (GCase) to yield the composition. In some embodiments, the method further comprises lyophilizing the IFG before adding GCase. In some embodiments, the method further comprises adding polysorbate 20 to 0.01%. In some embodiments, the method further comprises filtering the composition through a 0.22 µm membrane. In some embodiments, the IFG is present in an amount sufficient to maintain the stability of the GCase in the composition. In some embodiments, IFG is present in an amount sufficient to maintain the stability of the GCase in the composition for at least three days at 0-50° C. In some embodiments, IFG is present in an amount sufficient to maintain the stability of the GCase in the composition for at least 6 months at 0-40° C.

In some embodiments, the composition comprises 45-120 mg/mL of velaglucerase alfa and 0.2 to 1.8 mg/mL crystalline IFG D-tartrate. In some embodiments, the composition comprises 60 mg/mL of velaglucerase alfa and 0.9 mg/mL crystalline IFG D-tartrate.

In some embodiments, the composition comprises 60-180 mg/mL of velaglucerase alfa and IFG in a molar ratio as described above, e.g., about 1:2.5 to about 1:3.5, or about 1:3.3. In certain embodiments, the composition further comprises a buffer (e.g., sodium citrate or citric acid or a combination thereof) from about 5 mM to about 15 mM or about 10 mM; a carbohydrate (e.g., sucrose) in an amount from about 200 mM to about 300 mM or about 250 mM, and a surfactant (e.g., PS20, PS80 or poloxamer 188) in an amount ranging from about 0.05% to about 0.5% or about 0.1%. In certain embodiments, IFG is in a free base form. In alternative embodiments, IFG is in a salt form wherein the salt is prepared from an organic acid, e.g., quinic acid, maleic acid, fumaric acid, oxalic acid, malonic acid, D-tartaric acid, L-tartaric acid, succinic acid, cylamic acid or ascorbic acid. In another embodiment the IFG salt is in a crystalline form.

Any of the preceding embodiments, wherein the isofagomine compound used for stabilization of GCase in solution is isofagomine tartrate. Any of the preceding embodiments, wherein the isofagomine compound used for stabilization of GCase in solution is isofagomine fumarate. In certain embodiments, the GCase is velaglucerase alfa.

In further embodiments of the compositions described herein, GCase is stable for 18 months, 20 months, 24 months, 26 months, 28 months, 30 months, 32 months, 34 months, 36 months, 38 months, 40 months, 42 months, 44 months, 46 months, or 48 months upon storage at ≤−65° C. In certain embodiments, GCase is stable for through 18 months when stored at the long-term storage condition of ≤−65° C. In certain embodiments, GCase is stable for through 30 months when stored at the long-term storage condition of ≤−65° C. In certain embodiments, GCase is stable for 8 months, 9 months, 10 months, 11 months, 12 months, 13 months, 14 months, 15 months, 16 months, 17 months, 18 months, 19 months, upon storage at −20±5° C.

In certain embodiments, GCase is stable for 1 month, 2 months, 3 months, 4 months, 5 months, 6 months, upon storage at 5±3°.

Pharmaceutical Carriers

The pharmaceutical compositions of the present disclosure can include one or more pharmaceutically acceptable carriers. As used herein, the language "pharmaceutically acceptable carrier" is intended to include any and all solvents, excipients, dispersion media, coatings, antibacterial and antifungal agents, isotonic and adsorption delaying agents, and the like, compatible with pharmaceutical administration. Pharmaceutical formulation is a well-established art, and is further described, e.g., in Gennaro (ed.), Remington: *The Science and Practice of Pharmacy*, 20th ed., Lippincott, Williams & Wilkins (2000) (ISBN: 0683306472); Ansel et al., *Pharmaceutical Dosage Forms and Drug Delivery Systems*, 7th Ed., Lippincott Williams & Wilkins Publishers (1999) (ISBN: 0683305727); and Kibbe (ed.), *Handbook of Pharmaceutical Excipients American Pharmaceutical Association*, 3rd ed. (2000) (ISBN: 091733096X). Except insofar as any conventional media or agent is incompatible with the active compound, such media can be used in the compositions of the disclosure. Supplementary active compounds can also be incorporated into the compositions.

Sterile injectable solutions can be prepared by incorporating IFG, and optionally another active ingredient such as GCase, in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the composition of sterile injectable solutions, the preferred methods of composition are vacuum drying and freeze-drying, e.g., lyophilization, which yields a powder of the active ingredient plus any additional desired ingredient from a previously sterile-filtered solution thereof.

The compounds (e.g., IFG and IFG/GCase compositions described herein) can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

For IV administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. The composition should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Proper fluidity can be maintained, for example, by the use of a coating such as lecithin, by the maintenance of the required particle size in the case of dispersion, and by the use of surfactants including non-ionic poly (ethylene oxide) (PEO)-poly (propylene oxide) (PPO) copolymers (e.g., poloxamers 68, 88, 98, 108, 124, 188, 237, 338, and 407) and polysorbate-type nonionic surfactants formed by the ethoxylation of sorbitan before the addition of lauric acid (e.g., polysorbate 20 also known as polyoxyethylene (20) sorbitan monolaurate). Prevention of microorganism action can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged stability of the injectable compositions can be brought about by including an agent which delays adsorption, for example, aluminum monostearate, human serum albumin and gelatin.

Antioxidants and Other Stabilizers

The IFG and GCase/IFG compositions described herein may further comprise an antioxidant. One suitable antioxidant is cysteine. Cysteine may be present at from 0.030% to 0.100%, 0.050% to 0.080%, 0.040% to 0.070%, 0.030% to 0.060%, 0.060% to 0.090%, 0.070% to 0.100%, 0.065% to 0.080%, 0.060% to 0.075%, 0.055% to 0.070%, 0.050% to 0.065%, 0.070% to 0.085%, 0.075% to 0.090%, about 0.065%, about 0.070%, about 0.075%, about 0.080%, 0.065%, 0.070%, 0.075%, or 0.080%. Without wishing to be bound by theory, cysteine may further stabilize GCase.

The IFG and GCase/IFG compositions described herein may further comprise a carbohydrate such as sucrose or trehalose. The carbohydrate, e.g., sucrose or trehalose, may be present at from 12% to 19%, 13% to 18%, 14% to 17%, 12% to 15%, 13% to 16%, 15% to 17%, about 16%, or 16%. Without wishing to be bound by theory, sucrose or trehalose may further stabilize GCase by decreasing the availability of thiol (—SH) groups.

The IFG and GCase/IFG compositions herein may further comprise a detergent. The detergent may be polysorbate 20 or any number of poloxamer-based compounds.

In certain embodiments, the stability of GCase is at least 5-80% greater (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% greater), under pre-selected conditions, than the stability of GCase in a composition which differs by lacking the carbohydrate (sucrose or trehalose), the antioxidant, or both the carbohydrate and the antioxidant.

The IFG and GCase/IFG compositions may be purged of oxygen prior to storage in a container. Further, the container is ideally gas tight so as to prevent intrusion of oxygen. The GCase in the compositions described herein, e.g., liquid compositions containing GCase, may have prolonged stability. For example, under pre-selected conditions, e.g., upon storage in a gas tight container, at a temperature of 2-8° C. for a period of up to 3, 6, 9, 12, or 24 months (or in some embodiments longer), GCase in the composition will retain at least 50, 55, 60, 65, 70, 75, 80, 85, 90, 95, 99, or 100% of the stability it had prior to storage.

A suitable protein concentration can be tested for by providing a composition containing 0.075% cysteine, 16% sucrose, adjusting the pH to 5.7, adjusting the GCase to a candidate concentration, and purging the composition of 02. The stability of GCase in the GCase/IFG, e.g., GCase/IFG, composition at the candidate concentration, measured, e.g., as a percent aggregation or degradation, at a predetermined time is compared with one or more standards. The stabilities of the GCase at each concentration are compared. Suitability can be shown by the candidate concentration having comparable or better effects on stability than a concentration described herein.

GCase stability can be measured by any of the methods described throughout this application, e.g., by measuring protein aggregation or protein degradation. Protein aggregation can be determined, e.g., by size exclusion chromatography, non-denaturing PAGE, or other methods for determining size, etc. Protein degradation can be determined, e.g., by reverse phase HPLC, non-denaturing PAGE, ion-exchange chromatography, SEC, SEC HPLC, peptide mapping, or similar methods.

pH can have an influence on the stability of GCase in the various GCase/IFG compositions described herein. pH can affect the conformation and/or aggregation and/or degradation and/or the reactivity of the GCase. Buffers that can be used to adjust the pH of a protein composition include salts solutions of histidine, citrate, phosphate, glycine, succinate, acetate, glutamate, Tris, tartrate, aspartate, maleate, and lactate. In certain embodiments the IFG/GCase formulation comprises a sodium citrate buffer.

Surfactants

The IFG and GCase/IFG compositions described herein may further comprise one or more surfactants. Without wishing to be bound by theory, surfactants can increase protein stability, such as by providing an air/liquid interface that can reduce protein degradation upon shaking or during shipment. A surfactant may be selected that increases protein stability, such as by not causing protein degradation, in a particular liquid composition. Suitable surfactants include non-ionic poly (ethylene oxide) (PEO)-poly (propylene oxide) (PPO) copolymers (e.g., poloxamers 68, 88, 98, 108, 124, 188, 237, 338, and 407) and polysorbate-type nonionic surfactants formed by the ethoxylation of sorbitan before the addition of and an unsaturated fatty acid such as lauric acid or oleic acid (e.g., polysorbate 20 also known as polyoxyethylene (20) sorbitan monolaurate, and polysorbate 80 also known as polyoxyethylene (80) sorbitan monooleate). An exemplary surfactant is poloxamer 188, PS20, PS80 and/or Pluronic F68. The surfactant can be present in an amount between about 0.005% and about 5%, e.g., between about 0.01% and about 1%, e.g., about 0.025% and about 0.5%, e.g., about 0.03% and about 0.25%, e.g., about 0.04 to about 0.1%, e.g., about 0.05% to about 0.075%, e.g., 0.05%. An ideal surfactant or combination thereof is one that is not modified or cleaved by GCase.

For example, a candidate surfactant can be tested by providing a composition containing 2 mg/ml GCase, an amount of IFG, 0.075% cysteine, 16% sucrose, then adjusting the pH to 5.7, then adding the candidate surfactant, and purging the composition of 02. The stability of the GCase/IFG composition containing the candidate surfactant is measured, e.g., as a percent aggregation or degradation, at a predetermined time compared with one or more standards. For example, a suitable standard would be a composition similar to the test conditions except that a surfactant is not added to the composition. The stabilities of the treated (containing the surfactant) and untreated (lacking a surfactant) compositions may be compared in conditions simulating "real world" scenarios, e.g., storage and shipping. A standard can be a composition similar to the test composition except that another surfactant is used instead of poloxamer 188. Poloxamer 188 would then be a standard for the basis of comparison. Suitability can be shown by the candidate surfactant having comparable or better effects on stability than a surfactant described herein. If the candidate surfactant is determined to be suitable (e.g., it increases stability of the composition as compared to one of the standards), the concentration of the candidate surfactant can be refined. For example, the concentration can be increased or decreased over a range of values and compared to the standard and to the other concentrations being tested to determine which concentration causes the greatest increase in stability.

Alternatively, a combination of two or more surfactants is used in the compositions described herein. The suitability of the combination can be tested as described above by comparing the stability of a GCase/IFG composition with the test combination of surfactants with the stability of a GCase/IFG composition with poloxamer 188.

Packaging and Delivery

The IFG and IFG/GCase compositions described herein can be administered with various medical devices. For example, a composition described herein can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the disclosure include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules also are known.

The IFG and GCase/IFG compositions described herein can be packaged in a two chamber syringe. For example, the IFG and GCase/IFG compositions in lyophilized form can be placed into a first syringe chamber and a liquid can be present in a second syringe chamber (see e.g., U.S. Published Application No. 2004-0249339).

The IFG and GCase/IFG compositions described herein can be packaged in a needleless syringe (see e.g., U.S. Pat. Nos. 6,406,455 and 6,939,324). Briefly, as one example, the injection device includes: a gas chamber containing a gas or a source of gas; a port which can allow for release of gas from the gas chamber; a plunger, which upon the release of gas from the gas chamber, can cause movement of at least a first piston; a first piston; a second piston; a first chamber, e.g. a chamber useful for drug storage and mixing; a piston housing, in which are disposed the first piston, the second piston and the first chamber; a displacement member which can, independent of the motive power of gas from the gas chamber, cause movement of one or both of the first and second pistons (the displacement member can be the plunger or a separate member); an orifice suitable for needleless injection in communication with the first chamber; wherein the first and second piston, are slideably disposed within the piston housing, and the displacement member, the source of gas, and the plunger are disposed such that: in a first position of the pistons, a second chamber, e.g., a fluid reservoir, is defined within the piston housing by the first piston, the piston housing and the second piston, the displacement member can move one or both of the pistons into a second position wherein the first piston is in a position such that the second chamber, which can be a fluid reservoir, is in communication with the first chamber, which can be a drug storage and mixing chamber, and the second piston is moved in the direction of the first piston, thereby decreasing the volume of the second chamber and allowing the transfer of fluid from the second chamber to the first chamber, the plunger, upon release of gas from the gas chamber, causes the first piston to move so as to decrease the volume of the first chamber allowing a substance to be expelled through the orifice and from the chamber and, e.g., to a subject.

The needleless syringe can include separate modules for a first component, e.g., a dry or liquid component, and a second component, e.g., a liquid component. The modules can be provided as two separate components and assembled, e.g., by the subject who will administer the component to himself or herself, or by another person, e.g., by an individual who provides or delivers health care. Together, the modules can form all or part of the piston housing of devices described herein. The devices can be used to provide any first and second component where it is desirable to store or provide the components separately and combine them prior to administration to a subject.

Methods of Treatment

In another aspect is provided a method of treating a disorder related to a dysfunction in a GCase pathway comprising administering any of the compositions described herein. In another aspect is provided the disclosed compositions comprising GCase and IFG for use in a method of treating a disorder related to a dysfunction in a GCase pathway comprising administering any of the compositions described herein. In another aspect is provided the use of a composition provided herein GCase and IFG in the manufacture of a medicament for a method of treating a dysfunction in a GCase pathway. In some embodiments, the method is effective to treat the disorder in a GCase pathway. In certain embodiments, the disorder is treated when one or more symptoms related to the dysfunction in a GCase pathway is ameliorated or reduced. In some embodiments, the composition is administered intravenously or subcutaneously. In some embodiments, the composition is administered subcutaneously, e.g. by subcutaneous injection. In some embodiments, the composition is administered twice weekly, once weekly, less often than once weekly, or once every other week.

In some embodiments, the disorder comprises a defect in GCase activity. In some embodiments, the defect in GCase activity comprises a decreased enzymatic activity. In some embodiments, the disorder comprises alpha-synuclein dysregulation. In some embodiments, the disorder is a lysosomal storage disease, e.g., Gaucher disease, Fabry disease, Pompe disease, a mucopolysaccharidoses, or multiple system atrophy. In some embodiments, the disorder is a neurodegenerative disorder, e.g., Parkinson disease, Alzheimer's disease, or Lewy body dementia.

In another aspect is provided a method of treating a dysfunction in a GCase pathway comprising administering to a subject in need thereof any of the compositions described herein. In some embodiments, the subject is human.

In some embodiments, the exposure, activity, or bioavailability of the GCase is increased upon administration of to a subject in need thereof any of the compositions comprising GCase and IFG described herein, e.g., relative to the exposure, activity, or bioavailability of an equivalent amount of GCase alone. In some embodiments, the exposure, activity, or bioavailability of the GCase in the spleen is increased. In some embodiments, the exposure, activity, or bioavailability of the GCase in the liver is increased. In some embodiments, the exposure, activity, or bioavailability of the GCase in the serum is increased. In some embodiments the composition is administered by IV. In some embodiments, the composition is administered subcutaneously.

In another aspect is provided a method of treating a dysfunction in a GCase pathway comprising administering to a subject a composition comprising a dosage of from 0.5 to 5.0 mg/kg bodyweight GCase and comprising IFG (including but not limited to the salts and crystalline forms described herein), e.g., wherein IFG is in at least about a 1, 1.25, 1.5, 2, 2.5, 3, 4, or 5-fold molar excess to the GCase. In some embodiments the composition is administered subcutaneously. In some embodiments, the IFG in the composition is administered in an amount which does not increase endogenous serum GCase activity when administered as a single agent, or more particularly, without co-administration of GCase.

In another aspect is provided a composition comprising a dosage from 0.5 to 5.0 mg/kg body weight GCase and comprising IFG (including but not limited to the salts and crystalline forms described herein), e.g., wherein IFG is in at least about a 1, 1.25, 1.5, 2, 2.5, 3, 4, or 5-fold molar excess to the GCase, for use in a method of treating a disorder related to a dysfunction in a GCase pathway. In another aspect is provided the use of a composition comprising a dosage from 0.5 to 5.0 mg/kg body weight GCase and comprising IFG (including but not limited to the salts and crystalline forms described herein), e.g., wherein IFG is in at least about a 1, 1.25, 1.5, 2, 2.5, 3, 4, or 5-fold molar excess to the GCase, in the manufacture of a medicament for a method of treating a dysfunction in a GCase pathway. In some embodiments, the method is effective to treat the disorder related to a dysfunction in a GCase pathway. In certain embodiments, the disorder is treated when one or more symptoms related to the dysfunction in a GCase pathway is ameliorated or reduced. In some embodiments, the composition is administered intravenously or subcutaneously. In some embodiments, the composition is administered subcutaneously, e.g. by subcutaneous injection. In some embodiments, the composition is administered twice weekly, once weekly, less often than once weekly, or once every other week.

In some embodiments, the composition for use in the disclosed methods comprises a dosage of from 0.8 to 4.0 mg/kg body weight GCase. In some embodiments, the composition comprises a dosage of from 1.0 to 3.0 mg/kg GCase. In some embodiments, the composition comprises a dosage of from 1.2 to 2.0 mg/kg GCase. In some embodiments, the composition comprises about 1.5 mg/kg GCase. In some embodiments, the composition comprises 1.5 mg/kg GCase. In some embodiments, the composition comprises 2.0 to 5.0 mg/kg GCase. In some embodiments, the composition comprises 2.25 to 4.5 mg/kg GCase. In some embodiments, the composition comprises 2.25 to 3.75 mg/kg GCase. In some embodiments, the composition comprises 3.5 to 5.0 mg/kg GCase.

In any of the preceding embodiments, the isofagomine compound used for stabilization of GCase in solution is isofagomine tartrate. In any of the preceding embodiments, the isofagomine compound used for stabilization of GCase in solution is isofagomine fumarate. In certain embodiments, the GCase is velaglucerase alfa.

Any of the preceding embodiments, wherein the isofagomine compound used for stabilization of GCase in solution is isofagomine tartrate. Any of the preceding embodiments, wherein the isofagomine compound used for stabilization of GCase in solution is isofagomine fumarate. In certain embodiments, the GCase is velaglucerase alfa.

In further embodiments of the compositions described herein, GCase is stable for 18 months, 20 months, 24 months, 26 months, 28 months, 30 months, 32 months, 34 months, 36 months, 38 months, 40 months, 42 months, 44 months, 46 months, or 48 months upon storage at ≤−65° C. In certain embodiments, GCase is stable for through 18 months when stored at the long-term storage condition of ≤−65° C. In certain embodiments, GCase is stable for through 30 months when stored at the long-term storage condition of ≤−65° C. In certain embodiments, GCase is stable for 8 months, 9 months, 10 months, 11 months, 12 months, 13 months, 14 months, 15 months, 16 months, 17 months, 18 months, 19 months, upon storage at −20±5° C. In certain embodiments, GCase is stable for 1 month, 2 months, 3 months, 4 months, 5 months, 6 months, upon storage at 5±3°.

In some embodiments of the composition for use in the disclosed methods, the IFG is in a 1 to 5 or a 1 to 10-fold molar ratio to the GCase. In some embodiments, the IFG is in a 2 to 10-fold molar ratio of GCase. In some embodiments, the IFG is in a 10 to 30-fold molar ratio to the GCase. In some embodiments, the IFG is in a 30 to 100-fold molar ratio to the GCase. In some embodiments, the IFG is in a 2.5 to 3.5-fold molar ratio to the GCase. In some embodiments, the IFG is in a 3-fold molar ratio to the GCase.

Any of the IFG and GCase/IFG formulations described herein may be administered to a patient. The GCase dose may be about 60 units/kg, or 60 units/kg, administered every other week. The GCase dose may be about 30 units/kg, or 30 units/kg, administered every week. Alternatively, the GCase dose may range from 30 to 80 units/kg administered every other week, from 40 to 70 units/kg administered every other week, from 50 to 80 units/kg administered every other week, from 45 to 65 units/kg administered every other week, from 40 to 60 units/kg administered every other week, from 35 to 55 units/kg administered every other week, from 30 to 50 units/kg administered every other week, from 45 to 65 units/kg administered every other week, from 50 to 70 units/kg administered every other week, from 55 to 75 units/kg administered every other week, from 60 to 80 units/kg administered every other week, from 55 to 65 units/kg administered every other week, from 45 to 55 units/kg administered every other week, from 35 to 45 units/kg administered every other week, or from 65 to 75 units/kg administered every other week. Alternatively, the GCase dose may range from 15 to 40 units/kg administered every week, from 20 to 35 units/kg administered every week, from 25 to 40 units/kg administered every week, from 22.5 to 32.5 units/kg administered every week, from 20 to 30 units/kg administered every week, from 17.5 to 22.5 units/kg administered every week, from 15 to 25 units/kg administered every week, from 22.5 to 32.5 units/kg administered every week, from 25 to 35 units/kg administered every week, from 22.5 to 37.5 units/kg administered every week, from 30 to 40 units/kg administered every week, from 27.5 to 32.5 units/kg administered every week, from 22.5 to 27.5 units/kg administered every week, from 17.5 to 22.5 units/kg administered every week, or from 32.5 to 37.5 units/kg administered every week. The GCase dose may be about 1.5 mg/kg, or 1.5 mg/kg, administered every other week. The GCase dose may be about 0.75 mg/kg, or 0.75 mg/kg, administered every week. Alternatively, the GCase dose may range from 0.75 to 2.0 mg/kg administered every other week, from 1.0 to 1.75 mg/kg administered every other week, from 1.25 to 2.0 mg/kg administered every other week, from 1.125 to 1.625 mg/kg administered every other week, from 1.0 to 1.5 mg/kg administered every other week, from 0.875 to 1.375 mg/kg administered every other week, from 0.75 to 1.25 mg/kg administered every other week, from 1.215 to 1.625 mg/kg administered every other week, from 1.25 to 1.75 mg/kg administered every other week, from 1.375 to 1.875 mg/kg administered every other week, from 1.5 to 2.0 mg/kg administered every other week, from 1.375 to 1.625 mg/kg administered every other week, from 1.125 to 1.375 mg/kg administered every other week, from 0.875 to 1.125 mg/kg administered every other week, or from 1.625 to 1.875 mg/kg administered every other week. Alternatively, the GCase dose may range from 0.375 to 1.0 mg/kg administered every week, from 0.5 to 0.875 mg/kg administered every week, from 0.625 to 1.0 mg/kg administered every week, from 0.5625 to 0.8125 mg/kg administered every week, from 0.5 to 0.75 mg/kg administered every week, from 0.4375 to 0.5625 mg/kg administered every week, from 0.375 to 0.625 mg/kg administered every week, from 0.5625 to 0.8125 mg/kg administered every week, from 0.625 to 0.875 mg/kg administered every week, from 0.5625 to 0.9375 mg/kg administered every week, from 0.75 to 1.0 mg/kg administered every week, from 0.6875 to 0.8125 mg/kg administered every week, from 0.5625 to 0.6875 mg/kg administered every week, from 0.4375 to 0.5625 mg/kg administered every week, or from 0.8125 to 0.9375 mg/kg administered every week.

Any of the IFG and GCase/IFG formulations described herein may be administered to a patient. The GCase dose may be about 90 to 180 units/kg, administered every other week. The GCase dose may be about 90 units/kg, or 90 units/kg, administered every week. Alternatively, the GCase dose may range from 90 to 150 units/kg administered every other week, from 110 to 160 units/kg administered every other week, from 120 to 180 units/kg administered every other week, from 120 to 150 units/kg administered every other week, from 90 to 120 units/kg administered every other week, from 100 to 130 units/kg administered every other week, from 110 to 140 units/kg administered every other week, from 120 to 150 units/kg administered every other week, from 130 to 160 units/kg administered every other week, from 140 to 170 units/kg administered every other week, or from 150 to 180 units/kg administered every other week. Alternatively, the GCase dose may range from 90 to 110 units/kg administered every other week, from 100 to 120 units/kg administered every other week, from 110 to 130 units/kg administered every other week, from 120 to 140 units/kg administered every other week, from 130 to 150 units/kg administered every other week, from 140 to 160 units/kg administered every other week, from 150 to 170 units/kg administered every other week, or from 160 to 180 units/kg administered every other week. The GCase dose may be about 2.25 to 4.5 mg/kg, administered every other week. Alternatively, the GCase dose may range from 2.25 to 3.75 mg/kg administered every other week, from 2.75 to 4.0 mg/kg administered every other week, from 3.0 to 4.5 mg/kg administered every other week, from 3.0 to 3.75 mg/kg administered every other week, from 2.25 to 3.0 mg/kg administered every other week, from 2.5 to 3.25 mg/kg administered every other week, from 2.75 to 3.5 mg/kg administered every other week, from 3.0 to 3.75 mg/kg administered every other week, from 3.25 to 4.0 mg/kg administered every other week, from 3.5 to 4.25 mg/kg administered every other week, or from 3.75 to 4.5 mg/kg administered every other week. Alternatively, the GCase dose may range from 2.25 to 2.75 mg/kg administered every other week, from 2.5 to 3.0 mg/kg administered every other week, from 2.75 to 3.25 mg/kg administered every other week, from 3.0 to 3.5 mg/kg administered every other week, from 3.25 to 3.75 mg/kg administered every other week, from 3.5 to 4.0 mg/kg administered every other week, from 3.75 to 4.25 mg/kg administered every other week, or from 4.0 to 4.5 mg/kg administered every other week.

Administration of the IFG and GCase/IFG compositions can be undertaken to treat a disorder related to a dysfunction in the GCase pathway, such as lysosomal storage diseases. Exemplary lysosomal storage diseases include Gaucher disease, Fabry disease, Pompe disease, mucopolysaccharidoses, and multiple system atrophy. The disorder may be a neurodegenerative disorder, e.g., Parkinson disease, Alzheimer's disease, or Lewy body dementia. Alternatively, the disorder may involve alpha-synuclein dysregulation.

In treating the disorder, the IFG and GCase/IFG compositions can be administered intravenously or subcutaneously. Subcutaneous administration includes subcutaneous injection. Various dosing schedules may be used to administer the compositions. For example, the composition may be administered once weekly, once every two weeks, once per month. The composition may be administered every three days, every four days, every five days, every six days, every eight days, every nine days, every 10 days, every 11 days, every 12 days, every 13 days, every 15 days, or every 16 days, for example. The frequency of administration may be changed throughout a course of treatment due to various factors.

Examples

The present invention is also described and demonstrated by way of the following examples. However, the use of these and other examples anywhere in the specification is illustrative only and in no way limits the scope and meaning of the invention or of any exemplified term. Likewise, the invention is not limited to any embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

X-ray powder diffraction pattern in the present disclosure is acquired by a Stoe Stadi P X-ray powder diffractometer. The parameters of the X-ray powder diffraction method of the present disclosure are as follows:

The measurements with this instrument were performed in transmission at a tube voltage of 40 kV and 40 mA tube power. A curved Ge monochromator allows testing with Cu-Kα1 radiation. The following parameters were set: 0.02° 2Θ step size, 12 s step time, 1.5-50.5° 2Θ scanning range, and 1° 2Θ detector step (detector mode in step scan). For a typical sample preparation about 10 mg of sample was placed between two acetate foils and mounted into a Stoe transmission sample holder. The sample was rotated during the measurement. All sample preparation and measurement was done in an ambient air atmosphere.

Example A: Purification of Isofagomine Free Base

Isofagomine free base obtained according to known methods, for example according to synthesis from D(−)-Arabinose as reported by Danishefsky et al. in Tetrahedron Letters 1990; 31(16), 2229, or as described in EP1860101B1, or according to synthesis from L-(−)-xylose, see Meloncelli, P. J. and Stick, R. V. *Aust. J. Chem.* 2006, vol. 59, pp 827-833. The obtained IFG free base was purified using a silica gel packed column and eluted with a solvent gradient consisting of dichloromethane, methanol and ammonium hydroxide, progressively increasing the polarity of the eluent until the IFG free base was eluted. Fractions were analyzed via TLC and then combined as appropriate, volatiles removed in vacuo to afford purified IFG free base, with less than 2% impurities, as determined by HPLC.

Example 1: Isofagomine Quinate

Solution 1 was prepared: a solution of quinic acid was prepared in about 4 volumes of methanol at room temperature.

Solution 2 was prepared: a solution of purified IFG (obtained in accordance with Example A) in methanol was prepared at room temperature. An equimolar amount of IFG is used relative to the quinic acid used in the preparation of solution 1.

Solution 2 was then added slowly to solution 1, whereupon crystalline material was formed. After agitation at room temperature, the slurry was filtered, and the resultant solid material was washed with methanol, deliquored and then dried in vacuo. A crystalline sample of the quinic acid salt of IFG SP245-QNC-P2 was obtained.

X-ray Powder Diffraction of the Obtained Isofagomine Quinate

The XRPD pattern of SP245-QNC-P2 obtained from the protocol described above in Example 1 is shown in FIG. 1 and tabulated below in Table 1 (vs=very strong, s=strong, m=medium, w=weak, vw=very weak intensity). Characteristic peaks are selected from the very strong, strong and medium diffraction peaks.

TABLE 1

XRPD Peaks for Isofagomine Quinate.
IFG Quinate

| Peak No. | Angle in °2Θ | d-value in Å | Qualitative intensity |
|---|---|---|---|
| 1 | 9.5 | 9.3 | m |
| 2 | 11.9 | 7.5 | w |
| 3 | 13.2 | 6.7 | w |
| 4 | 14.4 | 6.2 | w |
| 5 | 15.0 | 5.90 | s |
| 6 | 17.4 | 5.08 | vs |
| 7 | 18.1 | 4.90 | s |
| 8 | 19.0 | 4.67 | w |
| 9 | 20.3 | 4.37 | s |
| 10 | 21.5 | 4.14 | w |
| 11 | 22.0 | 4.03 | w |
| 12 | 22.7 | 3.92 | w |
| 13 | 23.8 | 3.74 | m |
| 14 | 24.8 | 3.59 | s |
| 15 | 25.4 | 3.50 | m |
| 16 | 26.5 | 3.36 | w |
| 17 | 27.0 | 3.30 | w |
| 18 | 27.4 | 3.25 | w |
| 19 | 27.8 | 3.21 | w |
| 20 | 28.7 | 3.11 | w |
| 21 | 30.5 | 2.92 | w |
| 22 | 31.4 | 2.84 | w |
| 23 | 32.0 | 2.80 | w |

Raman Spectroscopy of Isofagomine Quinate

Figure 2A:
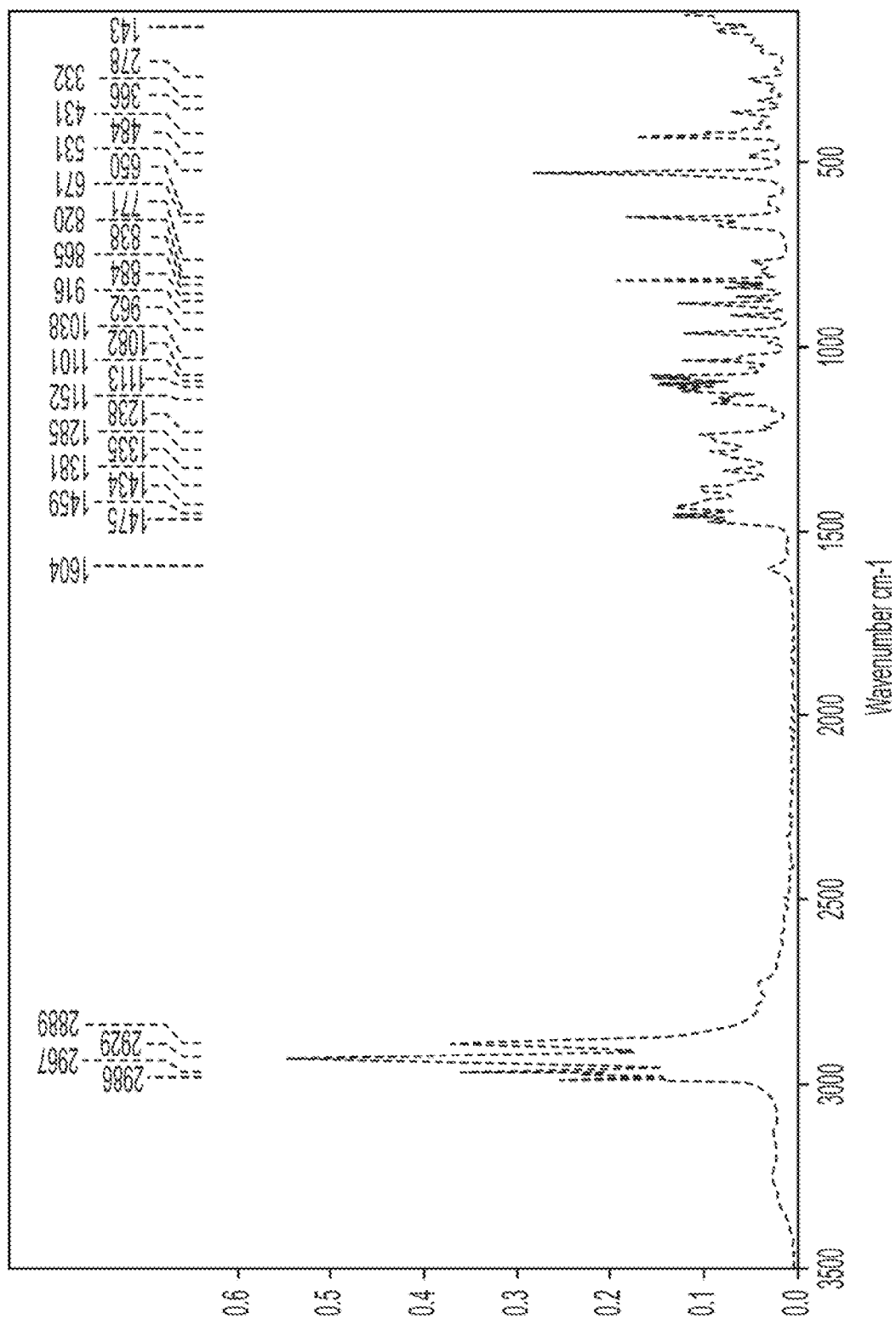
FIG. 2 is a characteristic FT-Raman spectrum of isofagomine quinate. Spectrum from 200 to 3500 cm−1 (FIG. 2a) and fingerprint region of the spectrum from 200 to 2000 cm−1 (FIG. 2B).
Figure 2B:
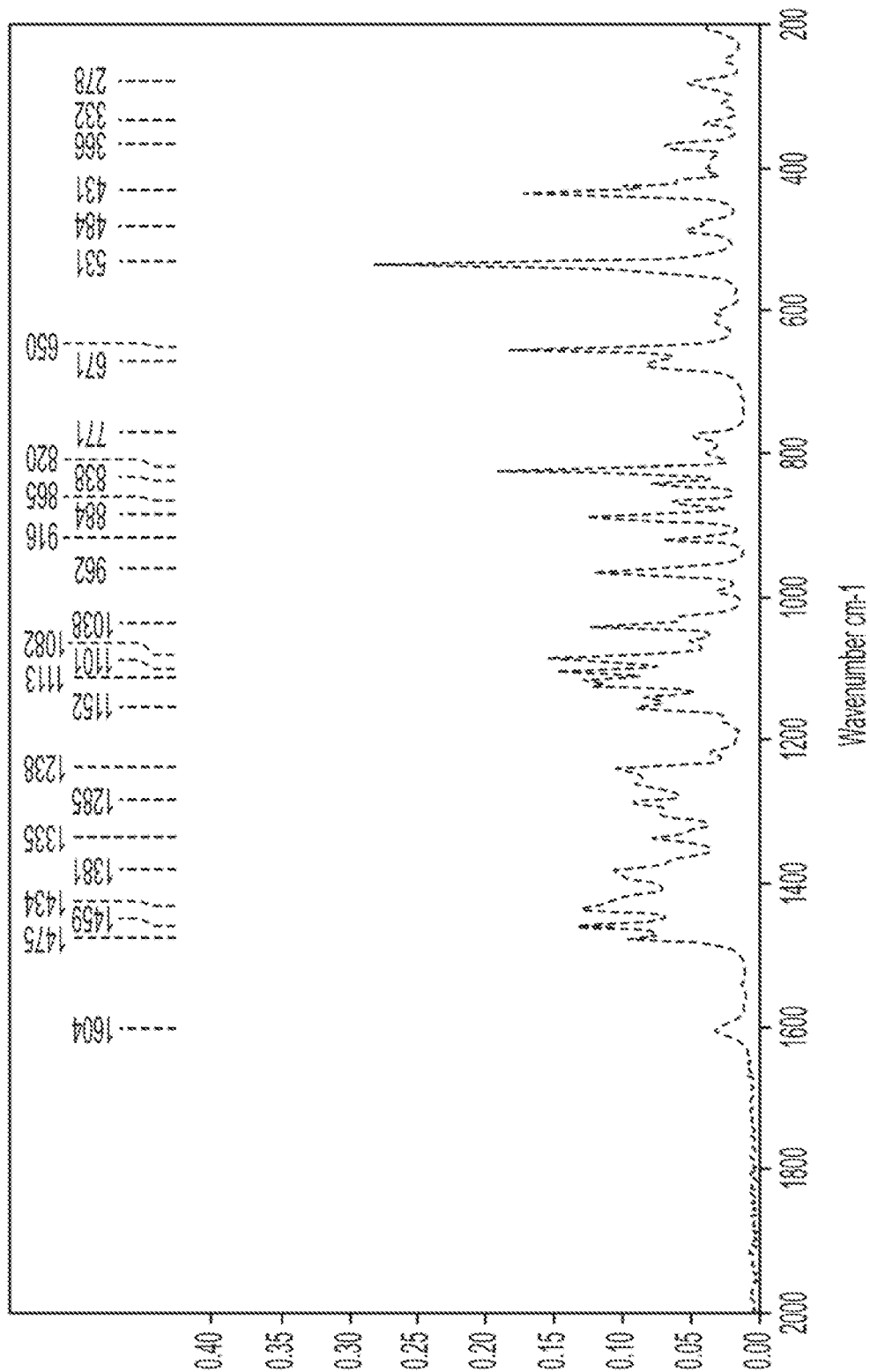

Raman spectrum was recorded for SP245-QNC-P2 and is presented in FIG. 2. An overview of the FT-Raman spectrum from 200 to 3500 cm$^{-1}$ (FIG. 2A) and fingerprint region of the FT-Raman spectrum from 200 to 2000 cm$^{-1}$ (FIG. 2B)

$^{1}$H-NMR Spectroscopy of Isofagomine Quinate

Figure 3:
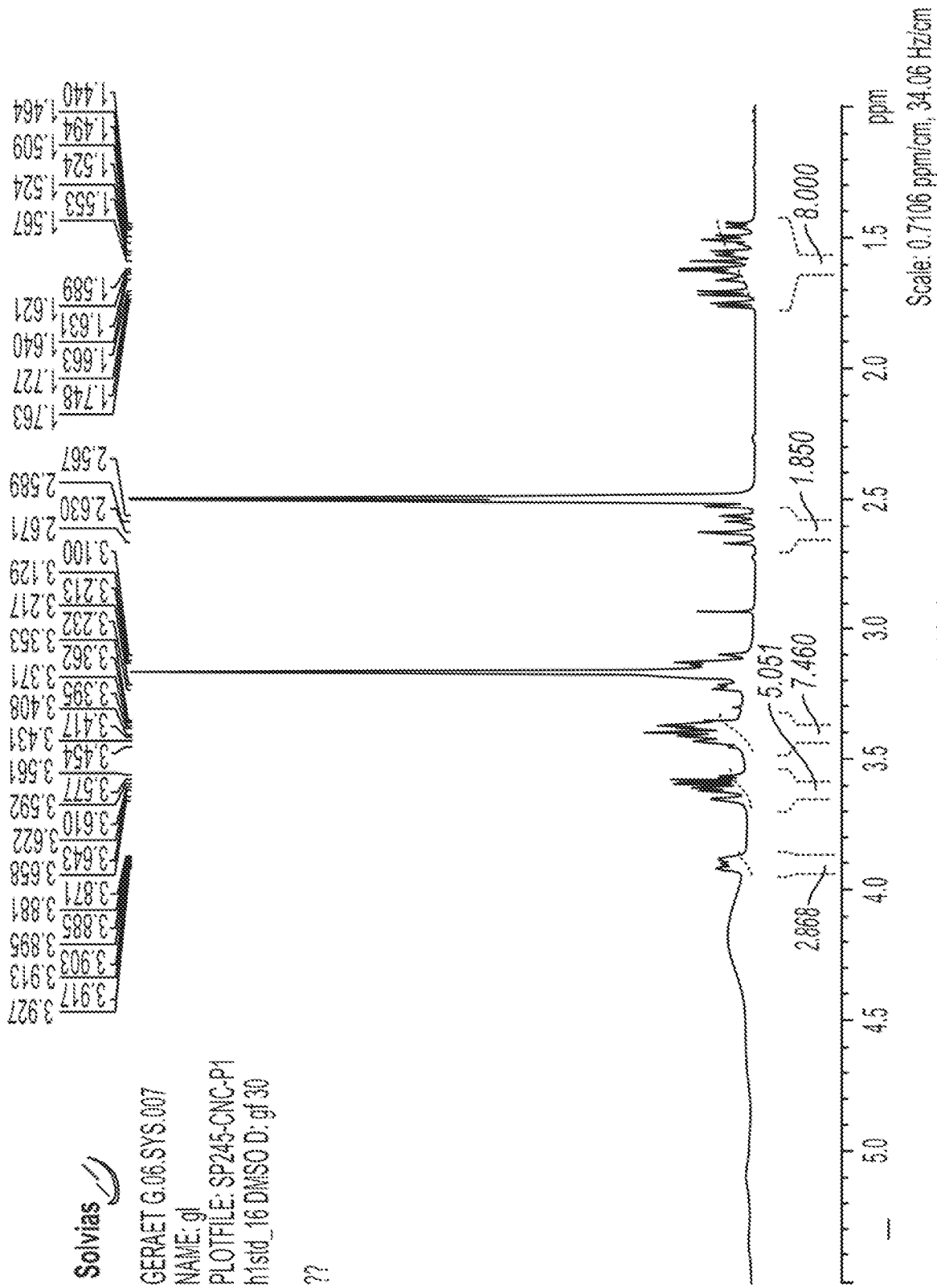
FIG. 3 is a characteristic 1H NMR spectrum of isofagomine quinate.

The $^{1}$H-NMR spectrum of SP245-QNC-P2 was recorded in DMSO-d$_{6}$ and is presented in FIG. 3. The spectrum is consistent with a 1 to 1 salt formation.

TG-FTIR of Isofagomine Quinate

Figure 4:
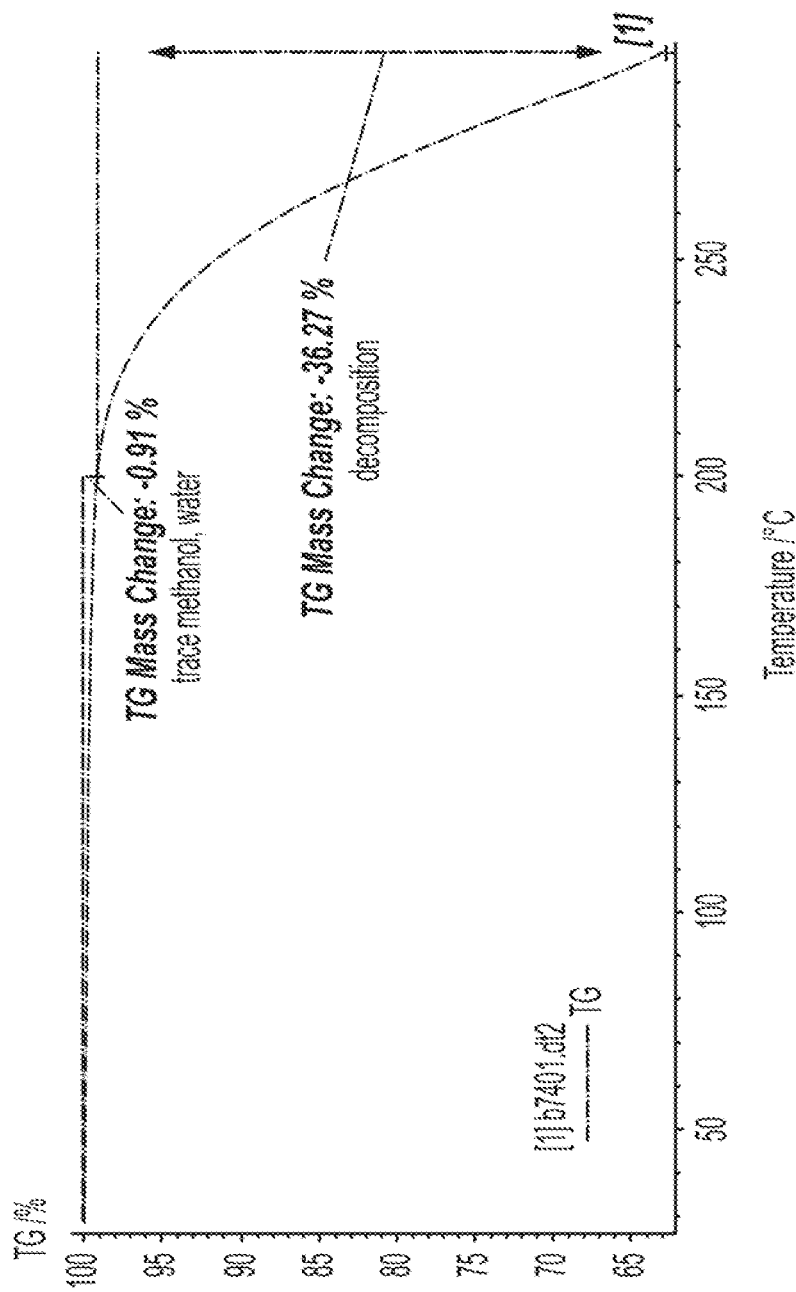
FIG. 4 is a TGA thermogram of a TG-IR analysis of isofagomine quinate.

TG-FTIR measurements were conducted and revealed less than 1% mass loss between 25° C. and 200° C. The obtained crystalline form SP245-QNC-P2 is anhydrous/non-solvated. The TG-FTIR thermogram is presented in FIG. 4 and shows a mass loss of 0.9% that corresponds to water and a trace of methanol. Decomposition is observable above 200° C.

Differential Scanning Calorimetry of Isofagomine Quinate

Figure 5:
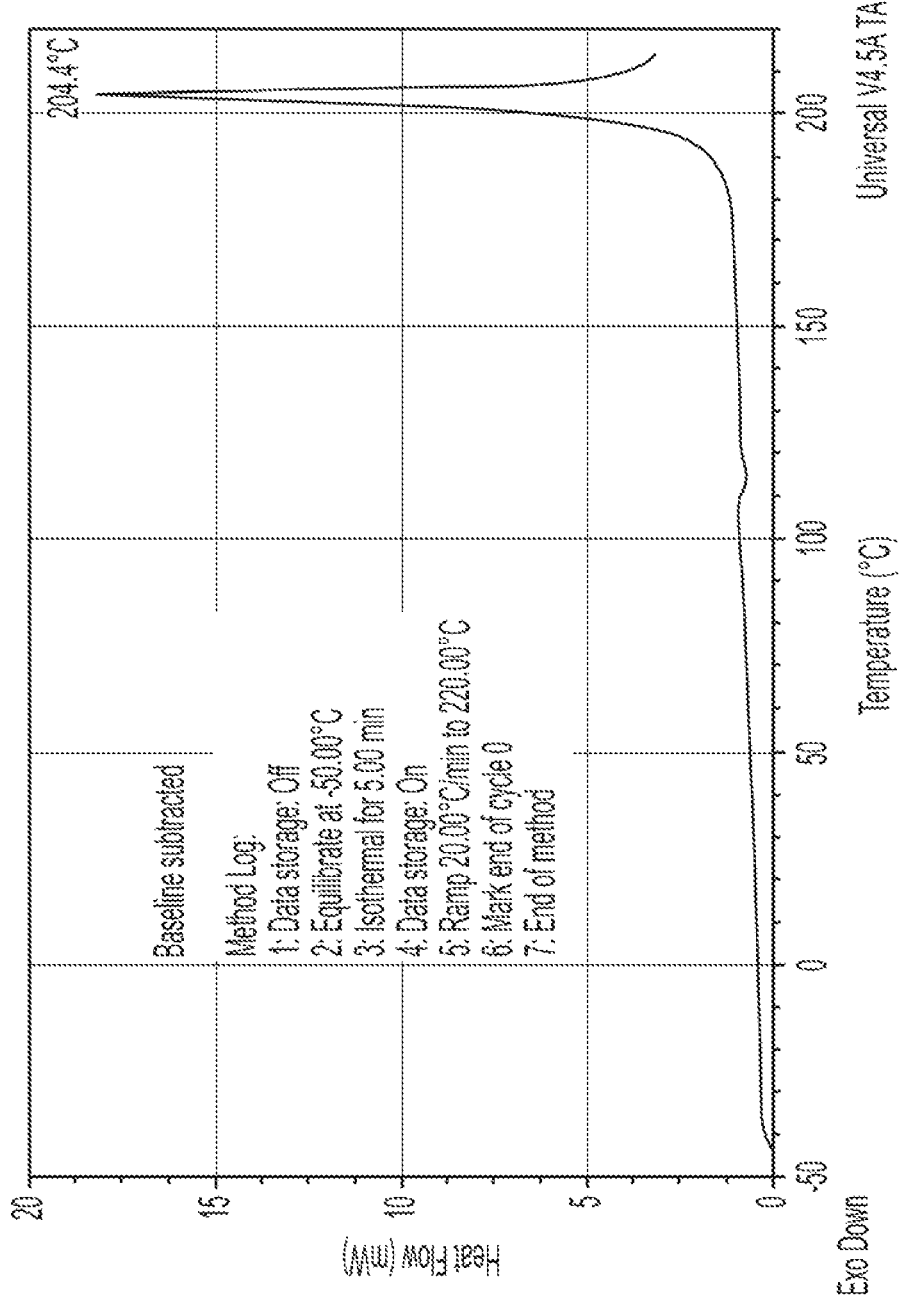
FIG. 5 is a differential scanning calorimetry (DSC) analysis of isofagomine quinate.

Differential scanning calorimetry revealed a melting peak temperature at 204.4° C. (see FIG. 5). However, the decomposition started already before the end of the melting process and the enthalpy of fusion could not be determined.

Dynamic Vapor Sorption of Isofagomine Quinate

Figure 6A:
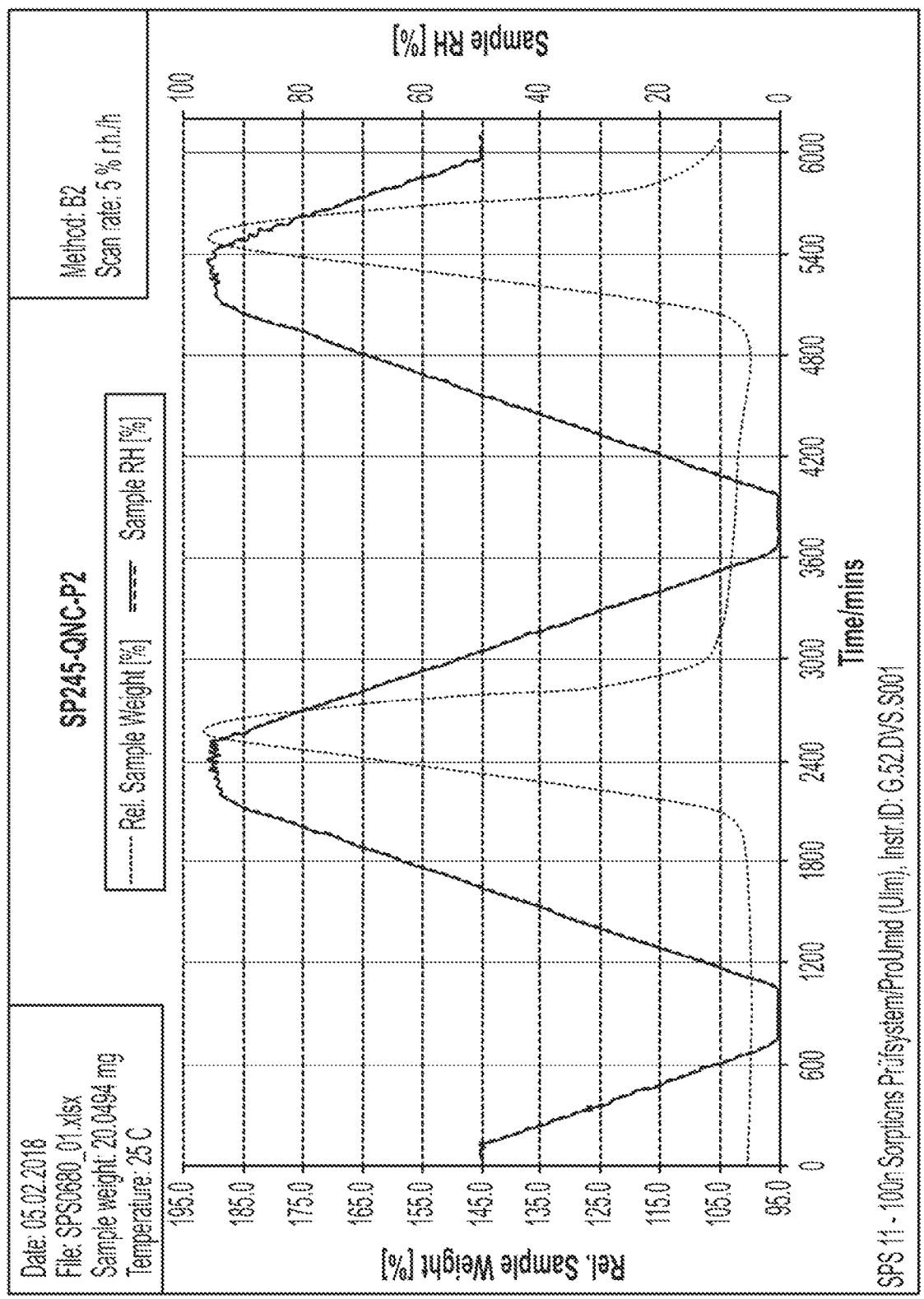
FIG. 6 is a dynamic vapor sorption (DVS) isotherm of isofagomine quinate.
Figure 6B:
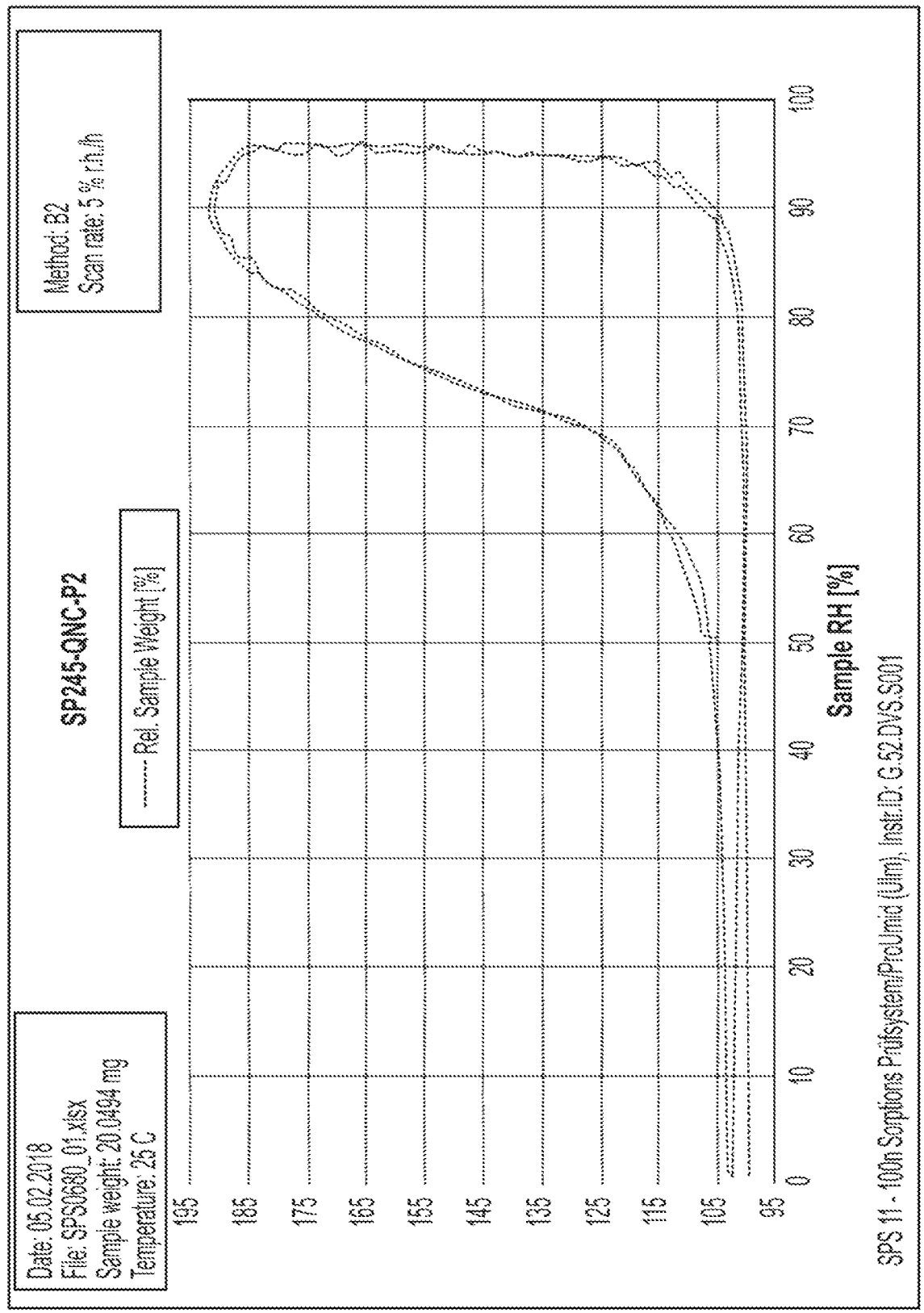

The behavior of the IFG quinate salt, sample SP245-QNC-P2, was investigated in the presence of variable water vapor pressure using DVS measurement. The result from the DVS test is presented in FIG. 6 and FIG. 6B as the DVS isotherm of sample SP245-QNC-P2: the change of relative sample weight (red curve) and relative humidity (blue curve) as a function of time.

No significant loss in weight was observed when decreasing the relative humidity from 50 to 0%. Furthermore, no gain in weight was observed when increasing the RH from 0 to 80%, then 20% mass gain was observed until 95% RH and additional 70% weight gain upon storage at 95%. The SP245-QNC-P2 salt prepared in example 1 is hygroscopic at high relative humidity; i.e., above about 80% RH. The sample recovered after DVS measurement was submitted to XRPD and no form change was observed but a gain of crystallinity was noted.

Identity of Isofagomine Quinate by Elemental Composition Analysis

The chemical identity of the IFG quinate s alt SP245-QNC-P2 was verified by elemental composition analysis using CHNO content determinations and TG-FTIR for the water and solvent content. The obtained results are summarized in Table 2 providing the result from CHNO content analysis for sample SP245-QNC-P2 compared with the theoretical composition of a (1:1) solvent and water-free salt with a molecular mass of 339.34 g/mol and the formula C13H25NO9. The results from the CHNO analysis constitute a very good match with the theoretical content of a solvent and water-free quinic salt.

TABLE 2

Elemental Analysis of Isofagomine Quinate

| Element | SP245-QNC-P2 | Expected content for a solvent and water-free mono-quinic salt |
|---|---|---|
| C | 45.7% | 46.01% |
| H | 7.3% | 7.4% |
| N | 4.1% | 4.1% |
| O | 42.3% | 42.4% |
| Water/solvent by TG-FTIR | <1% | 0% |

Example 2: Isofagomine Fumarate

Solution 1 was prepared: a solution of fumaric acid was prepared in about 4 volumes of methanol at room temperature.

Solution 2 was prepared: a solution of purified IFG (obtained in accordance with Example A) in about 4 volumes of methanol was prepared at room temperature. An equimolar amount of IFG is used relative to the fumaric acid used in the preparation of solution 1.

Solution 2 was then added slowly to solution 1, whereupon crystalline material was formed. After agitation at room temperature, the slurry was filtered, and the resultant solid material was washed with methanol solvent, deliquored and then dried in vacuo. A crystalline sample of the fumaric acid salt of IFG SP245-FUM-P4 was obtained.

X-ray Powder Diffraction of Isofagomine Fumarate

Figure 7:
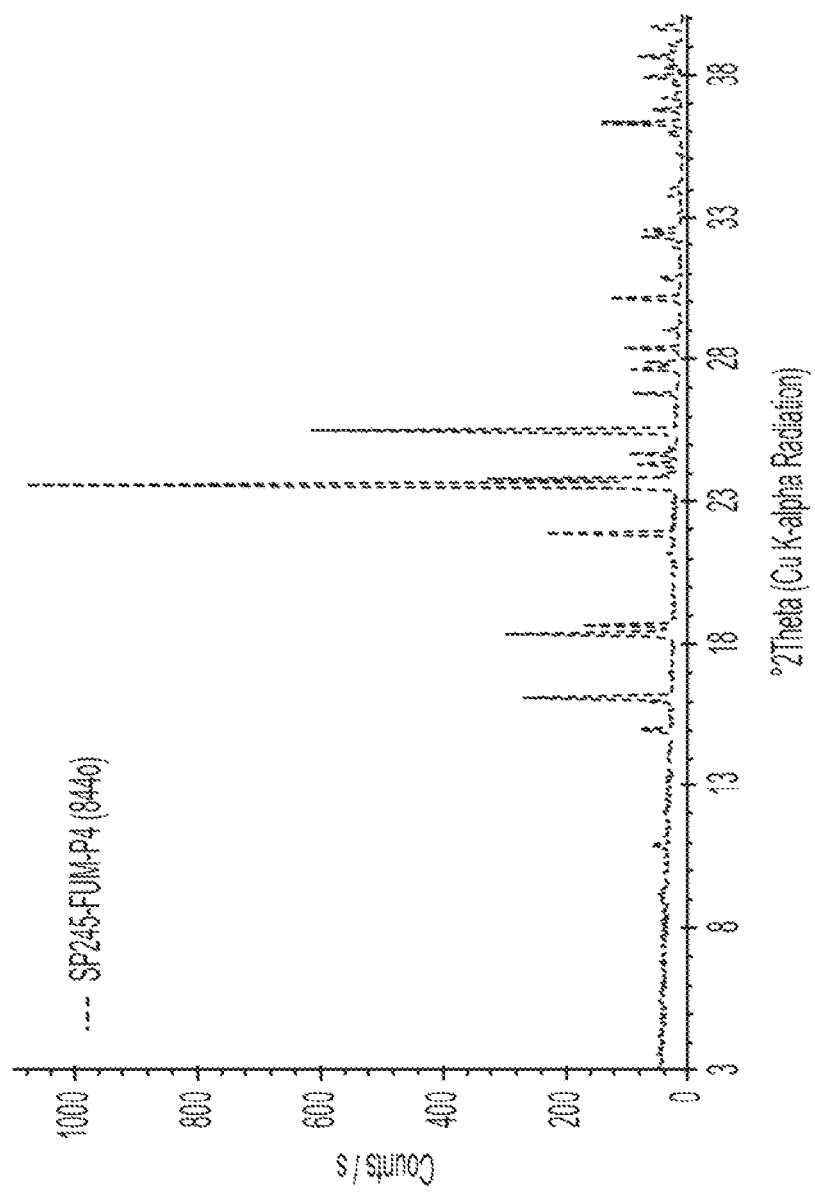
FIG. 7 is a characteristic XRPD spectrum of isofagomine fumarate.

The XRPD pattern of SP245-FUM-P4 obtained from the protocol described above in Example 2 is shown in FIG. 7 and tabulated below in Table 3 (vs=very strong, s=strong, m=medium, w=weak, vw=very weak intensity). Characteristic peaks are selected from the very strong, strong and medium diffraction peaks.

TABLE 3

XRPD Peaks for Isofagomine Fumarate
IFG Fumarate

| Peak No. | Angle in °2Θ | d-value in Å | Qualitative |
|---|---|---|---|
| 1 | 9.1 | 9.7 | vw |
| 2 | 10.9 | 8.1 | vw |
| 3 | 14.9 | 5.92 | w |
| 4 | 16.1 | 5.50 | m |
| 5 | 18.3 | 4.84 | m |
| 6 | 18.6 | 4.75 | m |
| 7 | 21.2 | 4.19 | vw |
| 8 | 21.6 | 4.11 | vw |
| 9 | 21.9 | 4.06 | m |
| 10 | 23.6 | 3.77 | vs |
| 11 | 23.8 | 3.74 | m |
| 12 | 24.0 | 3.70 | vw |
| 13 | 24.3 | 3.66 | w |
| 14 | 24.7 | 3.61 | w |
| 15 | 25.0 | 3.57 | vw |
| 16 | 25.5 | 3.49 | s |
| 17 | 26.2 | 3.40 | vw |
| 18 | 26.8 | 3.33 | w |
| 19 | 27.7 | 3.22 | w |
| 20 | 27.9 | 3.20 | w |
| 21 | 28.4 | 3.14 | w |
| 22 | 29.0 | 3.08 | vw |
| 23 | 29.6 | 3.02 | vw |
| 24 | 30.2 | 2.96 | w |
| 25 | 30.9 | 2.90 | vw |
| 26 | 31.4 | 2.85 | vw |
| 27 | 32.0 | 2.80 | vw |

Raman Spectroscopy of Isofagomine Fumarate

Figure 8A:
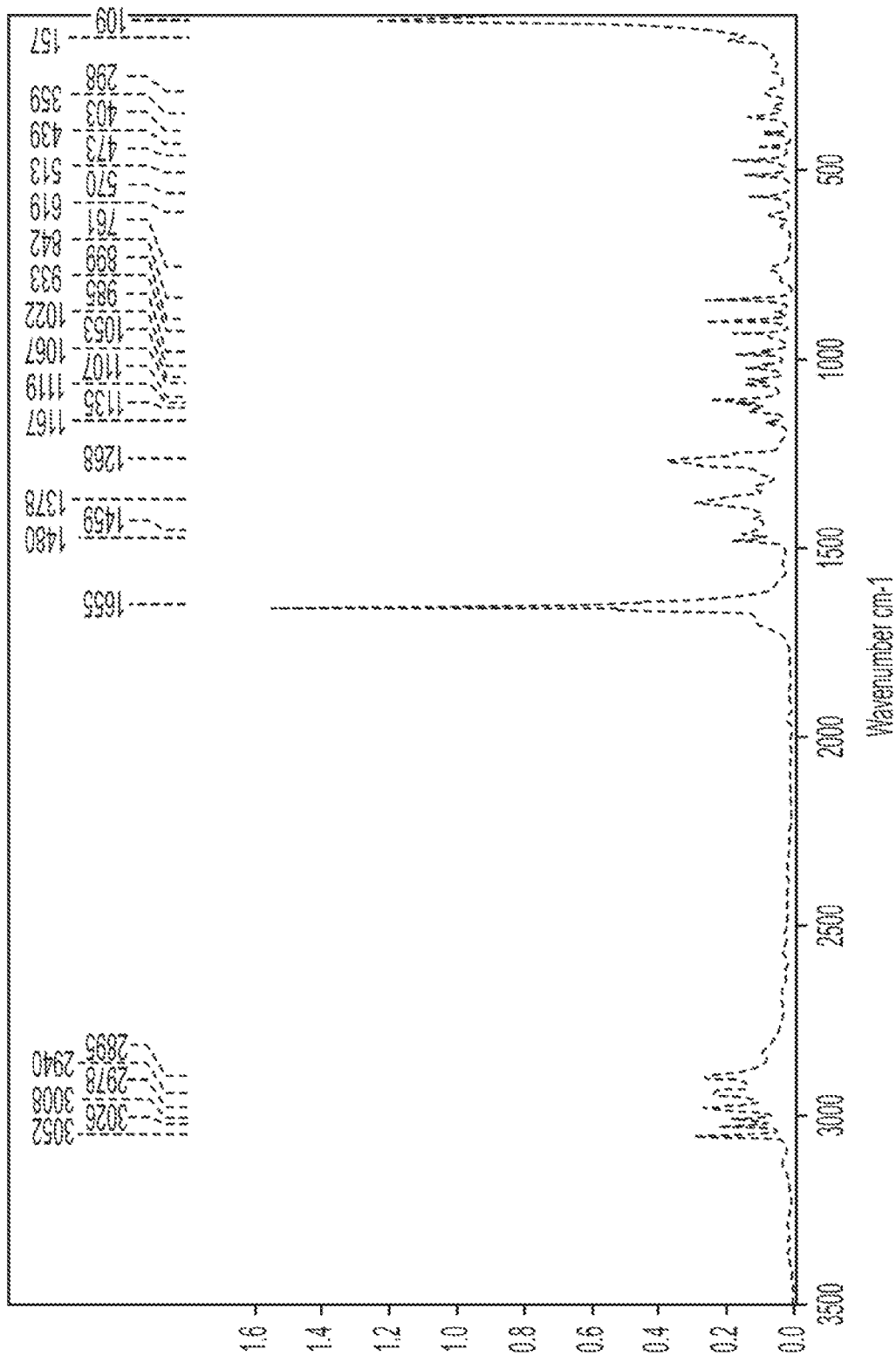
FIG. 8 is a characteristic FT-Raman spectrum isofagomine fumarate: spectrum from 200 to 3500 cm−1 (FIG. 8A) and fingerprint region of the spectrum from 200 to 2000 cm−1 (FIG. 8B).
Figure 8B:
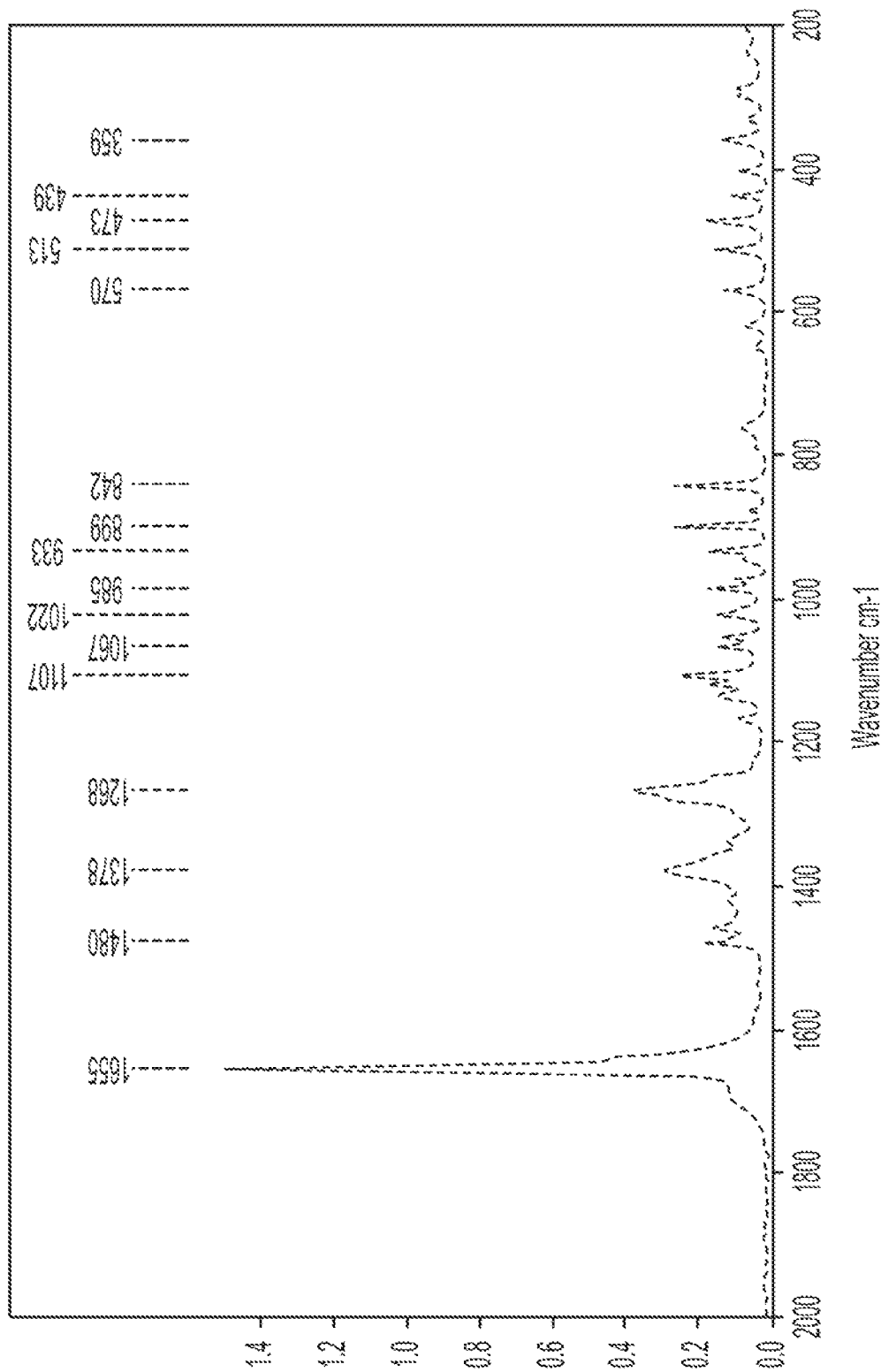

Raman spectrum was recorded for SP245-FUM-P4 and is presented in FIG. 8. An overview of the FT-Raman spectrum from 200 to 3500 cm$^{-1}$ (FIG. 8A) and fingerprint region of the FT-Raman spectrum from 200 to 2000 cm-1 (FIG. 8B3)

$^1$H-NMR Spectroscopy of Isofagomine Fumarate

Figure 9:
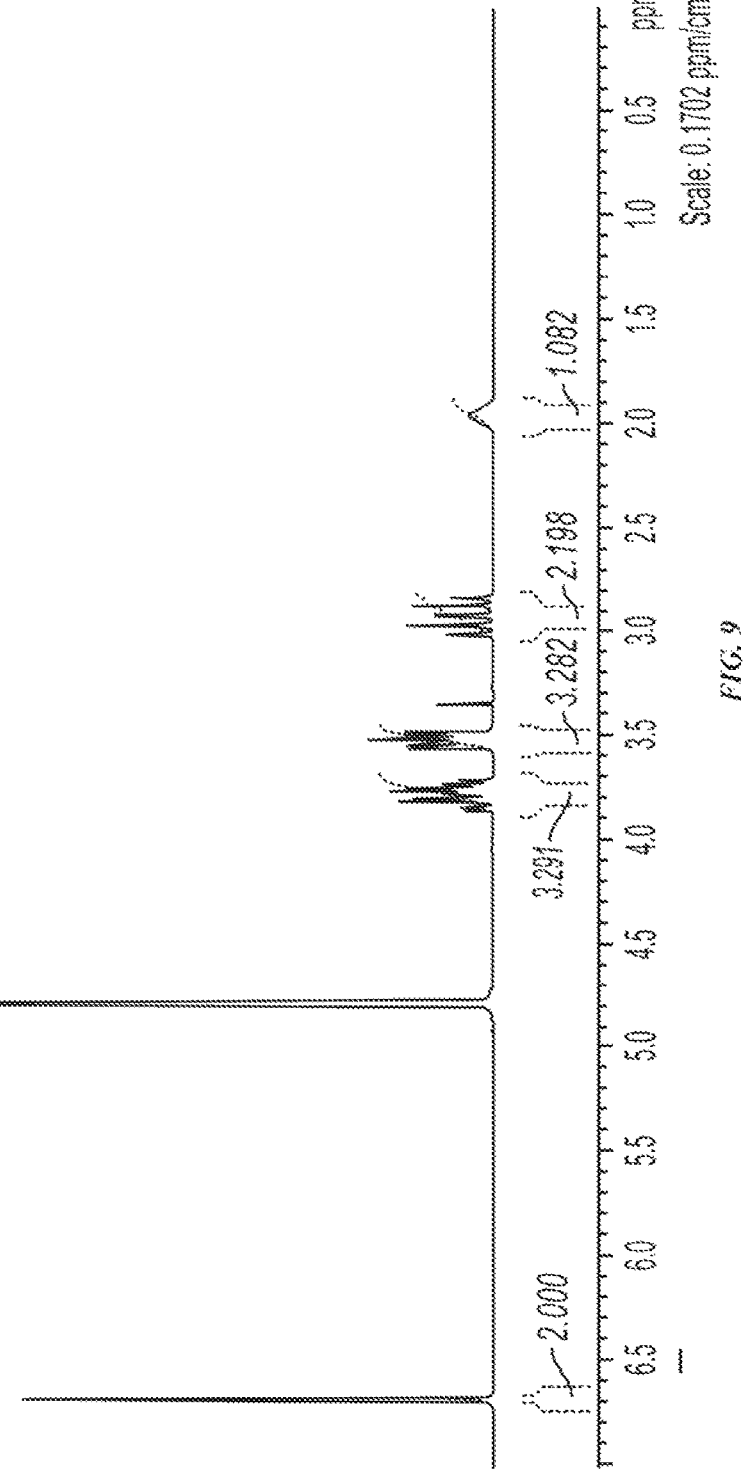
FIG. 9 is a characteristic 1H NMR spectrum of isofagomine fumarate.

The $^1$H-NMR spectrum of SP245-FUM-P4 was recorded in D$_2$O and is presented in FIG. 9. The spectrum is consistent with a 1 to 1 salt formation.

TG-FTIR of Isofagomine Fumarate

Figure 10:
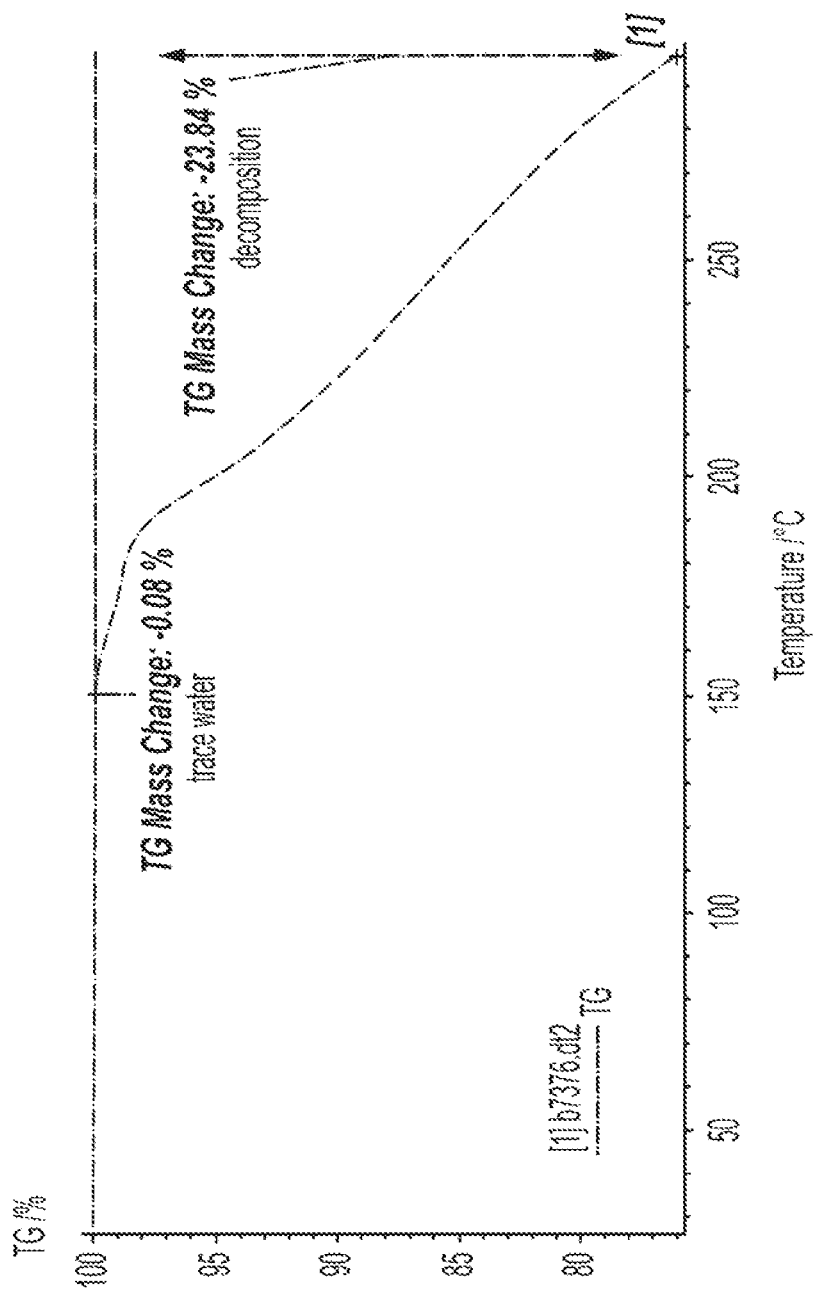
FIG. 10 is a TGA thermogram of a TG-IR analysis of isofagomine fumarate.

The TG-FTIR thermogram of SP245-FUM-P4 is presented in FIG. 10 and shows no considerable mass loss between 25° C. and 150° C. The fumarate salt is a solvent and water-free form. Decomposition is observable above 150° C.

Differential Scanning Calorimetry of Isofagomine Fumarate

Figure 11:
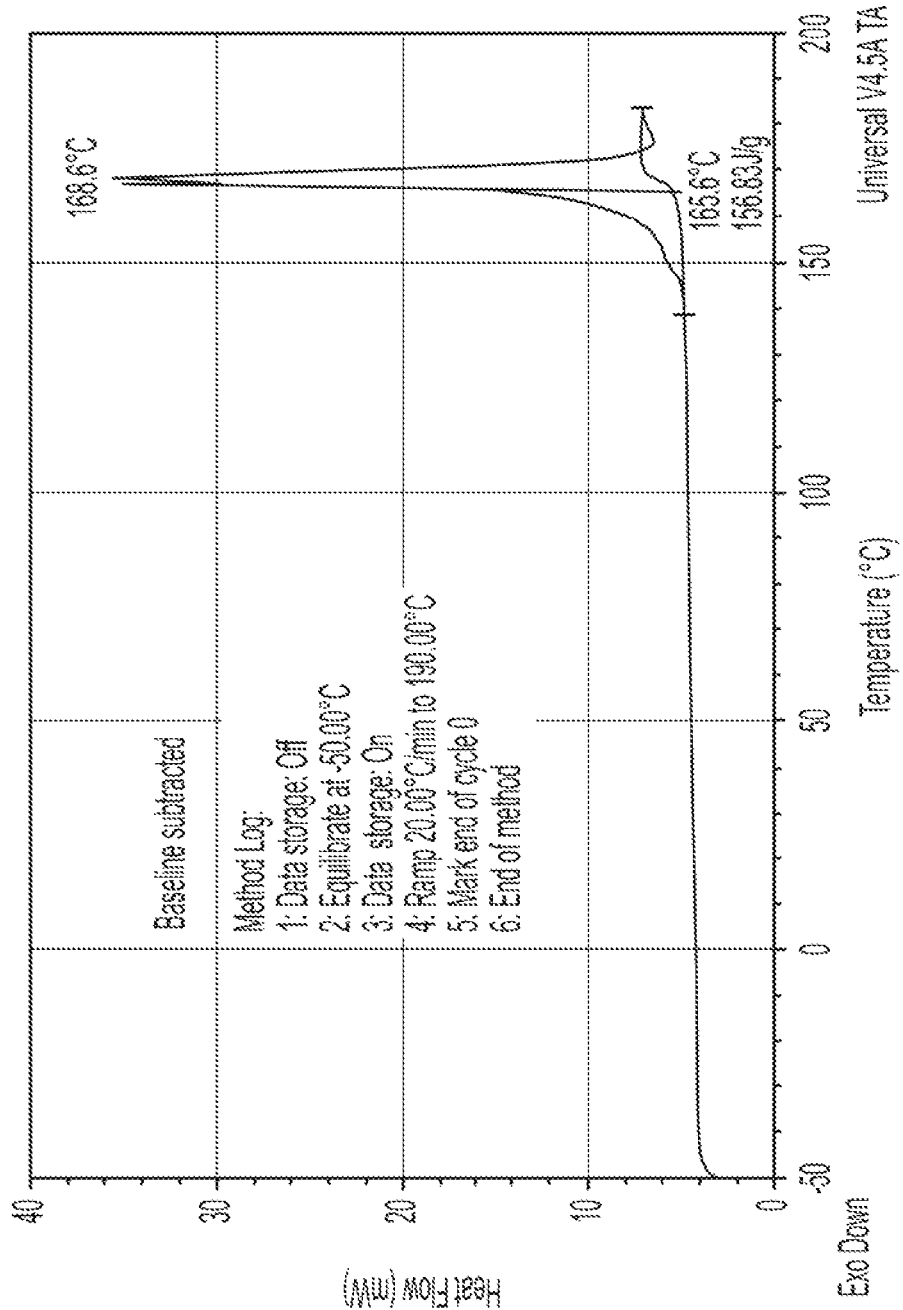
FIG. 11 is a DSC analysis of isofagomine fumarate.

Differential scanning calorimetry of SP245-FUM-P4 revealed a melting peak temperature at 168.6° C., an onset temperature of 165.6° C. with an enthalpy of fusion of 157 J/g (see FIG. 11).

Dynamic Vapor Sorption of Isofagomine Fumarate

Figure 12A:
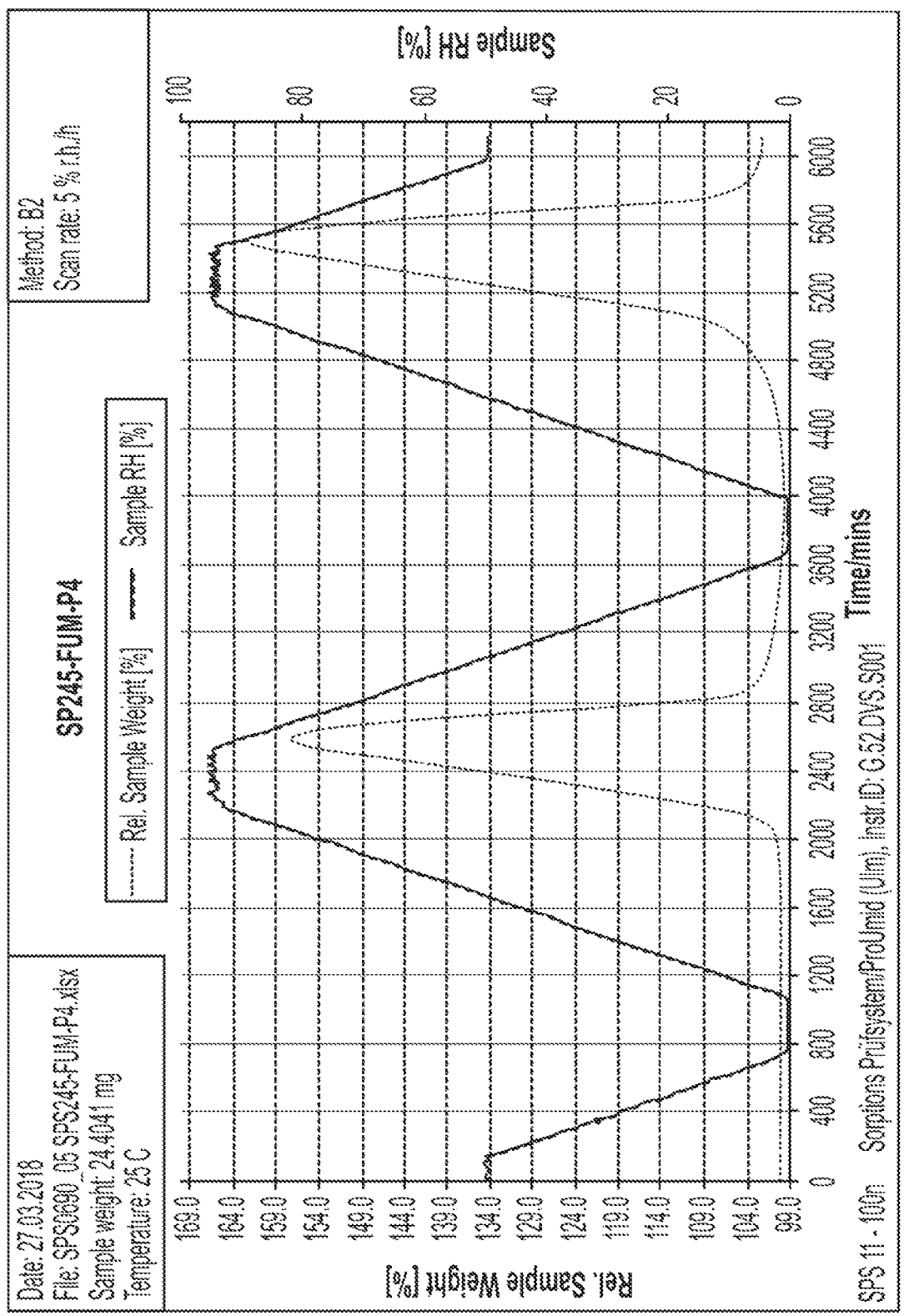
FIG. 12 is a DVS isotherm of isofagomine fumarate.
Figure 12B:
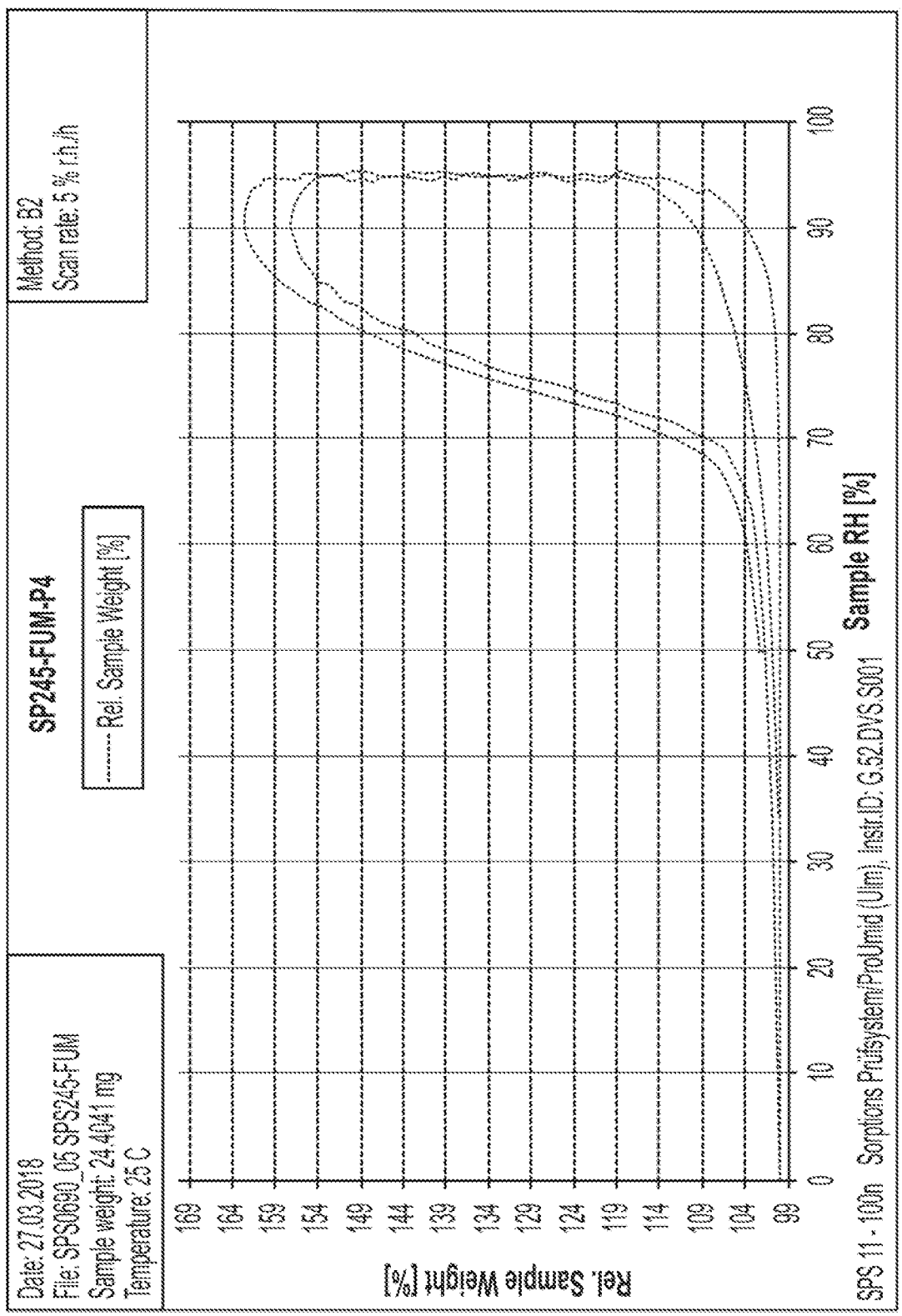

The effect of changes in relative humidity on the IFG fumarate sample SP245-FUM-P4 was studied using DVS. FIG. 12 shows the DVS isotherm of sample SP245-FUM-P4: the change of relative sample weight (red curve) and relative humidity (blue curve) as a function of time (FIG. 12A) and the change of relative sample weight as a function of relative humidity (FIG. 12B).

No significant weight loss (<1 weight %) was observed when decreasing the relative humidity from 50 to 0% RH and then no considerable gain in sample mass was observed when increasing the RH from 0 to 80% RH. 11% weight gain was observed when scanning up to 95% RH and an additional 47% weight gain occurred upon five hours storage at 95%. During the second cycle, a gain in weight from 5% was observed at 95% RH compared to the first cycle. The IFG fumarate salt is hygroscopic at relative humidities above about 80%.

The crystalline substance recovered after DVS measurement was analyzed by XRPD and correspond to the sample SP245-FUM-P4 used as starting material for the DVS test.

Identity of Isofagomine Fumarate by Elemental Composition Analysis

The chemical identity of the IFG fumarate salt SP245-FUM-P4 was verified by elemental composition analysis using CHNO contents determinations and TG-FTIR for the water and solvent content. The obtained results are summarized in Table 4—CHNO content analysis for sample SP245-FUM-P4 compared with the theoretical composition of a (1:1) solvent and water-free salt with a molecular mass of 263.35 g/mol and the formula C10H17NO7. The results from the CHNO analysis show an excellent match with the theoretical content of a solvent and water-free fumarate salt.

TABLE 4

Elemental Analysis of Isofagomine Fumarate

| Element | SP245-FUM-P4 | Expected content for a solvent and water-free mono-fumarate salt |
|---|---|---|
| C | 45.5% | 45.6% |
| H | 6.4% | 6.5% |
| N | 5.3% | 5.3% |
| O | 42.4% | 42.5% |
| Water by TG-FTIR | <0.1% | 0% |

Example 3: Isofagomine Oxalate

Solution 1 was prepared: a solution of oxalic acid was prepared in about 2.5 volumes of methanol at room temperature.

Solution 2 was prepared: a solution of purified IFG (obtained in accordance with Example A) in methanol was prepared at room temperature in about 2.6 volumes of methanol. An equimolar amount of IFG is used relative to the oxalic acid used in the preparation of solution 1.

Solution 2 was then added slowly to solution 1, whereupon crystalline material was formed. After agitation at room temperature, the slurry was filtered, and the resultant solid material was washed with methanol, deliquored and then dried in vacuo. A crystalline sample of the quinic acid salt of IFG oxalate SP245-OXA-P1 was obtained.

X-ray Powder Diffraction of Isofagomine Oxalate

Figure 13:
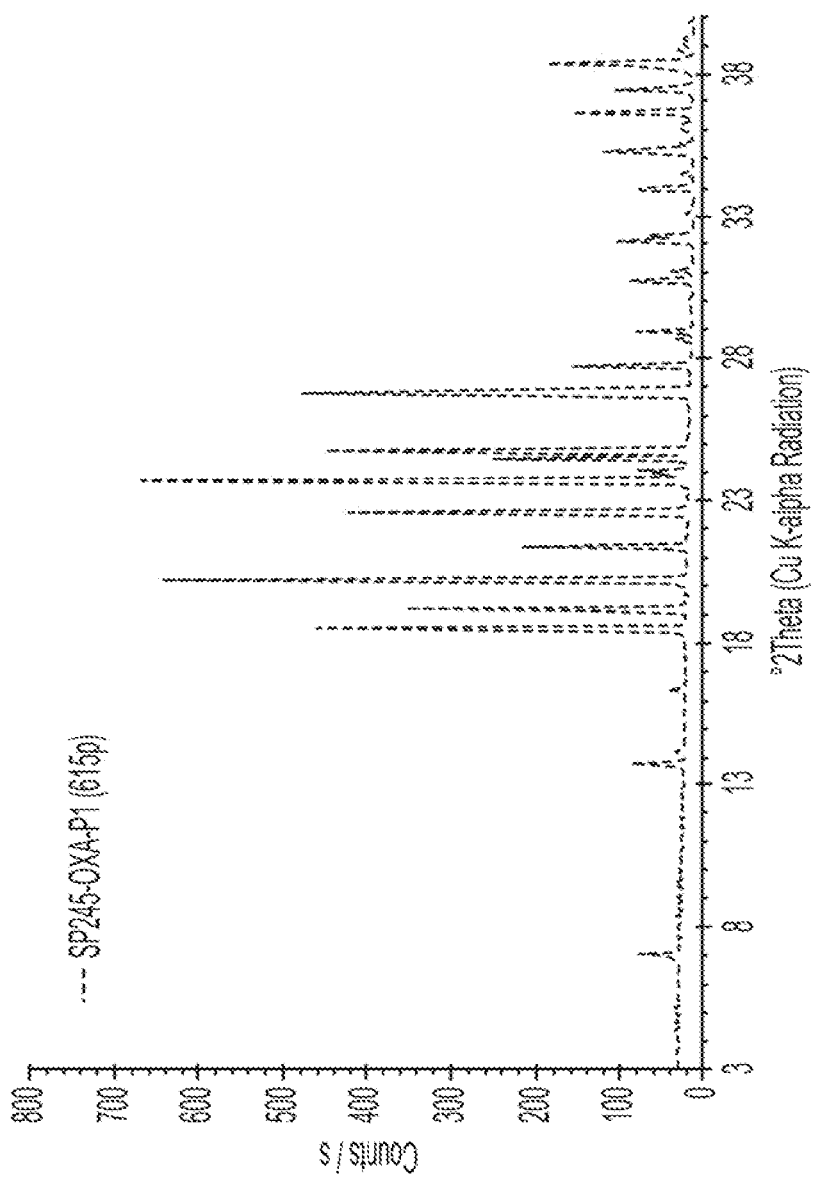
FIG. 13 is a characteristic XRPD spectrum of isofagomine oxalate.

The XRPD pattern of SP245-OXA-P1 obtained from the protocol described above in Example 1 is shown in is shown in FIG. 13 and tabulated in Table 5, below (vs=very strong, s=strong, m=medium, w=weak, vw=very weak intensity). Characteristic peaks are selected from the very strong, strong and medium diffraction peaks.

TABLE 5

XRPD Peaks for Isofagomine Oxalate IFG Oxalate

| Peak No. | Angle in °2Θ | d-value in Å | Qualitative |
|---|---|---|---|
| 1 | 7.1 | 12.5 | w |
| 2 | 13.8 | 6.4 | w |
| 3 | 14.2 | 6.2 | w |
| 4 | 16.4 | 5.41 | w |
| 5 | 18.5 | 4.79 | s |
| 6 | 19.2 | 4.61 | s |
| 7 | 20.2 | 4.38 | vs |
| 8 | 21.4 | 4.15 | s |
| 9 | 22.6 | 3.93 | s |
| 10 | 23.7 | 3.75 | vs |
| 11 | 24.1 | 3.70 | w |
| 12 | 24.5 | 3.63 | s |
| 13 | 24.8 | 3.59 | s |
| 14 | 26.8 | 3.32 | s |
| 15 | 27.8 | 3.21 | m |
| 16 | 28.7 | 3.11 | vw |
| 17 | 29.0 | 3.08 | w |
| 18 | 30.1 | 2.97 | vw |
| 19 | 30.7 | 2.91 | w |
| 20 | 31.1 | 2.87 | w |
| 21 | 32.2 | 2.78 | m |
| 22 | 32.4 | 2.76 | w |
| 23 | 34.0 | 2.64 | w |
| 24 | 35.3 | 2.54 | m |
| 25 | 36.6 | 2.45 | m |
| 26 | 37.4 | 2.40 | m |
| 27 | 38.4 | 2.34 | m |

Raman Spectroscopy of Isofagomine Oxalate

Figure 14A:
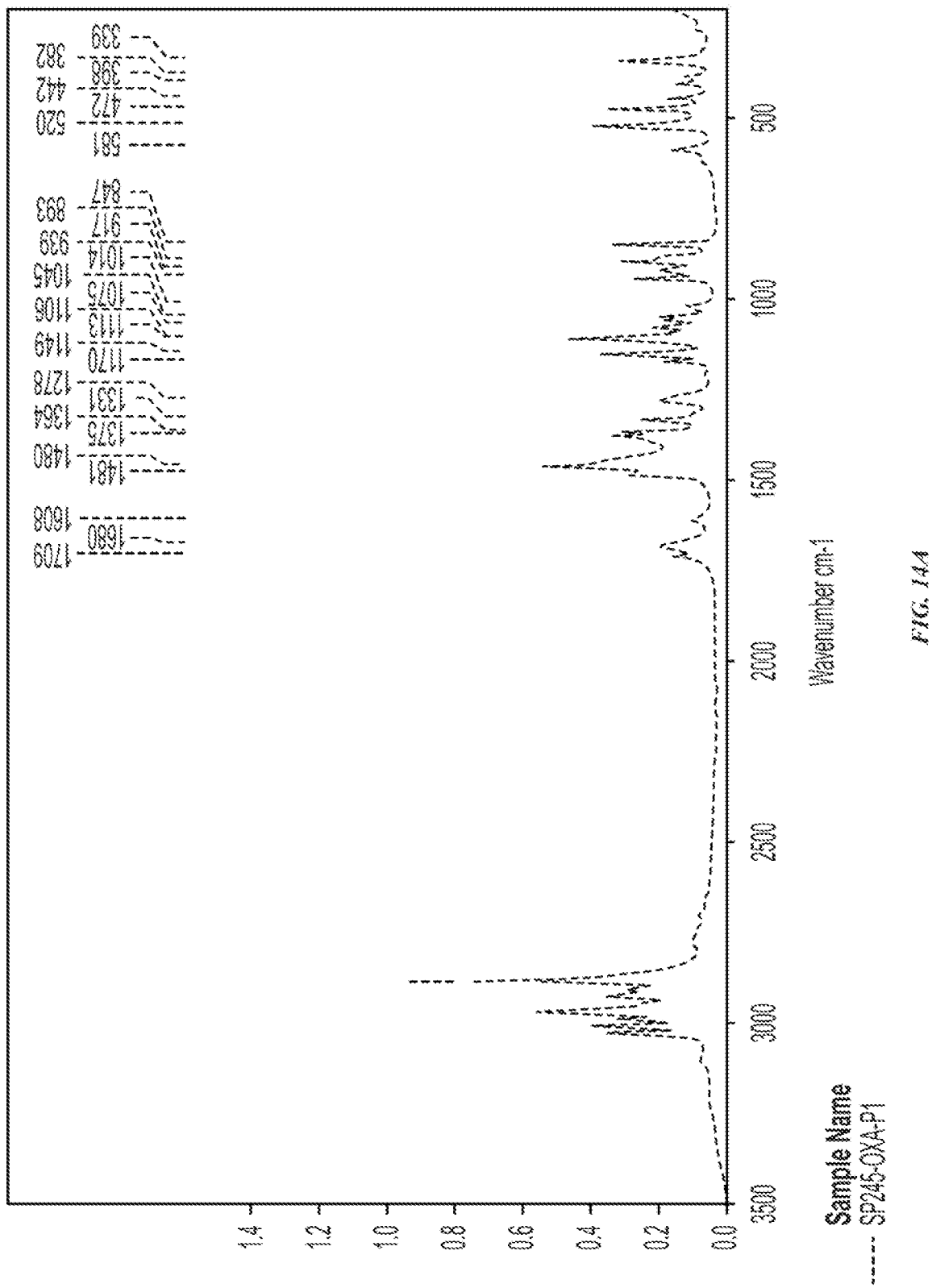
FIG. 14 is a characteristic FT-Raman spectrum of isofagomine oxalate: spectrum from 200 to 3500 cm−1 (FIG. 14A) and fingerprint region of the spectrum from 200 to 2000 cm−1 (FIG. 14B).
Figure 14B:
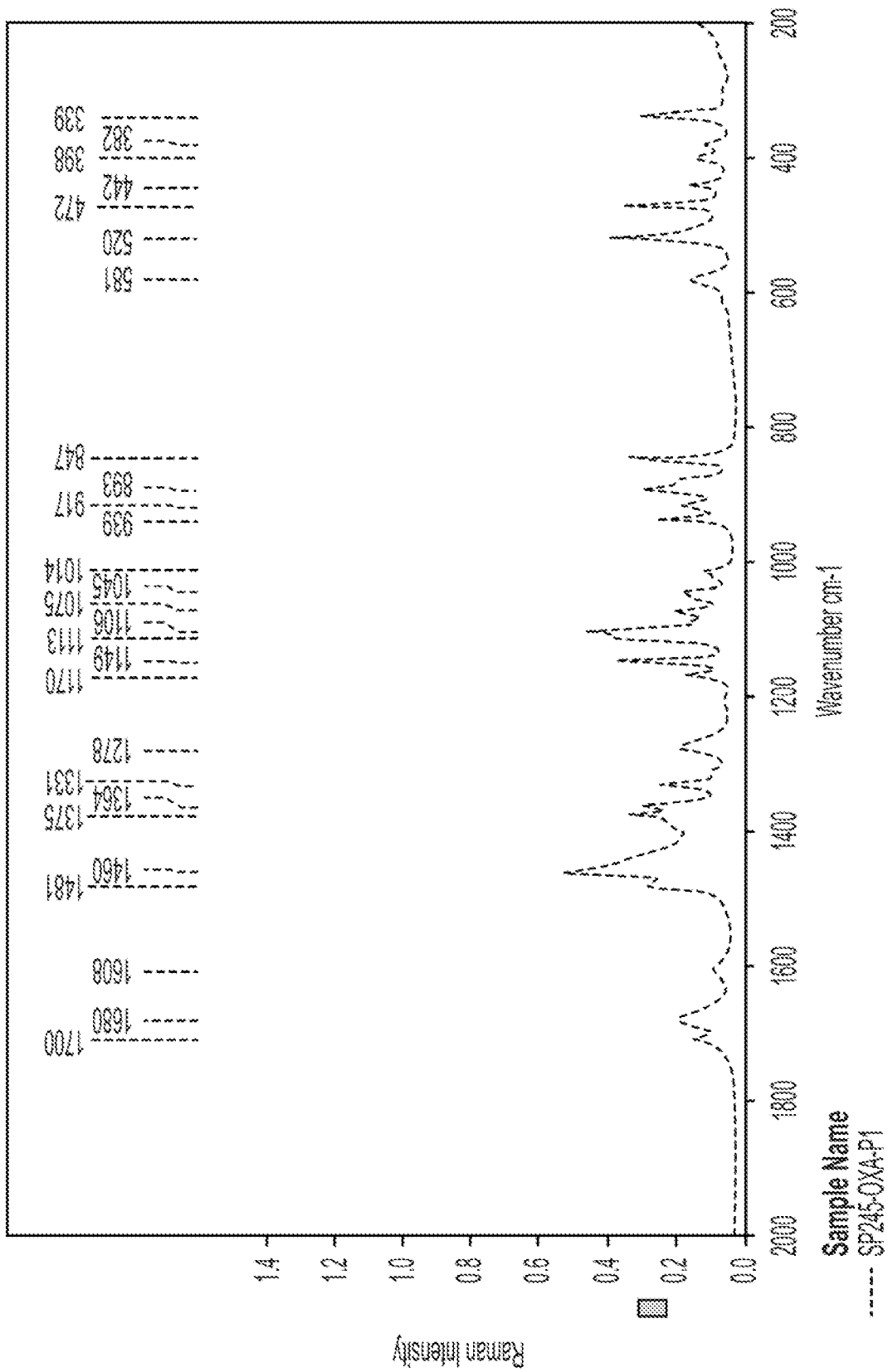

Raman spectrum was recorded for SP245-OXA-P1 and is presented in FIG. 14. An overview of the FT-Raman spectrum from 200 to 3500 cm$^{-1}$ (FIG. 14A) and fingerprint region of the FT-Raman spectrum from 200 to 2000 cm$^{-1}$ (FIG. 141B)

$^1$H-NMR Spectroscopy of Isofagomine Oxalate

Figure 15:
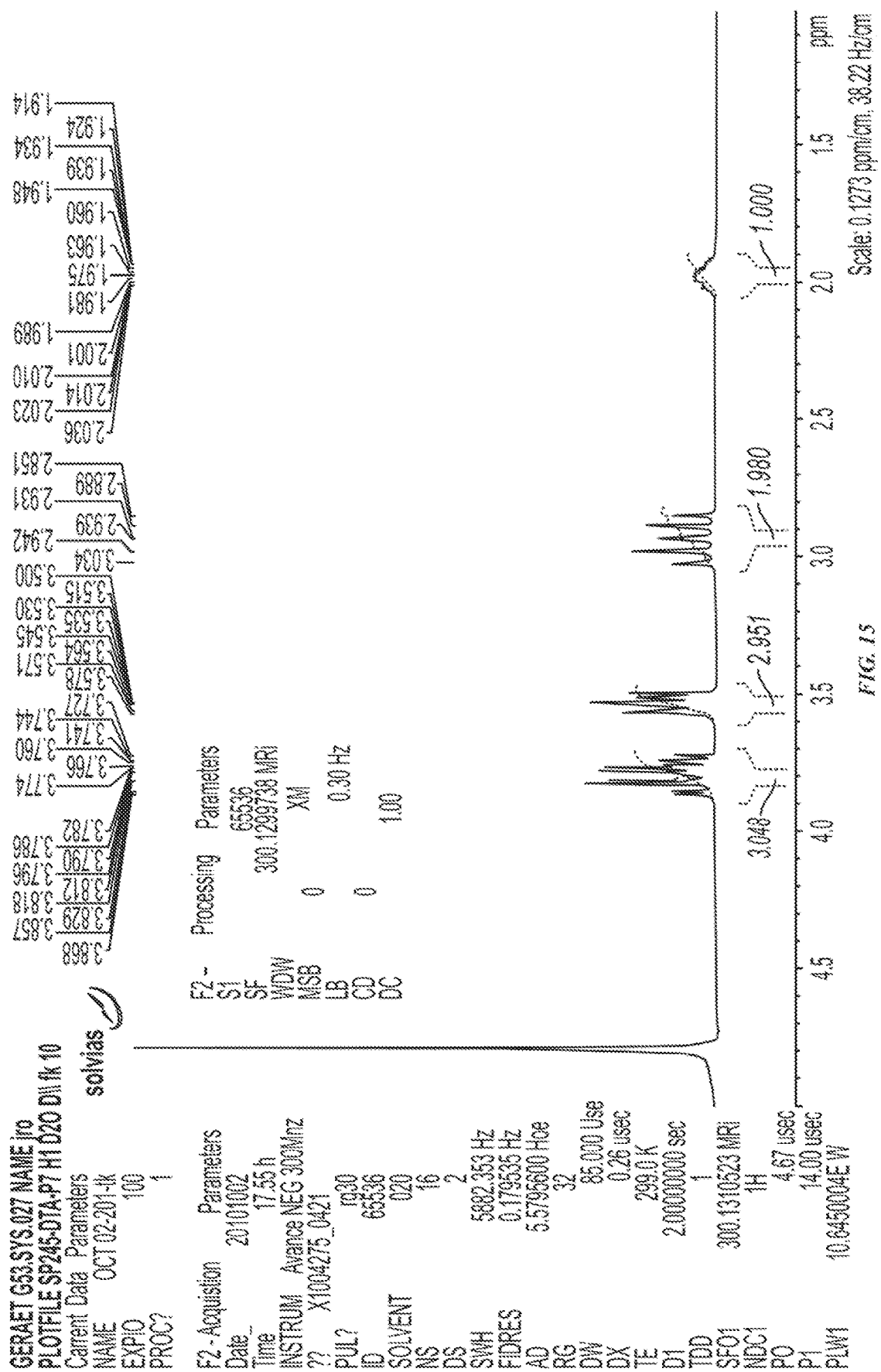
FIG. 15 is a characteristic 1H NMR spectrum of isofagomine oxalate.

The $^1$H-NMR spectrum of SP245-OXA-P1 was recorded in D$_2$O and is presented in FIG. 15. The spectrum is consistent with a 1 to 1 salt formation.

TG-FTIR of Isofagomine Oxalate

Figure 16:
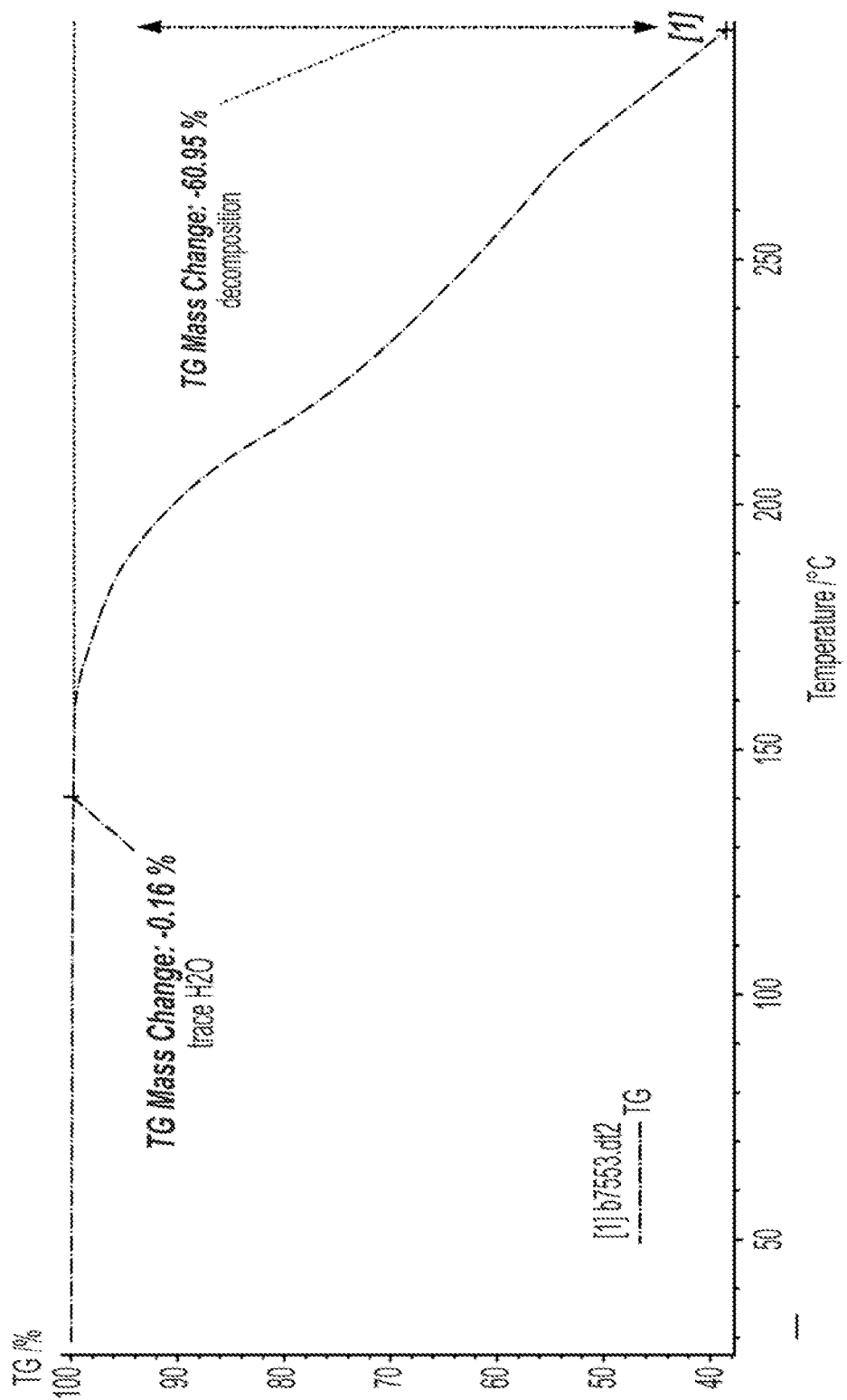
FIG. 16 is a TGA thermogram of a TG-IR analysis of isofagomine oxalate.

The TG-FTIR thermogram of SP245-OXA-P1 is presented in FIG. 16 and shows no considerable mass loss between 25° C. and 150° C. The fumarate salt is a solvent and water-free form.

Differential Scanning Calorimetry of Isofagomine Oxalate

Figure 17:
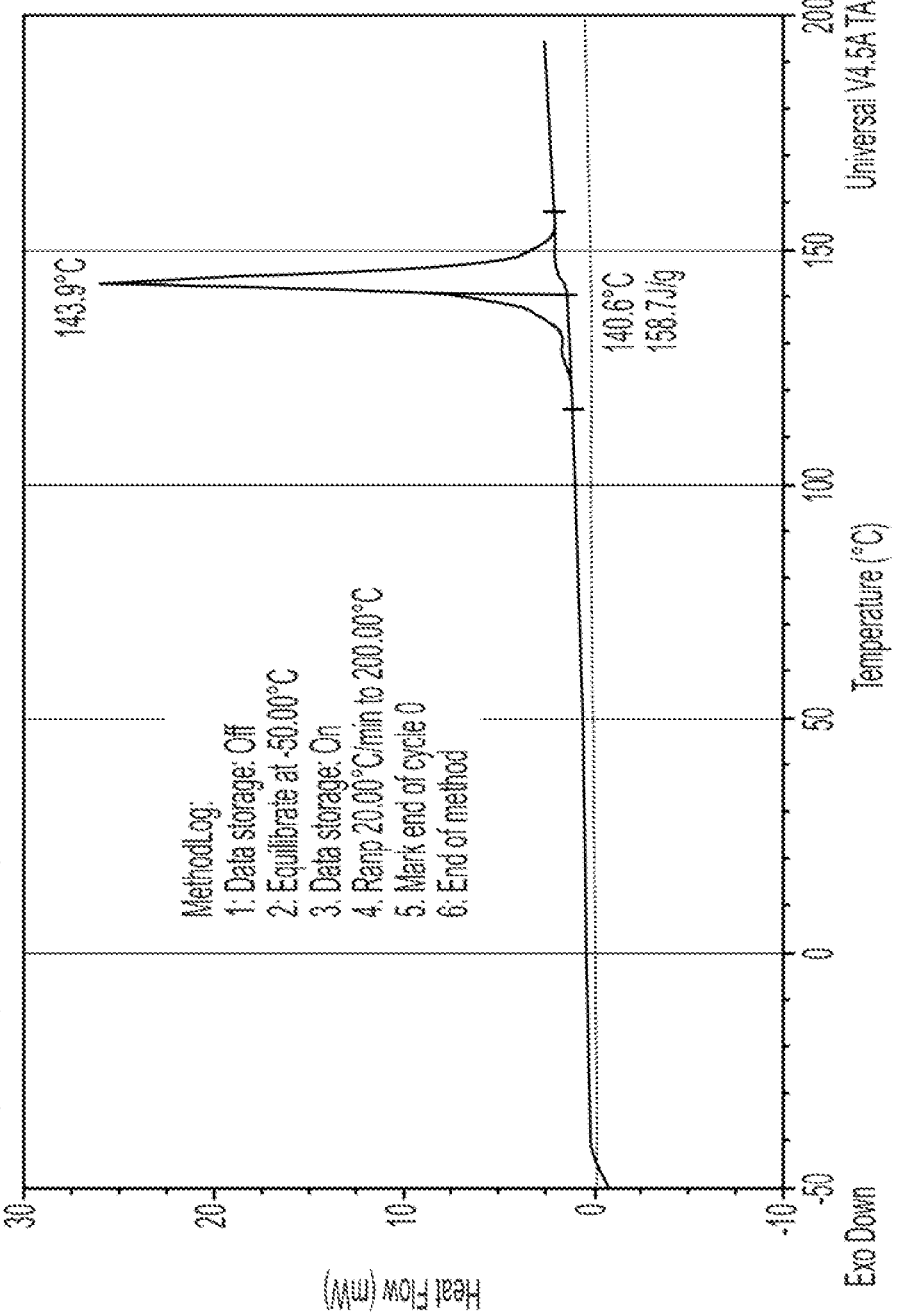
FIG. 17 is a DSC analysis of isofagomine oxalate.

Differential scanning calorimetry of SP245-OXA-P1 revealed a melting peak temperature at 143.9° C., an onset at 140.6° C. with an associated enthalpy of fusion of 158.7 J/g (FIG. 17).

Dynamic Vapor Sorption of Isofagomine Oxalate

Figure 18A:
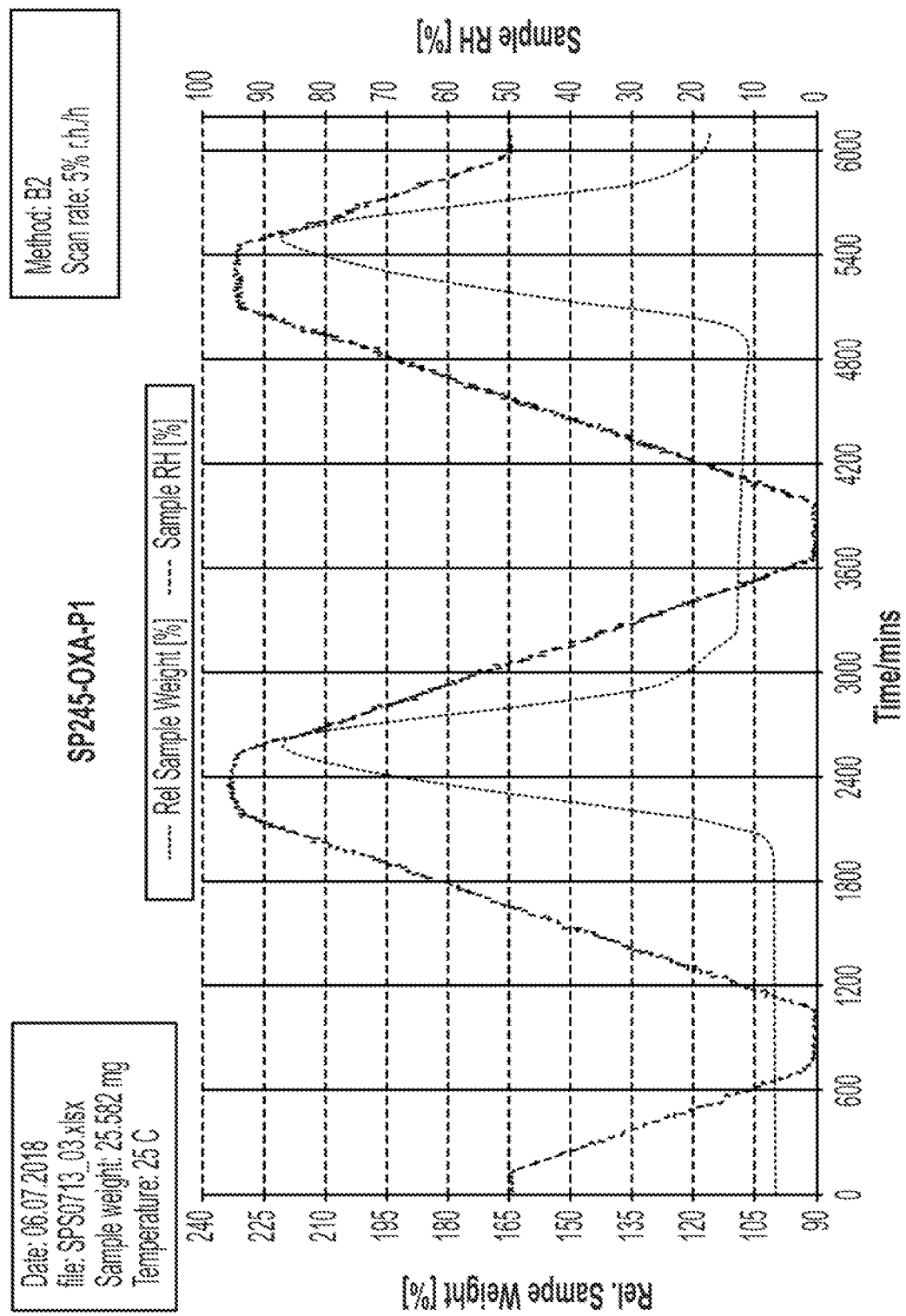
FIG. 18 is a DVS isotherm of isofagomine oxalate.
Figure 18B:
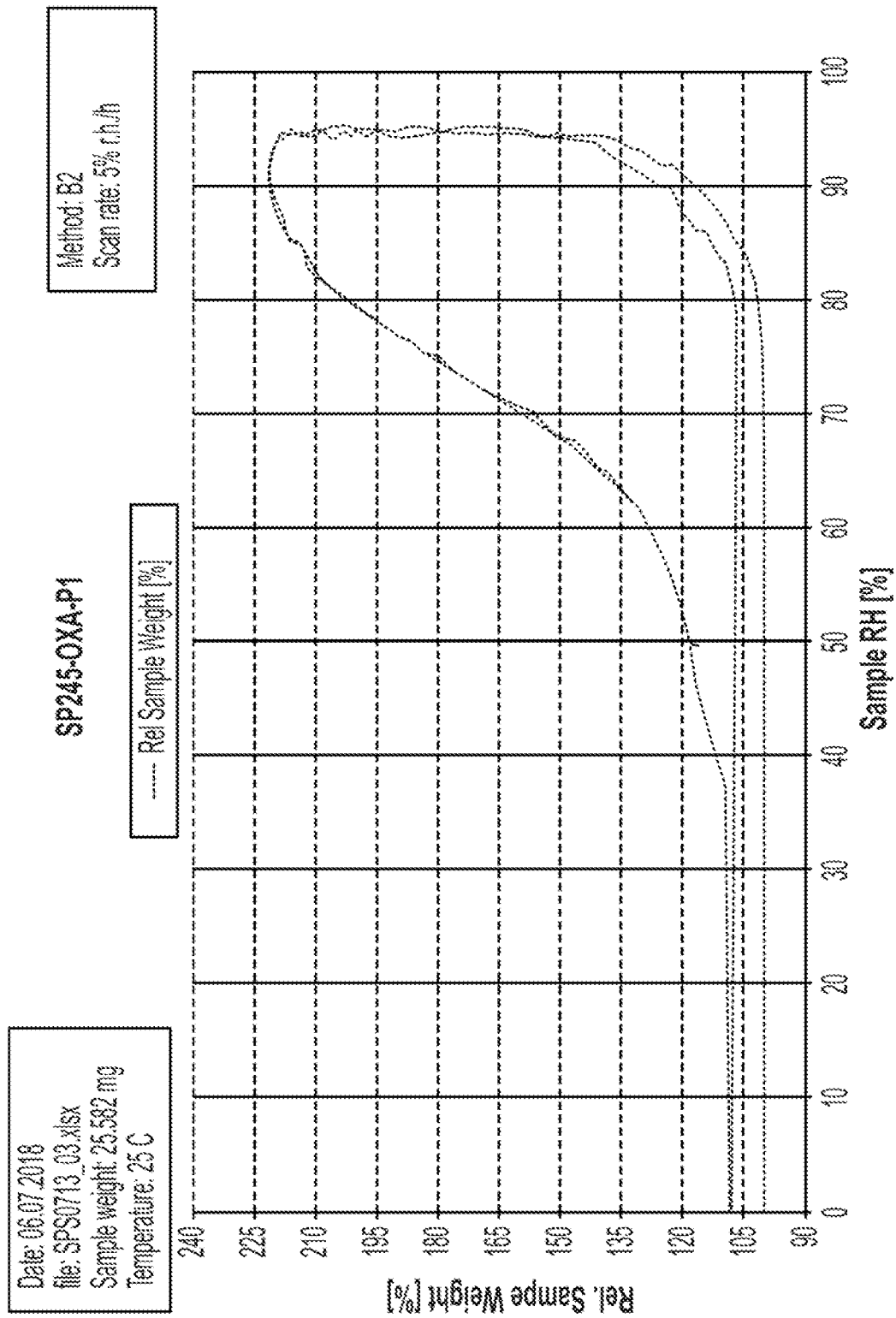

The effect of changes in relative humidity on the IFG oxalate salt sample SP245-OXA-P1 was studied using DVS. FIG. 18 shows the DVS isotherm: the change of relative sample weight (red curve) and relative humidity (blue curve) as a function of time (FIG. 18A) and the change of relative sample weight as a function of relative humidity (FIG. 18B).

No significant loss in weight was observed when decreasing the relative humidity from 50 to 0%. Furthermore, no gain in weight was observed when increasing the RH from 0 to 75%, then 30% mass gain was observed until 95% RH and additional 90% weight gain upon storage at 95%. The oxalate salt is hygroscopic above 80% RH. The sample recovered after DVS measurement was submitted to XRPD and the obtained XRPD pattern corresponds to the starting material.

Identity of Isofagomine Oxalate by Elemental Composition Analysis

The chemical identity of the IFG fumarate salt SP245-OXA-P1 was verified by elemental composition analysis using CHNO contents determinations and TG-FTIR for the water and solvent content. The obtained results are summarized in Table 6—CHNO content analysis for sample SP245-OXA-P1 compared with the theoretical composition of a (1:1) solvent and water-free salt with a molecular mass of 237.21 g/mol and the formula C8H15NO7. The results from the CHNO analysis show an excellent match with the theoretical content of a solvent and water-free fumarate salt.

TABLE 6

Elemental Analysis of Isofagomine Oxalate

| Element | SP245-OXA-P1 | Expected content for a solvent and water-free mono-oxalate salt |
|---|---|---|
| C | 40.7% | 40.51% |
| H | 6.6% | 6.37% |
| N | 5.9% | 5.90% |
| O | 45.6% | 47.21% |
| Water by TG-FTIR | <0.2% | 0% |

Example 4: Crystalline Isofagomine Tartrate

The below protocol was followed to prepare both D-tartaric acid and L-tartaric acid.

Solution 1 was prepared: a solution of tartaric acid was prepared in about 2 volumes of methanol at room temperature.

Solution 2 was prepared: a solution of purified IFG (obtained in accordance with Example A) in about 2 volumes methanol was prepared at room temperature. An equimolar amount of IFG is used relative to the tartaric acid used in the preparation of solution 1.

Solution 2 was then added slowly to solution 1, whereupon crystalline material was formed. After agitation at room temperature, the slurry was filtered, and the resultant solid material was washed with methanol, deliquored and then dried in vacuo.

Crystalline IFG-D-(−)-tartrate sample SP245-DTA-P3 was obtained according to the above protocol using D-tartaric acid in solution 1. Crystalline IFG L-(+)-tartrate sample SP245-LTA-P5 was also obtained according to the above protocol using L-tartaric acid in solution 1.

The D-tartrate salt has been made on a variety of scales ranging from milligram to as much as 600+gram scale with typical yields around 40-60%.

X-ray Powder Diffraction of Isofagomine D-(−)-Tartrate

Figure 19:
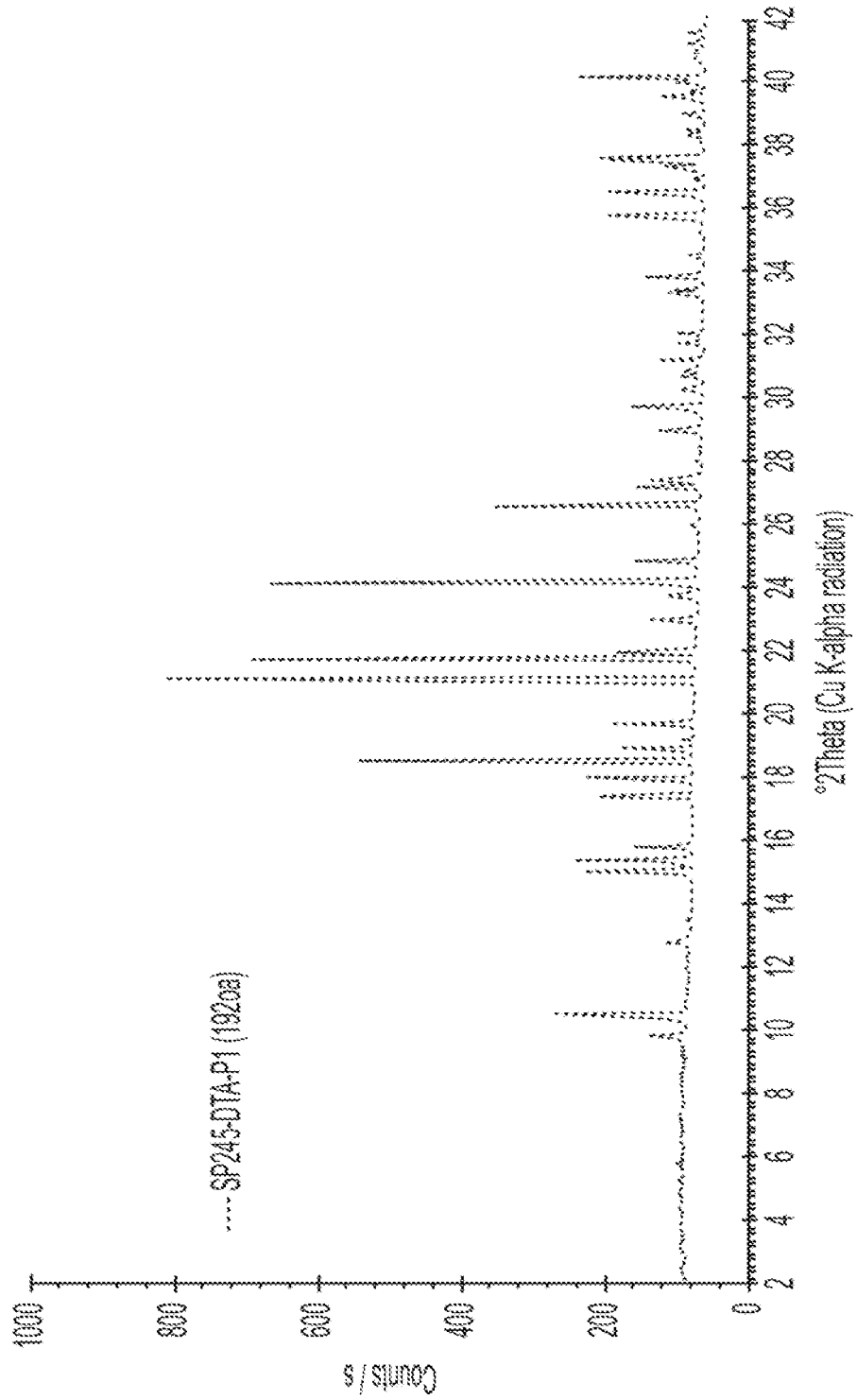
FIG. 19 is a characteristic XRPD spectrum of isofagomine D-(−)-tartrate.
Figure 20:
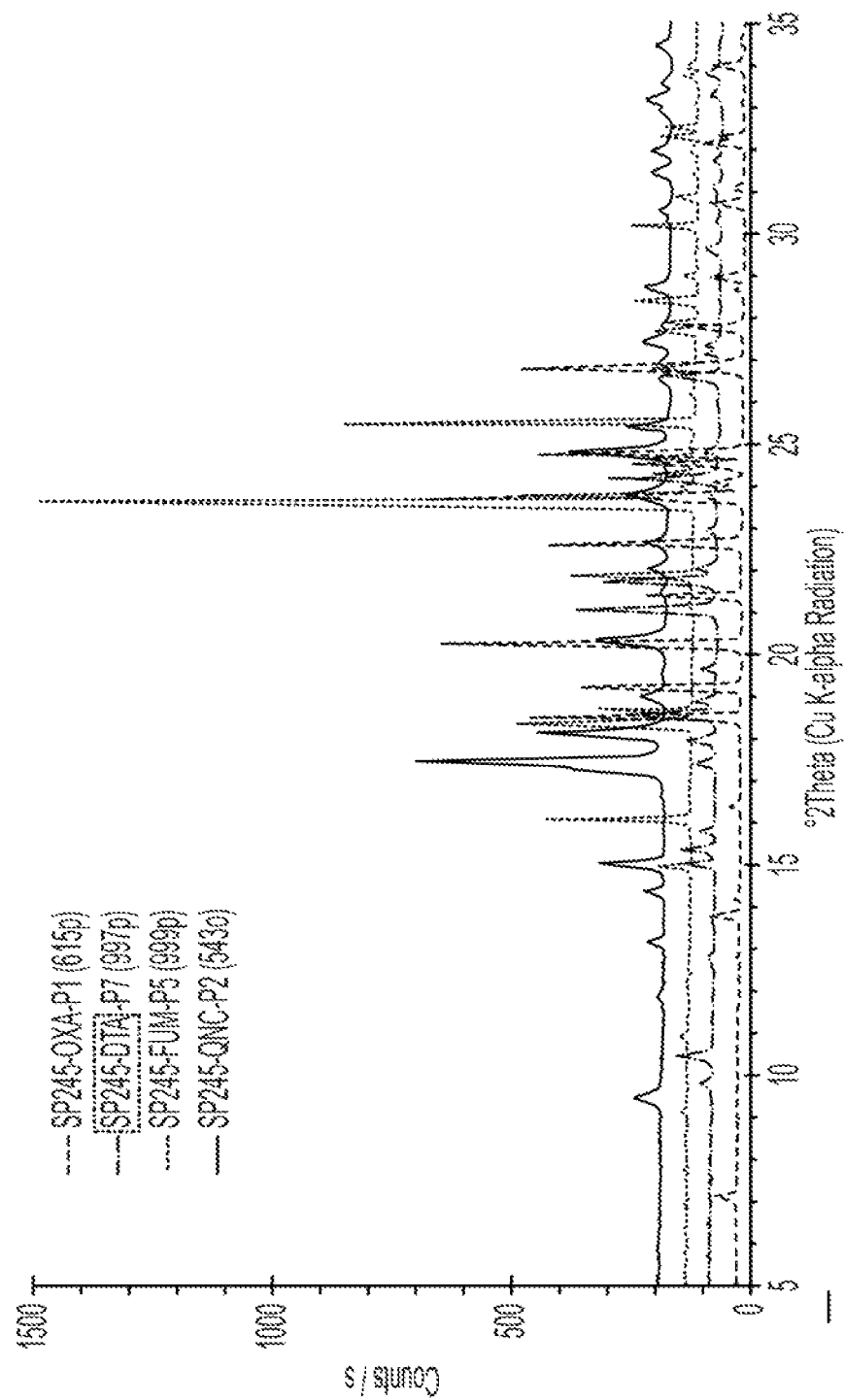
FIG. 20 is an overlay of XRPD spectra corresponding to the isofagomine salts prepared according to examples 1-4.

The XRPD pattern of SP245-DTA-P3 obtained from the protocol described above in in Example 4 is shown in FIG. 19 and tabulated in Table 7, below (vs=very strong, s=strong, m=medium, w=weak, vw=very weak intensity). Characteristic peaks are selected from the very strong, strong and medium diffraction peaks.

TABLE 7

XRPD peaks for Isofagomine D-(-)-Tartrate.
IFG D-Tartrate

| Peak No. | Angle in °2Θ | d-value in Å | Qualitative |
|---|---|---|---|
| 1 | 9.8 | 9.1 | m |
| 2 | 10.5 | 8.5 | s |
| 3 | 12.8 | 6.9 | w |
| 4 | 15.0 | 5.90 | s |
| 5 | 15.3 | 5.77 | s |
| 6 | 15.8 | 5.61 | m |
| 7 | 17.4 | 5.09 | m |
| 8 | 17.9 | 4.94 | m |
| 9 | 18.5 | 4.78 | s |
| 10 | 18.9 | 4.70 | m |
| 11 | 19.6 | 4.52 | m |
| 12 | 21.1 | 4.22 | vs |
| 13 | 21.7 | 4.08 | vs |
| 14 | 22.0 | 4.03 | m |
| 15 | 23.0 | 3.87 | w |
| 16 | 23.7 | 3.75 | w |
| 17 | 24.2 | 3.68 | vs |
| 18 | 24.8 | 3.59 | m |
| 19 | 26.6 | 3.35 | s |
| 20 | 27.1 | 3.28 | m |
| 21 | 27.4 | 3.25 | m |
| 22 | 29.0 | 3.08 | w |
| 23 | 29.6 | 3.01 | w |
| 24 | 33.8 | 2.65 | m |
| 25 | 35.7 | 2.51 | m |
| 26 | 36.5 | 2.46 | m |
| 27 | 37.5 | 2.39 | m |

Raman Spectroscopy of Isofagomine D-(-)-Tartrate

Figure 21:
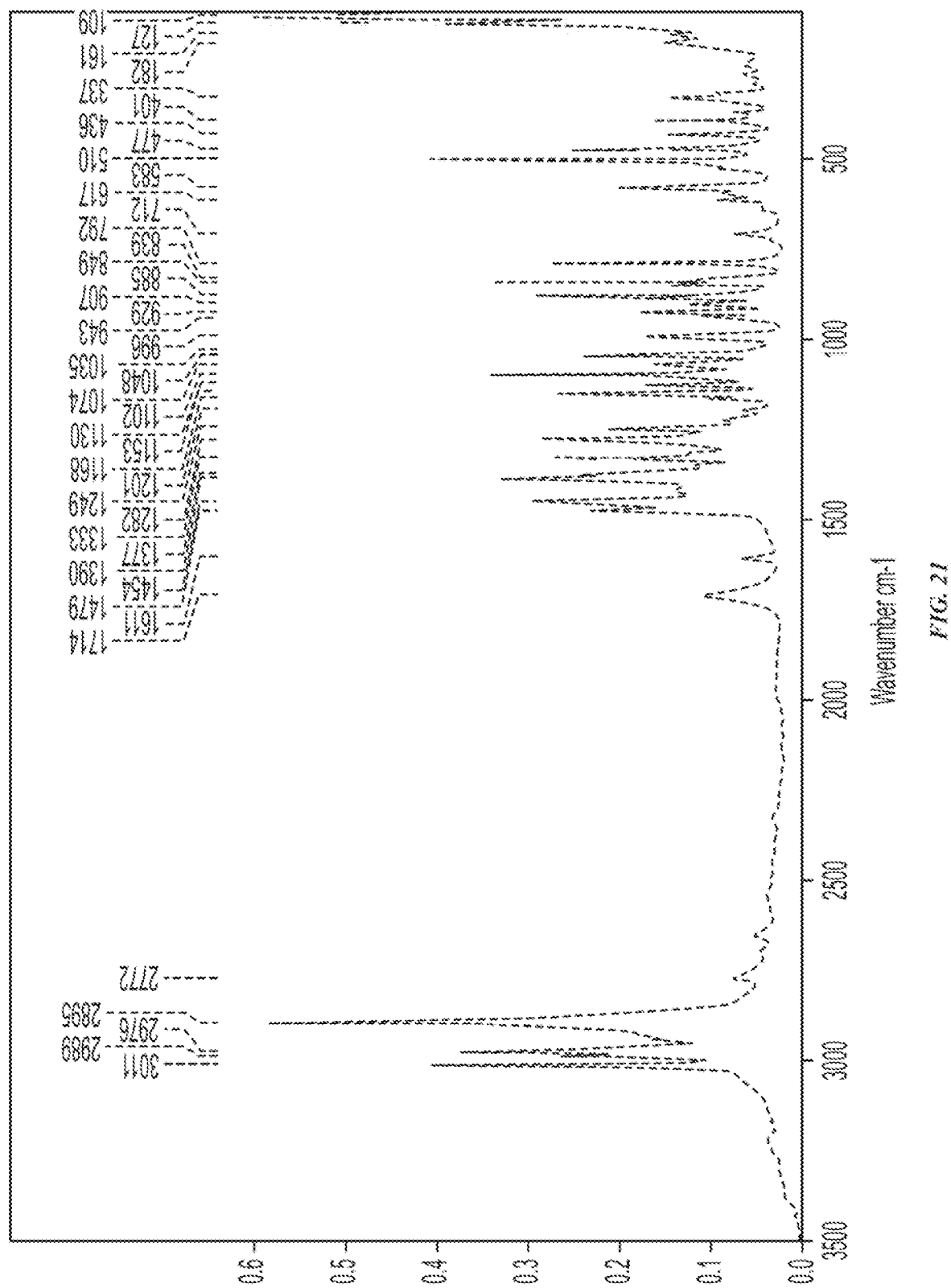
FIG. 21 is a characteristic FT-Raman spectrum of isofagomine D-(−)-tartrate (1:1): spectrum from 200 to 3500 cm−1.

Raman spectrum from 200 to 3500 cm$^{-1}$ was recorded for SP245-DTA-P3 and is presented in FIG. 21.

$^1$H-NMR Spectroscopy of Isofagomine D-(-)-Tartrate

Figure 22:
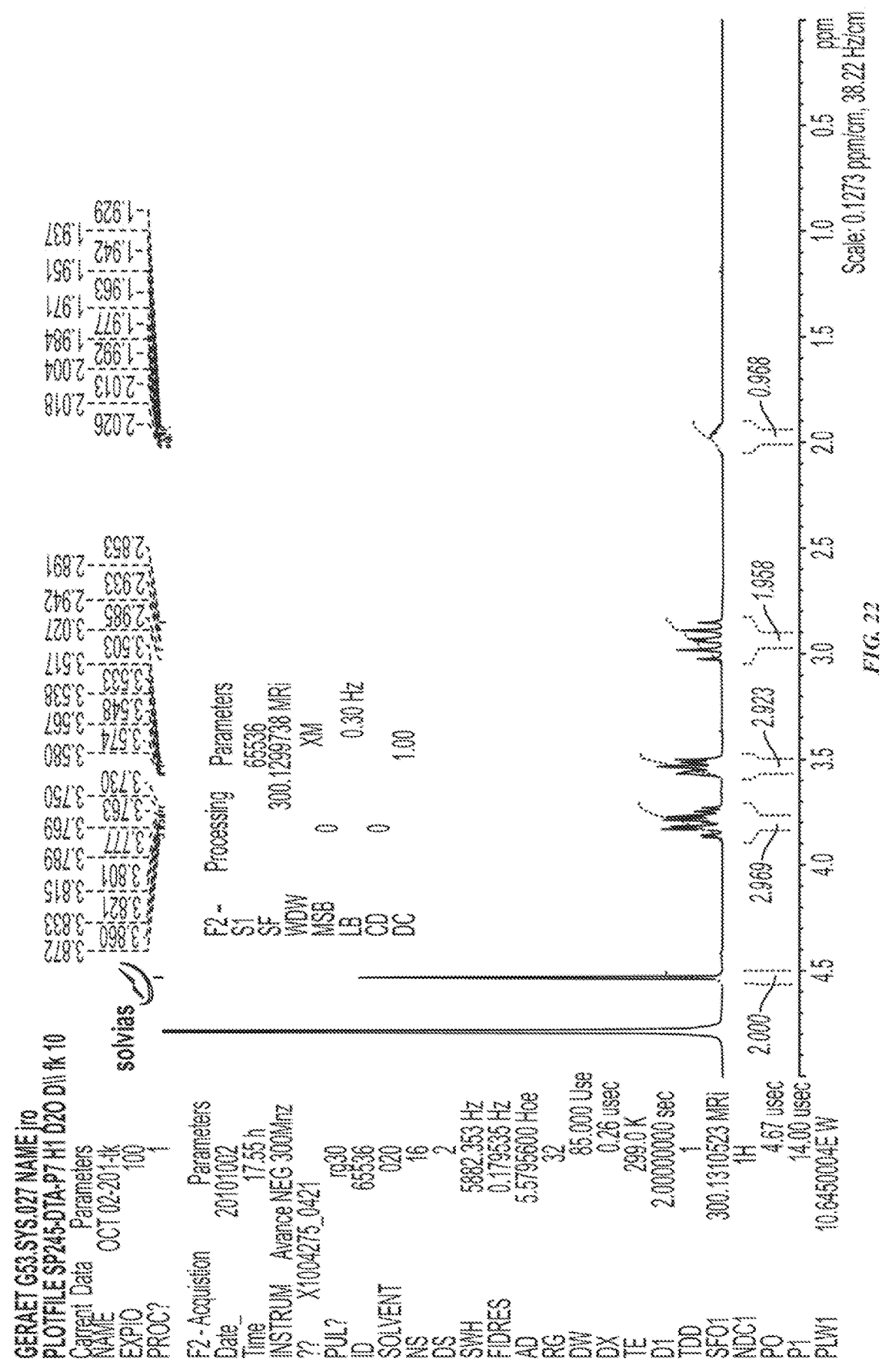

The $^1$H-NMR spectrum of SP245-DTA-P3 was recorded in D$_2$O and is presented in FIG. 22. The spectrum is consistent with a 1 to 1 salt formation.

TG-FTIR of Isofagomine D-(-)-Tartrate

Figure 23:
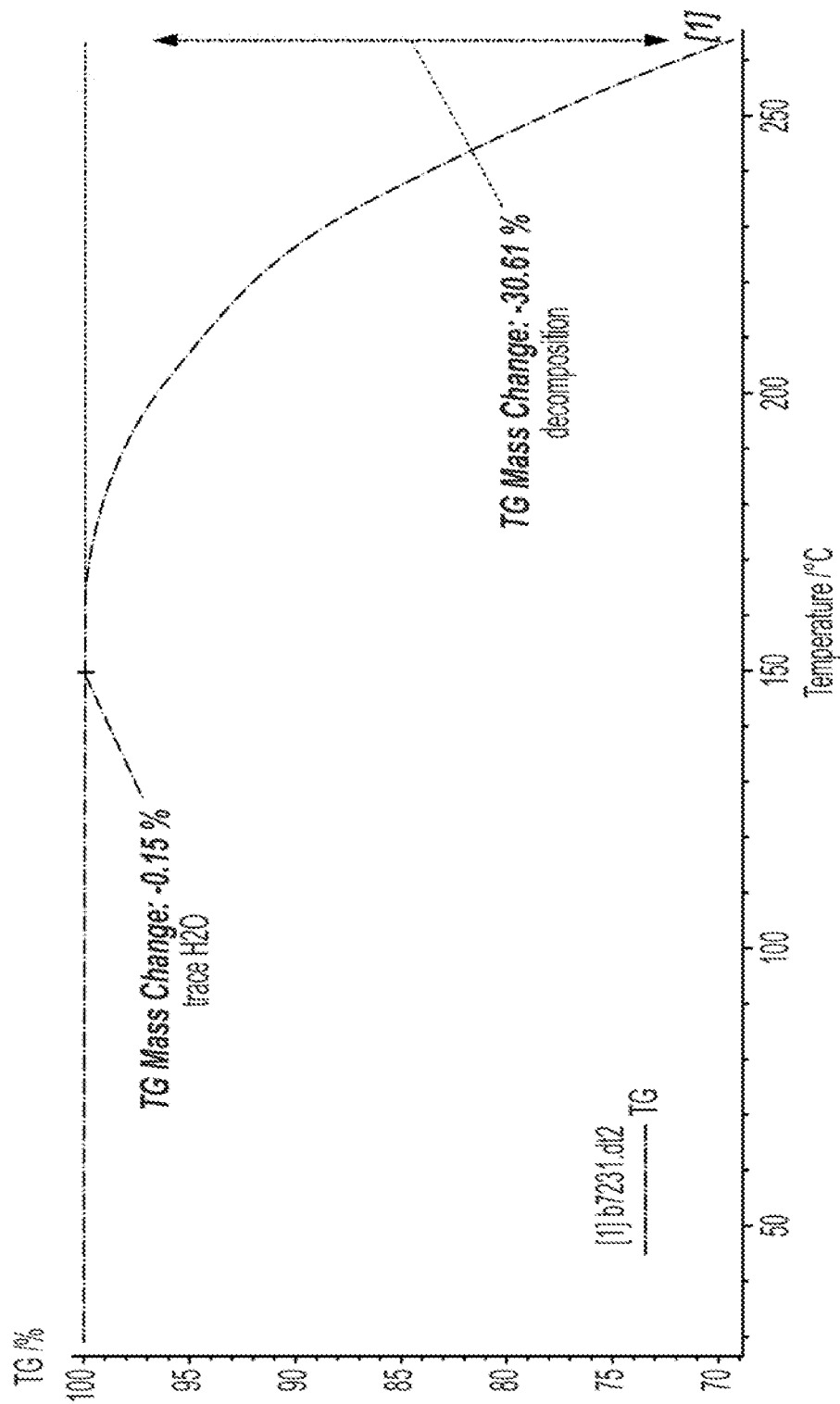
FIG. 23 is a TGA thermogram of a TG-IR analysis of isofagomine D-(−)-tartrate (1:1).

The TG-FTIR thermogram of SP245-DTA-P3 is presented in FIG. 23 and shows no considerable mass loss between 25° C. and 150° C. The tartrate salt is a solvent and water-free form.

Differential Scanning Calorimetry of Isofagomine D-(-)-Tartrate

Figure 24:
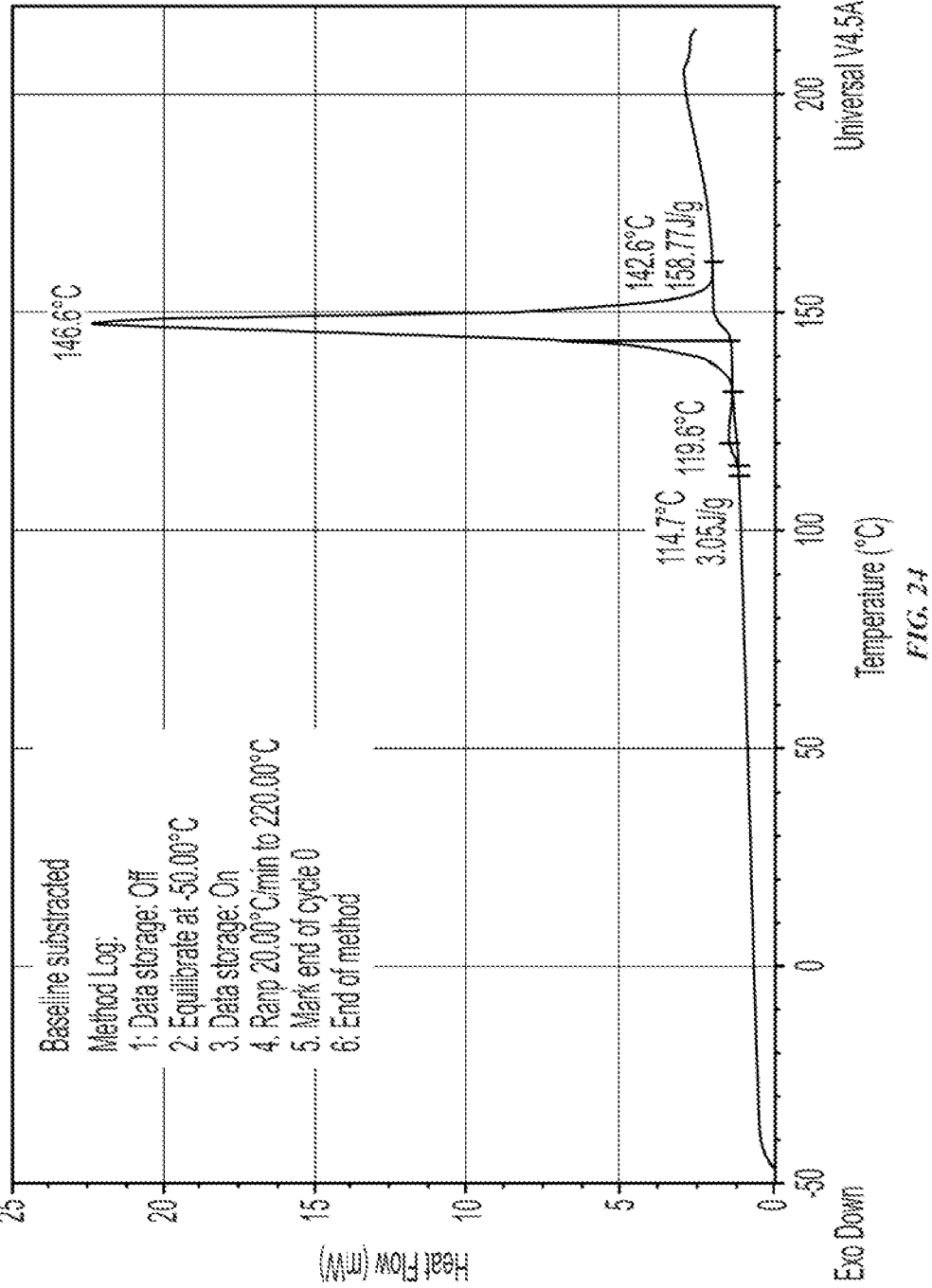
FIG. 24 is a DSC analysis of isofagomine D-(−)-tartrate (1:1).

Differential scanning calorimetry of SP245-DTA-P3 revealed a melting peak temperature at 146.6° C., an onset at about 132° C. with an associated enthalpy of fusion of 158.7 J/g (FIG. 24).

Dynamic Vapor Sorption of Isofagomine D-(-)-Tartrate

Figure 25:
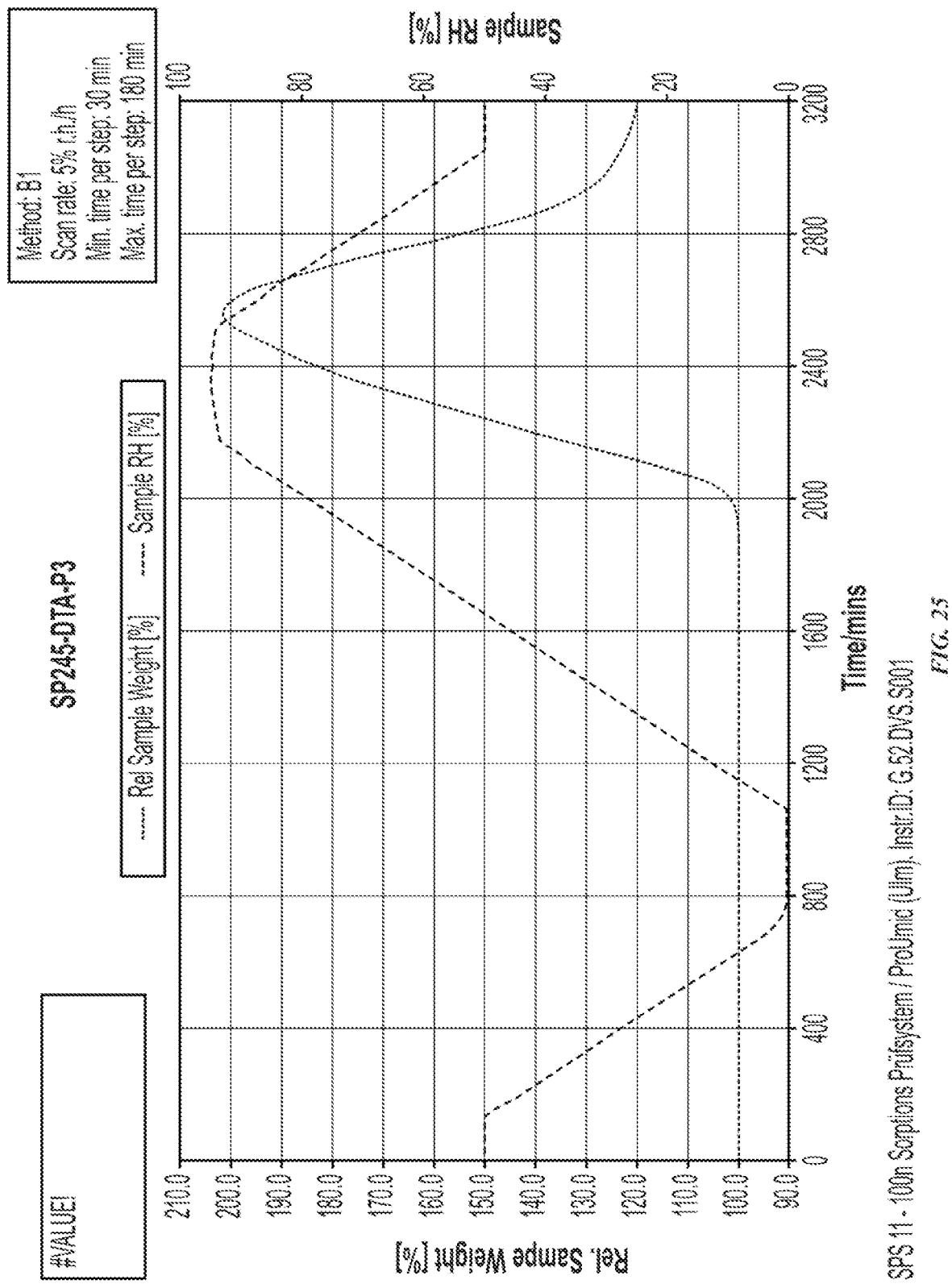
FIG. 25 is a DVS isotherm of isofagomine D-(−)-tartrate (1:1).

The effect of changes in relative humidity on the crystalline IFG tartrate salt sample SP245-DTA-P3 was studied using DVS. FIG. 25 shows the DVS isotherm: the change of relative sample weight (red curve) and relative humidity (blue curve) as a function of time. No mass change was observed upon increasing the relative humidity (RH) from 0% to 70%, indicating that this salt is not hygroscopic up to a RH of 70%. However, upon changing the RH from 70% to 95% resulted in a mass gain of 32%, and holding the material at 95% RH resulted in an additional mass increase of 70%.

Identity of Isofagomine D-Tartrate Salt by Elemental Composition Analysis

The chemical identity of the IFG D-Tartrate salt SP245-DTA-P3 was verified by elemental composition analysis using CHNO contents determinations and TG-FTIR for the water and solvent content. The obtained results are summarized in Table 8—CHNO content analysis for sample SP245-OXA-P1 compared with the theoretical composition of a (1:1) solvent and water-free salt with a molecular mass of 237.21 g/mol and the formula C8H15NO7. The results from the CHNO analysis show an excellent match with the theoretical content of a solvent and water-free mono-tartrate salt.

TABLE 8

Elemental Analysis of Isofagomine D-(-)-Tartrate

| Element | SP245-DTA-P3 | Expected content for a solvent and water-free mono-tartrate salt |
|---|---|---|
| C | 40.1% | 40.4% |
| H | 6.3% | 6.4% |
| N | 4.6% | 4.7% |
| O | 48.4% | 48.4% |
| Water by TG-FTIR | 0.15% | 0% |

Example 5: Stability Study of Isofagomine Salts

In order to obtain insight regarding thermal stability of the four crystalline IFG salts, storage stress-tests at 80° C. over several days were conducted. A sample of the free base (SP245-FB-P4), a fumarate sample (SP245-FUM-P5), a D-tartrate sample (SP245-DTA-P7), an L-tartrate sample (SP245-LTA-P5) and an oxalate sample SP245-OXA-P2 were stored at 80° C. for one, three and seven days in closed vials. Samples were tested by CAD and $^1$H-NMR.

CAD-HPLC was performed in order to identify the possible adducts or thermal degradation product that could be generated upon storage under the given conditions. All samples were examined by CAD-HPLC; however, no considerable changes were observed between the starting materials and the stored samples. The results are presented in Table 9 and suggest that the IFG salts are stable under the examined conditions. In addition, XRPD was carried out for the seven-day stored crystalline salt samples and the XRPD patterns before and after storage were essentially identical.

All salts were significantly more stable than the free base after seven days storage at 80° C. NMR spectroscopy was conducted on the seven-day stored samples. For the free base sample, several additional NMR signals were observed after storage compared to the non-stressed sample and thus confirmed the observed purity loss in HPLC. No significant changes were noted in the NMR samples of the salts.

TABLE 9

CAD-HPLC results of stability study of the isofagomine salts.

| Sample/New Sample Name | Duration | Area % |
|---|---|---|
| SP245-FB-P4 (starting material) | | 81.1 |
| SP245-FB-P7-1d | 1 day | 80.2 |
| SP245-FB-P6-3d | 3 days | 80.6 |
| SP245-FB-P5-7d | 7 days | 80.4 |
| SP245-FUM-P5 (starting material) | | 87.9 |
| SP245-FUM-P9-1d | 1 day | 86.9 |
| SP245-FUM-P8-3d | 3 days | 87.1 |
| SP245-FUM-P7-7d | 7 days | 87.8 |
| S P245-DT/VP7 (starting material) | | 86.3 |
| SP245-DTA-P10-1d | 1 day | 85 |
| SP245-DTA-P9-3d | 3 days | 85.1 |
| SP245-DTA-P8-7d | 7 days | 85.6 |

TABLE 9-continued

CAD-HPLC results of stability study of the isofagomine salts.

| Sample/New Sample Name | Duration | Area % |
|---|---|---|
| SP245-LTA-P5 (starting material) | | 84.3 |
| SP245-LTA-P8-1d | 1 day | 83.9 |
| SP245-LTA-P7-3d | 3 days | 84.1 |
| SP245-LTA-P6-7d | 7 days | 85.3 |
| SP245-OXA-P2 (starting material) | | 85.9 |
| SP245-0XA-P5-1d | 1 day | 83.6 |
| SP245-OXA-P4-3d | 3 days | 82.9 |
| SP245-OXA-P3-7d | 7 days | 83.6 |

Example 6: Exemplary GCase and IFG/GCase Pharmaceutical Formulations

| Formulation | A | B | C |
|---|---|---|---|
| | 2.5 mg/mL Velaglucerase alfa 50 mM sodium citrate 5% sucrose 0.01% PS20 pH 6.0 | 60 mg/mL Velaglucerase alfa 3 mM IFG 10 mM sodium citrate 250 mM sucrose 0.1% P188 pH 6.0 | 180 mg/mL Velaglucerase alfa 10 mM IFG 10 mM sodium citrate 250 mM sucrose 0.1% P188 pH 6.0 |
| GCase:IFG ratio | — | 1:3 | 1:3.3 |

IFG for use in the above formulations A, B and C is selected from one of the following: IFG free base, IFG quinate, IFG malate, IFG fumarate, IFG oxalate, IFG malonate, IFG succinate, IFG D-tartrate, IFG cyclamate or IFG ascorbate.

Example 7—Stability Study of Tartrate and Fumarate IFG/GCase Formulations

This report summarizes the data collected for the stability study of velaglucerase alfa in formulations containing isofagomine tartrate or isofagomine fumarate. The purpose of the study was to evaluate if isofagomine fumarate has a comparable stabilization effect to isofagomine tartrate, and whether isofagomine fumarate can be an alternative salt to isofagomine tartrate.

This study evaluated the stability of velaglucerase alfa formulations at approximately 140 mg/mL containing two different IFG salt forms, isofagomine tartrate and isofagomine fumarate were evaluated during storage and mechanical stress. The results show that 1) There was no significant difference between the two formulations after preparation, in terms of appearance, pH, protein concentration, osmolality, P188 concentration, sub-visible particles, RP-HPLC, SDS-PAGE, activity, intact mass at reduced and non-reduced condition and peptide mapping at T0, 40° C. and −20° C. for up to 1 month, as well as after shaking for 24 hours. A slight difference of A320 values was observed at T0, −20° C. for 1 month and shaking at 200 rpm for 24 hours.
2) Isofagomine content in fumarate formulation was slightly higher than that in tartrate formulation at both T0 and after storage at 40° C. for a month. Viscosity of fumarate formulation was slightly higher than that of tartrate formulation.
3) Aggregation data from two different SE-HPLC methods showed that fumarate formulation is less stable than tartrate formulation during storage at 40° C. No significant difference was observed after storage at −20° C. or shaking for 24 hours.
4) DSC results also show Tm value for velaglucerase alfa in tartrate formulation is slightly higher than that in fumarate formulation.

Collectively, the results show that the two prepared formulations at T0 were comparable by all the assays, except that isofagomine content was slightly higher than that in tartrate formulation. Both formulations were stable during shaking, storage at −20° C. and storage at −40° C. However, fumarate formulation was relatively less stable than tartrate formulation during storage at −40° C. as measured by SEC, and the viscosity for fumarate formulation is also slightly higher than that of tartrate formulation.

This set of data suggests that isofagomine fumarate can be an alternative to isofagomine tartrate with a slight compromise on stability and viscosity.

1. Sample Preparation

The velaglucerase alfa was thawed at room temperature. The thawed velaglucerase alfa was concentrated at room temperature with a Millipore Labscale® TFF system using Pellicon XL cassette (Catalogue #: PXB010A50, Biomax® 10 KDa, Chemistry polyethersulfone). The velaglucerase alfa was concentrated to approximately 160 mg/mL. Then the concentrated velaglucerase alfa (47.5 mL) was loaded into Slide-A-Lyzer® dialysis cassette (10K MWCO) and dialyzed against 2.0 L of formulation buffers containing either 7.5 mM of isofagomine fumarate or isofagomine tartrate twice at 2-8° C.

Table 10 shows the composition of the two formulation buffers. The pH of isofagomine•tartrate formulation and isofagomine•fumarate formulation was adjusted with 1.0 NaOH to 6.0 from 5.61 and 4.48, respectively.

TABLE 10

Composition of velaglucerase alfa formulations containing IFG Tartrate and IFG Fumarate

| | tartrate formulation (original) | fumarate formulation (replacement) |
|---|---|---|
| IFG molar concentration | 7.5 mM | 7.5 mM |
| Salt form | tartrate | fumarate |
| Citric acid | 0.0 mM | 8.32 mM |
| Sodium citrate | 10 mM | 1.68 mM |
| P188 | 0.1% W/W | 0.1% W/W |
| Sucrose | 250 mM | 250 mM |
| pH | 6.0 | 6.0 |

Each of the concentrated protein formulation solutions was filtered (with a Millipore Steriflip-GV®) and aseptically filled into a 6R type I glass vial and stoppered with a 20-mm grey rubber serum stopper and crimped with an aluminum seal.

1.1 Stress Conditions 1.1.1 Storage at 40° C.

A set of the filled vials were stored inverted at 40° C. for 17 days (0.5 month) and 32 days (1 month).

1.1.2 Storage at −20° C.

The filled vials were stored upright at −20° C. for 32 days (1 month).

1.1.3 Agitation

The agitation was performed on the rotatory shaker at 200 rpm for 24 hours at room temperature in a horizontal orientation.

1.2 Testing Methods
1.2.1 Routine Assay methods
Table 11 shows a list of the testing methods.

TABLE 11

Testing Methods

| Test | Quality target |
|---|---|
| Appearance | Colorless to slightly colored, Clear to slightly opalescent, Essentially free of visible particles |
| pH | pH 6.0 ± 0.3 |
| A280 | Report result |
| SE-HPLC | ≥90.0% main peak; ≤5.0% HMWS |
| RP-HPLC | ≥90.0% main peak; No new peaks greater than 1.0% of total peak area compared to Reference Standard |
| SDS-PAGE | No single impurity band greater than 3% |
| Specific Activity | 19-45 U/mg |
| P188 | Report results |
| IFG | Report results |
| MFI | NA |
| Osmolality | NA |
| Viscosity | NA |
| DSC | NA |
| A320 | NA |
| LC-MS | NA |

2. Data Analysis

Stability trend of velaglucerase alfa formulation containing IFG-fumarate (fumarate formulation, thereafter) is compared against that of velaglucerase alfa in IFG-tartrate (tartrate formulation thereafter) at 40° C. and −20° C. as well as under the shaking stress.

2.1 Appearance

The appearance was observed in the intact vials under regular light. All the vials for both tartrate formulation and fumarate formulation were clear to slightly opalescent, colorless, essentially free from visible particles at T0, after storage at 40° C. for 0.5 and 1 month, after storage at −20° C. for 1 month or after shaking at 200 rpm for 24 hours.

2.2 pH

Table 12 shows pH results. There is no change of pH for both formulations at 40° C.

TABLE 12 pH results

| | T0 | 40° C. for 1 month |
|---|---|---|
| Tartrate formulation | 5.92 | 5.92 |
| Fumarate formulation | 5.90 | 5.93 |

2.3 Protein Concentration

Protein concentration was measured using SoloVPE by varying the pathlength and measuring precisely the absorbance at 280 nm of the undiluted drug substance as a function of pathlength. The absorbance at 280 nm was corrected by the absorbance at 320 nm, which was an indicator of light scattering. The slope of the data (absorbance units/mm) was directly proportional to the protein concentration according to Beer's law. Velaglucerase alfa protein concentration was calculated using the slope of the linear plot of absorbance vs. pathlength and an extinction coefficient of 1.63 $(mg/mL)^{-1}(cm)^{-1}$ for velaglucerase alfa. Results are expressed in mg/mL. Table 13 shows the concentration results. There was no significant change after storage at 40° C. for 1 month.

TABLE 13

Concentration (mg/mL) results

| | T0 | 40° C. for 1 month |
|---|---|---|
| Tartrate buffer | 0.01 | NS |
| Fumarate buffer | 1.2 | NS |
| Tartrate formulation | 141.8 | 142.9 |
| Fumarate formulation | 140.0 | 139.6 |

2.4 P188 Concentration

Table 14 shows P188 concentration results. There was no significant difference between these two formulations in terms of P188 concentration.

TABLE 14

P188 concentration (% w/v)

| | T0 |
|---|---|
| Tartrate formulation | 0.209 |
| Fumarate formulation | 0.221 |

2.5 IFG Concentration

Velaglucerase alfa drug substance was formulated in buffer containing 3 mM isofagomine (IFG). The IFG concentration in velaglucerase alfa drug substance was analyzed by reversed-phase ultra performance liquid chromatography (UPLC). In this approach, 6-aminoquinolyl-N-hydroxysuccinimidyl carbamate (AQC) quantitatively reacts with IFG, which converts IFG into a UV detectable form and then separated by UPLC. Detection wavelength was 260 nm. IFG standards are run to produce a standard curve. A linear regression was performed on the IFG standard data and the resulting parameters are used to calculate IFG concentration in the samples. Results are reported in mM.

Table 15 shows IFG concentration results. There was no change during storage at 40° C. for a month. However, fumarate formulation contained a slightly higher IFG concentration than tartrate formulation.

TABLE 15

IFG concentration

| | T0 | 40° C. for 1 month |
|---|---|---|
| Tartrate formulation | 7.73 | 7.16 |
| Fumarate formulation | 9.39 | 9.42 |

2.6 Osmolality

Table 16 shows the Osmolality results. There was no significant difference in Osmolality, however the result was higher than the optimal Osmolality, but consistent with the results of other studies using the same method.

TABLE 16

Osmolality results (mOSm)

| | T0 (n = 2) |
|---|---|
| Tartrate formulation | 376.5 + 10.6 |
| Fumarate formulation | 370.5 + 10.6 |

2.7 Sub-Visible Particles

Table 17 shows the subvisible particle results. There was no significant difference between these two formulations.

However, these was an increase of sub-visible particle counts for both of the formulations during the storage at 40° C. and −20° C., and after shaking at 200 rpm for 24 hours.

TABLE 17

Sub-visible particle counts (average ± SD, n = ¾) for velaglucerase alfa in tartrate and fumarate formulations

|  |  | 2-10 size | 10-100 size | 25-100 |
|---|---|---|---|---|
| T0 | Tartrate formulation | 544 ± 216 | 69 ± 23 | 13 ± 2 |
|  | Fumarate formulation | 560 ± 96 | 56 ± 13 | 8 ± 0 |
| 40° C. for 1 month | Tartrate formulation | 2225 ± 1467 | 280 ± 180 | 26 ± 16 |
|  | Fumarate formulation | 3191 ± 1006 | 307 ± 155 | 22 ± 9 |
| −20° C. for 1 month | Tartrate formulation | 1216 ± 545 | 143 ± 62 | 12 ± 8 |
|  | Fumarate formulation | 2128 ± 1526 | 284 ± 218 | 39 ± 25 |
| Shaking at 200 RPM for 24 hours | Tartrate formulation | 2112 ± 538 | 216 ± 54 | 24 ± 2 |
|  | Fumarate formulation | 2654 ± 114 | 335 ± 116 | 52 ± 22 |

2.8 Viscosity

Viscosity was measured with m-VROC viscometer using a 500-μL syringe. Each sample was tested at 20° C. at a flow rate of 50, 100 and 200 μL/min, and the average result was reported. The samples for which the viscosity was measured had been stored at 2-8° C. for 3 months before the measurement, and no apparent change in appearance was observed.

Table 18 shows viscosity of these two formulations. The viscosity for velaglucerase alfa in Tartrate formulation was slightly less than that in fumarate formulation.

TABLE 18

Viscosity of velaglucerase alfa in Isofagomine tartrate and isofagomine fumarate formulations

|  | Viscosity (cP) |
|---|---|
| Tartrate formulation | 5.9 |
| Fumarate formulation | 6.6 |

2.9 A320

A320 data were collected using a plat reader. The samples (each well) were loaded into a UV-Star® Microplate (96 well, Clear®, clear), and the data were collected at 320 nm.

Table 19 shows A320 value for velaglucerase alfa formulations at different treatment conditions. A320 value for fumarate formulation was a slightly greater than that for tartrate formulation at T0, −20° C. for a month, and after shaking for 24 hours. No significant difference was observed between these two formulations after storage at 40° C. for 0.5 and 1 month.

TABLE 19

A320 value (average ± SD, n = 3) of velaglucerase alfa in Isofagomine tartrate and isofagomine fumarate formulation

|  | Tartrate | Fumarate |
|---|---|---|
| T0 | 0.272 ± 0.000 | 0.291 ± 0.003 |
| 40 C.-0.5 month | 0.357 ± 0.001 | 0.360 ± 0.000 |
| 40 C.-1 month | 0.392 ± 0.001 | 0.391 ± 0.001 |
| −20 C.-1 month | 0.290 ± 0.002 | 0.309 ± 0.002 |
| Shaking at 200 rpm for 24 hours | 0.289 ± 0.000 | 0.306 ± 0.001 |

2.10 Activity

In vitro activity was determined by measuring the rate at which the substrate p-nitrophenyl β-D-glucopyranoside was hydrolyzed by velaglucerase alfa to p-nitrophenol and β-D-glucopyranoside. The reaction was stopped by the addition of a glycine carbonate buffer. The absorbance of the characteristic yellow p-nitrophenol product was measured at 405 nm. Velaglucerase alfa enzyme activity was determined by interpolation of a standard curve generated in the assay. One unit (U) of enzyme activity was defined as the quantity of velaglucerase alfa required to convert one micromole of p-nitrophenyl j-D-glucopyranoside per minute under the specified assay conditions. The reportable activity value of velaglucerase alfa samples is U/mL.

Table 20 shows the activity results. There was no significant change after storage for up to 1 month at 40° C. and −20° C. as well as after shaking for 24 hours at 200 rpm.

TABLE 20

Activity results

|  | Tartrate | Fumarate |
|---|---|---|
| T0 | 35.0 | 36.4 |
| 40° C. for 0.5 month | 38.9 | 38.0 |
| 40° C. for 1 month | 35.8 | 37.9 |
| −20° C. for 1 month | 37.9 | 38.5 |
| Shaking at 200 rpm for 24 hours | 33.0 | 36.7 |

2.11 SE-HPLC.

Size exclusion HPLC (SE HPLC) is used to assess size homogeneity of velaglucerase alfa. This method separates proteins by their hydrodynamic size. Larger species (eg, aggregates, dimers, and oligomers) elute earlier than the velaglucerase alfa monomeric main species as pre-peaks and smaller species (eg, degradation products and fragments) elute later as post-peaks. Eluted peaks are detected by absorbance at 214 nm. This method reports percent main peak and percent high molecular weight (HMW) species. All the samples were tested with two different SE-HPLC methods. RE-PMP-0010 and RE-PMP-0013. RE-PMP-0010 is a method for commercial VPRIV®, in which velaglucerase alfa molecule monomer is eluted after the buffer peak, possibly due to the interaction between velaglucerase alfa molecule and the stationary phase. RE-PMP-0013 is a method developed for VPRIV-SubQ formulations, and in this method, 10% is acetonitrile is used as a component of elution buffer. Both methods were used in the study to characterize the velaglucerase alfa in these two formulations.

2.11.1 VPRIV Method (RE-PMP-0010).

SE-HPLC chromatograms of velaglucerase alfa at T0, 40° C. for 0.5 and 1 month, −20° C. for 1 month and horizontal shaking for 24 hours, respectively, were evaluated in both formulations.

Table 21 shows the SE-HPLC retention time for velaglucerase alfa after treatment at different conditions. 40C17D corresponds to a storage condition at 42° C. for 17 days (or 0.5 month), 40C1M corresponds to storage condition at 40° C. for 1 month, N20C1M corresponds to storage for −20° C. for 1 month. The monomer peak was eluted at 34 min, and aggregates species were eluted in between 12.8 min to 23.9 min. The buffer peak was eluted at 25-27 min. However, the distribution of aggregate species after storage at 40° C. for 0.5 and 1 month were different from those in velaglucerase alfa at T0, or after storage at −20° C. for 1 month or shaking for 24 hours. However, there was no apparent difference of peak positions of these species at all the treatment conditions between tartrate formulation and fumarate formulation.

TABLE 21

SE-HPLC retention time (min) for velaglucerase alfa in tartrate and fumarate formulations

| Sample | HMWS 1 | HMWS 2 | Aggregate | Unknown 1 | Unknown 2 | Unknown 3 | Monomer |
|---|---|---|---|---|---|---|---|
| Tartrate T0 | 12.89 | 15.52 | 16.35 | 19.56 | 21.47 | 22.34 | 33.99 |
| Fumarate T0 | 13.02 | 15.66 | 16.52 | 19.77 | 21.73 | 22.98 | 34.44 |
| Tartrate 40C17D | 12.85 | — | 16.29 | 19.57 | 23.09 | 23.70 | 33.93 |
| Fumarate 40C17D | 12.87 | — | 16.28 | 19.55 | 21.96 | 23.74 | 33.89 |
| Tartrate 40C1M | 12.82 | — | 16.30 | 19.56 | 23.06 | 23.82 | 33.98 |
| Fumarate 40C1M | 12.83 | — | 16.31 | 19.57 | 22.03 | 23.86 | 34.22 |
| Tartrate N20C1M | 12.84 | 15.49 | 16.33 | 19.55 | 21.46 | 22.34 | 33.95 |
| Fumarate N20C1M | 12.90 | 15.52 | 16.35 | 19.57 | 21.48 | 22.67 | 34.16 |
| Tartrate Shaked | 12.88 | 15.52 | 16.34 | 19.56 | 21.46 | 22.38 | 33.84 |
| Fumarate Shaked | 12.87 | 15.52 | 16.33 | 19.56 | 21.47 | 22.55 | 34.06 |

Table 22 shows the SE-HPLC relative peak area for different species in velaglucerase alfa after treatment at different conditions. There was no apparent difference between these two formulations at T0, after storage at 40° C. for 0.5 month, at −20° C. for 1 month or shaking for 24 hours. At 40° C. for 1 month, fumarate formulation shows a higher level of aggregation than tartrate formulation.

2.11.2 SE-HPLC Method (RE-PMP-0013)

SE-HPLC chromatograms of velaglucerase alfa at T0, 40° C. for 0.5 and 1 month, −20° C. for 1 month and horizontal shaking for 24 hours, respectively in both formulations using the method adapted to VPRIV SubQ formulations were evaluated.

TABLE 22

SE-HPLC relative peak area for velaglucerase alfa in tartrate and fumarate formulations

| | Sample | HMWS1 | HMWS2 | Aggregate | Unknown 1 | Unknown 2 | Unknown 3 | Monomer |
|---|---|---|---|---|---|---|---|---|
| T0 | Tartrate | 0.0 | 0.1 | 0.5 | 0.7 | 0.8 | 0.8 | 97.1 |
| | Fumarate | 0.0 | 0.2 | 0.6 | 0.7 | 0.6 | 0.9 | 97.1 |
| 40° C. for 0.5 month | Tartrate | 1.2 | — | 0.3 | 0.4 | 0.4 | 0.3 | 97.4 |
| | Fumarate | 1.1 | — | 0.3 | 0.4 | 0.3 | 0.3 | 97.5 |
| 40° C. for 1 month | Tartrate | 1.3 | — | 0.4 | 0.5 | 0.4 | 0.3 | 97.2 |
| | Fumarate | 2.0 | — | 0.4 | 0.5 | 0.3 | 0.4 | 96.5 |
| −20° C. for 1 month | Tartrate | 0.0 | 0.2 | 0.6 | 0.7 | 0.8 | 0.8 | 97.0 |
| | Fumarate | 0.0 | 0.2 | 0.5 | 0.6 | 0.7 | 0.8 | 97.1 |
| Shaking at 200 rpm for 24 hours | Tartrate | 0.0 | 0.2 | 0.6 | 0.6 | 0.8 | 0.8 | 97.1 |
| | Fumarate | 0.0 | 0.2 | 0.6 | 0.6 | 0.8 | 0.8 | 97.1 |

Table 23 shows the retention time of SE-HPLC peaks for velaglucerase alfa. There was an aggregate species at approximately 16.4 min, and a monomer peak at 19.6 min for the both formulations at T0, after storage at −20° C. for 0.5 month and shaking for 24 hours as well. An additional aggregate peak (unknown 1) appeared after storage at 40° C. for 0.5 month and 1.0 month. However, there was no apparent difference in retention time and distribution of the species between these two formulations at the same treatment conditions.

TABLE 23

SE-HPLC retention time for velaglucerase alfa in isofagomine tartrate and isofagomine fumarate formulations

| | Sample | Unknown 1 | Aggregate | Monomer |
|---|---|---|---|---|
| T0 | Tartrate | — | 16.44 | 19.65 |
| | Fumarate | — | 16.42 | 19.50 |
| 40° C. for 0.5 month | Tartrate | 12.89 | 16.44 | 19.64 |
| | Fumarate | 12.80 | 16.40 | 19.57 |
| 40° C. for 1 month | Tartrate | 12.92 | 16.48 | 19.63 |
| | Fumarate | 12.77 | 16.41 | 19.67 |
| | Tartrate | — | 16.46 | 19.69 |
| | Fumarate | — | 16.40 | 19.59 |
| Shaking for 24 hours at room temperature 40° C. for 0.5 month | Tartrate | — | 16.40 | 19.54 |
| | Fumarate | — | 16.40 | 19.59 |

Table 24 shows the relative peak area of SE-HPLC peaks for both formulations. There was no significant difference between these two formulations at T0, after storage at −20° C. and shaking for 24 hours. The total amount of HMWS (unknown 1+aggregate) for fumarate formulation was more than that for tartrate formulation.

TABLE 24

SE-HPLC relative peak area for velaglucerase alfa in isofagomine tartrate and isofagomine fumarate formulations

| | Sample | Unknown 1 | Aggregate | Monomer |
|---|---|---|---|---|
| T0 | Tartrate | 0.0 | 0.7 | 99.3 |
| | Fumarate | 0.0 | 0.6 | 99.4 |
| 40° C. for 0.5 month | Tartrate | 0.5 | 0.3 | 99.2 |
| | Fumarate | 0.8 | 0.4 | 98.8 |
| 40° C. for 1 month | Tartrate | 0.6 | 0.3 | 99.1 |
| | Fumarate | 1.6 | 0.4 | 98.0 |
| −20° C. for 1 month | Tartrate | 0.0 | 0.5 | 99.5 |
| | Fumarate | 0.0 | 0.6 | 99.4 |
| Shaking for 24 hours at room temperature | Tartrate | 0.0 | 0.5 | 99.6 |
| | Fumarate | 0.0 | 0.7 | 99.3 |

2.12 RP-HPLC

Reversed phase high performance liquid chromatography (HPLC) is performed to measure the relative amount of potential process and product related impurities in velaglucerase alfa. This method resolves velaglucerase alfa degradation products by a reversed phase column with a gradient of increasing organic content. The method detects the main velaglucerase alfa peak, plus other peaks prior to and following the main peak at 214 nm. Purity is reported as relative percent area of the main peak.

RP-HPLC chromatograms of velaglucerase alfa at T0, storage at 40° C. for 0.5 and 1 month, storage at −20° C. for 1 month and horizontal shaking for 24 hours, respectively, were evaluated. There was a slight difference of the chromatograms between these two formulations after storage at 40° C. for 0.5 month and 1.0 month.

Table 25 shows the retention time of RP-HPLC peaks for velaglucerase alfa. There was no significant difference in retention time for velaglucerase alfa between these two formulations at T0, after storage at −20° C. for 1 month and shaking for 24 hours. The relative peak elution time for velaglucerase alfa stored at 40° C. for 0.5 month and 1.0 month was slightly different between these two formulations.

TABLE 25

RP-HPLC retention time for velaglucerase alfa in isofagomine tartrate and isofagomine fumarate formulations

| | Sample | Peak A | Unknown | Peak B | Peak C | Main | Post-Main 2 |
|---|---|---|---|---|---|---|---|
| T0 | Tartrate | 24.07 | 24.77 | 25.60 | 26.37 | 27.39 | 31.77 |
| | Fumarate | 23.97 | 24.70 | 25.53 | 26.34 | 27.44 | 31.96 |
| 40° C. for 0.5 month | Tartrate | 23.60 | 24.79 | 25.52 | 27.00 | 27.66 | 31.88 |
| | Fumarate | 23.89 | 24.91 | 25.61 | 26.71 | 27.64 | 31.70 |
| 40° C. for 1 month | Tartrate | 23.13 | 24.85 | 25.55 | 27.00 | 27.68 | 31.79 |
| | Fumarate | 23.45 | 24.51 | 25.15 | 26.34 | 27.33 | 31.51 |
| −20° C. for 1 month | Tartrate | 23.99 | 24.64 | 25.51 | 26.30 | 27.35 | 31.83 |
| | Fumarate | 24.12 | 24.81 | 25.58 | 26.38 | 27.44 | 31.64 |
| Shaking at 24 hours 200 rpm for | Tartrate | 24.24 | 24.76 | 25.65 | 26.44 | 27.41 | 31.86 |
| | Fumarate | 23.94 | 24.53 | 25.40 | 26.21 | 27.28 | 31.75 |

Table 26 shows the relative RP-HPLC peak area for both formulations. There was no significant difference between these two formulations at T0, after storage at −20° C. and shaking for 24 hours. There was a slight difference in the relative peak area of peak C and main peak between these two formulations that were stored at 40° C. for 0.5 month and 1.0 month.

There was a phase transition at approximately 52° C. for both buffers. The transition thermal transition event was more prominent for fumarate buffer. Velaglucerase alfa in both buffers shows a prominent peak, and the Tm of the peak is summarized in Table 27. The Tm value for velaglucerase alfa in these two formulations was comparable.

TABLE 26

RP-HPLC relative peak area for velaglucerase alfa in isofagomine tartrate and isofagomine fumarate formulations

| | Sample | Peak A | Unknown | Peak B | Peak C | Main | Post-Main 2 | Pre-Peak Total | Post-Peak Total |
|---|---|---|---|---|---|---|---|---|---|
| T0 | Tartrate | 0.09 | 0.12 | 0.94 | 1.21 | 97.45 | 0.19 | 2.36 | 0.19 |
| | Fumarate | 0.05 | 0.12 | 0.94 | 1.23 | 97.51 | 0.14 | 2.34 | 0.14 |
| 40° C. month for 0.5 | Tartrate | 0.01 | 0.13 | 0.65 | 1.05 | 97.87 | 0.29 | 1.84 | 0.29 |
| | Fumarate | 0.04 | 0.15 | 0.68 | 0.62 | 98.27 | 0.24 | 1.49 | 0.24 |
| 40° C. month for 1 | Tartrate | 0.06 | 0.19 | 0.70 | 1.09 | 97.59 | 0.36 | 2.04 | 0.36 |
| | Fumarate | 0.03 | 0.16 | 0.65 | 0.67 | 98.26 | 0.24 | 1.51 | 0.24 |
| −20° C. month for 1 | Tartrate | 0.08 | 0.11 | 0.93 | 1.23 | 97.47 | 0.19 | 2.35 | 0.19 |
| | Fumarate | 0.14 | 0.17 | 1.04 | 1.29 | 97.10 | 0.26 | 2.64 | 0.26 |
| Shaking rpm for 24 hours at 200 | Tartrate | 0.05 | 0.08 | 0.88 | 1.20 | 97.61 | 0.18 | 2.21 | 0.18 |
| | Fumarate | 0.10 | 0.10 | 0.95 | 1.21 | 97.44 | 0.21 | 2.36 | 0.21 |

2.13 SDS-PAGE

Sodium dodecyl sulfate polyacrylamide gel electrophoresis (SDS PAGE) under denaturing and reducing conditions is used to assess velaglucerase alfa purity. Velaglucerase alfa test samples, reference standard, and two assay controls are diluted with sample dilution buffer and mixed with reductant (dithiothreitol), denatured under heat and loaded onto a Tris-glycine gradient gel. Molecular weight markers are also tested on the gel. Following electrophoresis, the gels are Coomassie blue stained and developed. Test samples are evaluated for the presence of fragments or nonreducible aggregates. The purity is assessed by comparison with reference standard and assay controls with 2 different impurity levels (1.000 and 3.00%).

SDS-PAGE results for velaglucerase alfa in tartrate and fumarate formulations, respectively, were evaluated. There was no significant degradation of velaglucerase alfa in both formulations after storage at −20° C. for 1 month and shaking for 24 hours. However, there was apparent degradation of velaglucerase alfa to smaller MW species for both formulations that were stored at 40° C. for 0.5 month and 1.0 month. However, there was no apparent difference between these two formulations for all the treatment conditions.

2.14 DSC

DSC data were collected using Micro-Cal VP DSC software at a ramping rate 1° C./min from 10° C. to 95° C. The DSC thermogram were collected after the formulations were diluted to approximately 4.67 mg/mL. The data for the respective buffer was also collected. The thermogram for each buffer were corrected against water-water thermogram. The thermogram for each active formulation was corrected against their respective buffer and evaluated.

TABLE 27

Tm (° C.) value for velaglucerase alfa in tartrate and fumarate formulations

| | Tartrate formulation | Fumarate formulation |
|---|---|---|
| Run 1 | 71.58 | 71.28 |
| Run 2 | 71.17 | 71.08 |
| Average | 71.38 | 71.18 |
| SD | 0.29 | 0.14 |

2.15 Mass Spectroscopy
2.15.1 Intact Mass

Intact mass was collected with both non-reduced samples and reduced samples.

The non-reduced sample was prepared with 1 μL of each sample mixed with 400 μl of 0.1% TFA, and then 10 μl of the resulting mixture was injected into the LC-MS system. The reduced sample was prepared in the following procedure: each sample was denatured with 6M guanidine, reduced with DTT and alkylated with IAA. After desalting, 10 μl of ~0.5 mg/ml of each sample (in 100 mM Tris, pH 8.5) was injected into 6600.

The HPLC conditions: column: ACE 5 Phenyl-300, 1.0× 50 mm, 5 μm, P/N ACE-225-0501M: Mobile Phase A: 0.1% Trifluoroacetic Acid in Water; and B: 0.085% Trifluoroacetic Acid in Acetonitrile and the gradient elution condition is shown in Table 28.

TABLE 28

Gradient elution condition for collecting intact mass spectrometry

| Time | Flow rate | A % | B % | Curve |
|---|---|---|---|---|
| Initial | 0.2 | 90 | 10 | Initial |
| 3 | 0.2 | 90 | 10 | 6 |
| 5 | 0.2 | 70 | 30 | 6 |

TABLE 28-continued

Gradient elution condition for collecting intact mass spectrometry

| Time | Flow rate | A % | B % | Curve |
|---|---|---|---|---|
| 7 | 0.2 | 60 | 40 | 6 |
| 17 | 0.2 | 50 | 50 | 6 |
| 19 | 0.2 | 5 | 95 | 6 |
| 23 | 0.2 | 5 | 95 | 6 |
| 24 | 0.2 | 90 | 10 | 6 |
| 27 | 0.2 | 90 | 10 | 6 |

Non-reduced and reduced mass chromatograms of the velaglucerase alfa formulations were evaluated. No significant difference in retention time and mass was observed between these two formulations at each of the conditions.

2.16 Peptide Map

Velaglucerase alfa sample was denatured, reduced and alkylated. Additional DTT was added to quench the excess alkylation and the reaction mixture was desalted using NAP-5 desalting column. Endoproteinase Lys-C was added to the desalted sample and reacted for 5 hours at 37° C., thereafter, N-Glycanse-PLUS was added to the digested sample and reacted for 1 hour at 37° C. The resulting deglypeptides were separated on an ACE C18 column (150×2.1 mm, 3µ, 300 Å) that was kept at 40° C.

A curved gradient over the range of 2% to 43% acetonitrile in water with trifluoroacetic acid and a flow rate of 0.25 mL/min was used to separate the peptides.

Peptide mapping results respectively for velaglucerase alfa in tartrate and fumarate formulation at T0, after shaking at 200 rpm for 24 hours, storage at 40° C. for 1 month, storage at −20° C. for 1 month were evaluated. Sequence and abundance of identified peptides were evaluated. There was no significant difference in retention time as well as mass result for each peptide between the formulations 3. Conclusion Velaglucerase alfa formulations containing velaglucerase alfa at 140 mg/mL and isofagomine tartrate or isofagomine fumarate were prepared in the same way and evaluated at storage conditions at 40° C. and −20° C. for up to 1 month and after shaking for 200 rpm for 24 hours.

At T0, there was no significant difference between two formulation for appearance, pH, protein concentration, osmolality, P188 concentration, sub-visible particles, RP-HPLC, SE-HPLC, SDS-PAGE, activity, intact mass at reduced and non-reduced condition and peptide mapping. Isofagomine content in fumarate formulation was higher than tartrate formulation, A320 value for fumarate formulation was slightly greater than that for tartrate formulation. Tm value for tartrate formulation was slightly greater than that for fumarate formulation. In addition, the viscosity result for fumarate formulation was slightly higher than tartrate formulation.

During storage for up to 1 month at 40° C., the quality attribute results of these two formulations were comparable by appearance, pH, protein concentration, sub-visible particles, RP-HPLC, SDS-PAGE, activity, A320, intact mass at reduced and non-reduced condition and peptide mapping. However, SE-HPLC results show that fumarate formulation was slightly less stable than tartrate formulation by aggregation level. In addition, isofagomine content for fumarate formulation was slightly more than tartrate formulation, consistent with the T0 results.

After storage for 1 month at −20° C. and after shaking at 200 rpm for 24 hours, the quality attribute results of these two formulations were comparable by appearance, sub-visible particles, RP-HPLC, SE-HPLC, SDS-PAGE, activity, intact mass at reduced and non-reduced condition and peptide mapping. A320 value for fumarate formulation was slightly greater than that of tartrate formulation.

In summary, isofagomine fumarate has a largely comparable stabilization effect to isofagomine tartrate during storage and mechanical stress. However, isofagomine tartrate was expected to have a slightly higher aggregation level during storage and higher a slightly higher viscosity.

Example 8: Stability Study of Velaglucerase Alfa Formulation B-IFG Tartrate Under Various Storage Conditions In order to obtain insight regarding long term storage stability of the pharmaceutical velaglucerase alfa-IFG tartrate salt Formulation B (See, Example 6 above) formulated with an isofagomine tartrate salt, long term storage stress-tests were conducted. The formulation has a high protein concentration suitable for subcutaneous administration.

The isofagomine compound used for stabilization of velaglucerase alfa in solution was isofagomine tartrate. The formulation buffer contains 3 mM isofagomine (free isofagomine) and the protein binds isofagomine in a 1:1 molar ratio. At 60 mg/mL protein concentration the molarity of the protein is approximately 1 mM (the molecular weight of glycosylated velaglucerase alfa is 63 kDa). During the UFDF process when the viral filtration pool is concentrated and buffer exchanged approximately 1 mM isofagomine will bind to the protein. The total isofagomine content of the drug substance is the sum of free and bound isofagomine and is monitored for velaglucerase alfa-IFG tartrate salt Formulation B.

At the long term storage condition (≤−65° C.) the results from purity testing up to 18 months reveal an increase of high molecular weight species by SE-HPLC and no changes by RP-HPLC and SDS-PAGE (Coomassie). Protein content, pH, and potency results show no trends for up to 18 months. These procedures are as described in Example 7.

All results at the long-term storage condition met specifications. Visible particles were observed and are attributed to the non-controlled environment in which the material was handled and are not related to protein formulation or stability. The standard for appearance of velaglucerase alfa Formulation B-IFG tartrate is "essentially free of particles". Visible particles are not expected under GMP conditions. Test for color and clarity conforms to specification at all time points and storage conditions.

Based on the real time stability data, velaglucerase alfa drug substance is stable for 18 months upon storage at ≤−65° C. See, Table 29, below. The available data and trend charts produced therefrom support that the velaglucerase alfa drug product is expected to remain within the acceptance criteria of the specification through 30 months when stored at the long-term storage condition of ≤−65° C.

Twelve and three months of data have been generated at the accelerated (−20±5° C.) and stress (5±3° C.) conditions, respectively. See Tables 30 and 31 below, respectively. At the accelerated storage condition (−20±5° C.) trends are comparable to the long-term storage condition. At the stress storage condition (5±3° C.) velaglucerase alfa drug substance is stable up to 3 months.

3.1 Appearance

The appearance results for drug product at the long-term storage temperature of ≤−65° C. met the acceptance criteria. No apparent changes were observed for all the tested samples.

3.2 pH

The pH results for the velaglucerase alfa drug product at the long-term storage temperature of ≤−65° C. met the acceptance criteria. No significant changes or trends were observed.

3.3 Protein Concentration (A280)

Determination of protein concentration was done by measuring absorbance at 280 nm (A280). The available protein concentration results at the long-term storage temperature of ≤−65° C. for the velaglucerase alfa drug product are within the acceptance criterion for all tested samples. No apparent changes or trends were observed.

3.4 SE-HPLC

The available SE-HPLC results at the long-term storage temperature of ≤−65° C. for the velaglucerase alfa drug product at 60 mg/mL are within the acceptance criterion for all tested samples. No apparent changes or trends were observed.

3.5 Specific Activity

The available specific activity results at the long-term storage temperature of ≤−65° C. for the velaglucerase alfa drug product are within the acceptance criterion for all tested samples. No apparent changes or trends were observed.

3.6 SDS-PAGE

The available SDS-PAGE results at the long-term storage temperature of ≤−65° C. for the velaglucerase alfa drug product are within the acceptance criterion

3.7 Sub-Visible Particulates

The available results at the long-term storage temperature of ≤−65° C. for the velaglucerase alfa drug product are within the acceptance criterion for all tested samples.

3.8 Cellular Uptake Bioassay (CUB)

The available CUB results at the long-term storage temperature of ≤−65° C. for the velaglucerase alfa drug product are within the acceptance criterion for all tested samples. A slight increase in relative uptake is observed.

3.9 Isofagomine (IFG) Content

The available total isofagomine concentration results at the long-term storage temperature of ≤−65° C. for the velaglucerase alfa drug product are within the acceptance criterion for all tested samples. A slight decrease in IFG content was observed. An increase in visible and/or subvisible particulates as well SEC-HPLC HMWS would be expected if isofagomine levels fell below the amount needed to maintain the stability of glucocerebrosidase. Statistically significant trends in these attributes were not observed.

3.10 Conclusion

The stability results support the extension of velaglucerase alfa shelf life from 12 months to 30 months at the long-term storage condition ≤−65° C.

TABLE 29

Stability Data for velaglucerase alfa Formulation B-IFG tartrate after 18 months at the Long-Term storage condition (≤−65° .C).

| Test | Acceptance Criteria | Months | | | | | | |
|---|---|---|---|---|---|---|---|---|
| | | 0 | 1 | 3 | 6 | 9 | 12 | 18 |
| Visible Particles | Essentially free of visible particles | Conforms | Conforms | Conforms | Conforms | Conforms | Conforms | Conforms |
| Clarity | Clear to slightly opalescent | Slightly opalescent | Slightly opalescent | Slightly opalescent | Slightly opalescent | Slightly opalescent | Slightly opalescent | Slightly opalescent |
| Color | Colorless to slightly colored | Colorless | Colorless | Colorless | Colorless | Colorless | Colorless | Colorless |
| MFI | Report Results | 30 2 | NS | NS | NS | NS | 23 1 | NS |
| SE-HPLC main HMWS | ≥90.0% main peak area; ≤5.0% HMWS[3] | 99.6 0.4 | 99.6 0.4 | 99.6 0.4 | 99.6 0.4 | 99.5 0.5 | 99.3 0.7 | 99.6 0.4 |
| RP-HPLC main | Report result [%] | 96.3 | 97.0 | 97.6 | 96.6 | 97.2 | 97.5 | 95.6 |
| SDS-PAGE (Coomassie: reduced) | Report result | No impurity band >3% | No impurity band >3% | No impurity band >3% | No impurity band >3% | No impurity band >3% | No impurity band >3% | No impurity band >3% |
| Specific Activity | 19-45 U/mg | 35 | 40 | 35 | 39 | NT | 33 | 35 |
| Protein Concentration | 60.0 ± 9.0 mg/mL | 64.5 | 63.8 | 64.1 | 65.0 | 64.2 | 65.2 | 65.0 |
| Cellular Uptake (Bioassay) | Report result [%] | NS | NS | NS | NS | NS | 100 | NS |
| pH | 6.0 ± 0.3 | 6.0 | 6.1 | 6.0 | 6.0 | 6.0 | 6.0 | 6.1 |
| Isofagomine Content[3] | Report result [mM] | NS | NS | NS | NS | NS | 3.7 | NS |

NS = not scheduled per protocol; NT - Not tested
[a] IFG content test was not yet developed at study initiation.

TABLE 30

Stability Data for velaglucerase alfa Formulation B-IFG tartrate after 12 months at −20 ± 5° C.

| Test | Acceptance Criteria/Units | Formulation Fill Volume: 1.5 mL Container Size/Type/Supplier: 5 mL PC bottle Stopper/Supplier: PP screw cap Time Point (Months) | | | | |
|---|---|---|---|---|---|---|
| | | 0 | 1 | 3 | 6 | 12 |
| Appearance: Color | Colorless to slightly colored | Conforms | Conforms | Conforms | Conforms | Conforms |
| Appearance: Clarity | Clear to slightly opalescent | Conforms | Conforms | Conforms | Conforms | Conforms |
| Appearance: Visible particles | Essentially free of visible particles | Conforms | Conforms | Conforms | Conforms | Conforms |
| SDS-PAGE (Coomassie) | Report result | No impurity band >3% | No impurity band >3% | No impurity band >3% | No impurity band >3% | No impurity band >3% |
| Size exclusion HPLC | ≥90.0% Main peak ≤5.0% HMWS | 99.6 0.4 | 99.6 0.4 | 99.6 0.4 | 99.6 0.4 | 99.2 0.7 |
| Reversed Phase HPLC | Main Peak: Report result [%] Peak A through B [%] Peak C [%] | 97.2 1.1 1.5 | 97.0 1.1 1.5 | 97.7 0.8 1.4 | 95.6 1.3 1.5 | 97.4 1.4 0.4 |
| Specific activity | 19-45 U/mg | 34 | 39 | 35 | 38 | 32 |
| Protein concentration | 60.0 ± 7.5 mg/mL | 65.0 | 66.5 | 64.7 | 65.7 | 66.5 |
| pH | 6.0 ± 0.3 | 6.0 | 6.1 | 6.0 | 6.0 | 6.0 | a- Some white particles were observed.

TABLE 31

Stability Data for velaglucerase alfa Formulation B - IFG tartrate after 3 months at −5 ± 3° C.

Formulation Container Size/Type/Supplier: 5 mL PC bottle   Fill Volume: 1.5 mL   Stopper/Supplier: PP screw cap

| Test | Acceptance Criteria/Units | Time Point (Months) | | |
|---|---|---|---|---|
| | | 0 | 1 | 3 |
| Appearance: Color | Colorless to slightly colored | Conforms | Conforms | Conforms |
| Appearance: Clarity | Clear to slightly opalescent | Conforms | Conforms | Conforms |
| Appearance: Visible particles | Essentially free of visible particles | Conforms | Conforms$^a$ | Conforms |
| SDS-PAGE (Coomassie) | Report result | No impurity band > 3% | No impurity band > 3% | No impurity band > 3% |
| Size exclusion HPLC | ≥90.0% Main peak ≤ 5.0% HMWS | 99.6 0.4 | 98.5 0.6 | 99.2 0.8 |
| Reversed Phase HPLC | Main Peak: Report result [%] Peak A through B [%] Peak C [%] | 97.2 1.1 1.5 | 97.0 1.1 1.5 | 97.5 0.9 1.5 |
| Specific activity | 19-45 U/mg | 34 | 39 | 34 |
| Protein concentration | 60.0 ± 7.5 mg/mL | 65.0 | 66.6 | 68.8 |
| Ph | 6.0 ± 0.3 | 6.0 | 6.1 | 6.0 |

$^a$Some white particles were observed.

The present invention was not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It was further to be understood that all values are approximate and are provided for description.

All publications, patent applications, patents, and other references mentioned herein are incorporated by reference in their entirety. In the case of conflict, the present specification, including definitions, controls. In addition, the materials, methods, and examples are illustrative only and not intended to be limiting.

The invention claimed is:

1. A salt of isofagomine wherein the salt is selected from a quinate, maleate, fumarate, oxalate, malonate, succinate, cyclamate and ascorbate salt.

2. The salt according to claim 1, wherein the salt is isofagomine quinate, isofagomine fumarate, isofagomine oxalate, isofagomine succinate, or isofagomine cyclamate.

3. The salt according to claim 2, wherein isofagomine quinate is in a crystalline form characterized by an x-ray diffraction pattern having three or more characteristic peaks at 2theta values selected from: 9.5°±0.2°, 15.0°±0.2°, 17.4°±0.2°, 18.1°±0.2°, 20.3°±0.2°, 23.8°±0.2°, 24.8°±0.2° and 25.4°±0.2°; wherein isofagomine fumarate is in a crystalline form characterized by an x-ray diffraction pattern having three or more characteristic peaks at 2theta values selected from: 16.1°, ±0.2°, 18.3°, ±0.2°, 18.6°, ±0.2°, 21.9°, ±0.2°, 23.6°, ±0.2°, 23.8°±0.2° and 25.5°±0.2°; wherein isofagomine oxalate is in a crystalline form characterized by an x-ray diffraction pattern having three or more characteristic peaks at 2theta values selected from: 27.8°±0.2°, 32.2°±0.2°, 35.3°±0.2°, 36.6°±0.2°, 37.4°±0.2°, 38.4°±0.2°, 18.5°±0.2°, 19.2°±0.2°, 21.4°±0.2°, 22.6°±0.2°, 24.5°±0.2°, 24.8°±0.2°, 26.8°±0.2°, 20.2°±0.2° and 23.7°±0.2°; wherein isofagomine succinate is in a crystalline form characterized by having XRPD peaks; or wherein isofagomine cyclamate is in a crystalline form characterized by having XRPD peaks.

4. A salt of isofagomine wherein the salt is a crystalline form of isofagomine D-tartrate characterized by an x-ray diffraction pattern having three or more characteristic peaks at 2theta values selected from: 9.8°, ±0.2°, 10.5°±0.2°, 15°±0.2°, 15.3°±0.2°, 15.8°±0.2°, 17.4°±0.2°, 17.9°±0.2°, 18.5°±0.2°, 18.9°±0.2°, 19.6°±0.2°, 21.1°±0.2°, 21.7°±0.2°, 220° 0.2°, 24.2°±0.2°, 24.8°±0.2°, 26.6°±0.2°, 27.1°±0.2°, 27.4°±0.2°, 33.8°±0.2°, 35.7°±0.2°, 36.5°±0.2° and 37.5°±0.2°.

5. A pharmaceutical composition comprising at least one isofagomine salt according to claim 1 and a pharmaceutically acceptable carrier.

6. The pharmaceutical composition of claim 5 further comprising a glucocerebrosidase wherein isofagomine is present in an amount sufficient to stabilize the glucocerebrosidase.

7. The pharmaceutical composition of claim 5, wherein the glucocerebrosidase is velaglucerase alfa.

8. The pharmaceutical composition of claim 5, wherein the glucocerebrosidase and the isofagomine are in a molar ratio of about 1:2.5 to about 1:3.5.

9. The pharmaceutical composition of claim 8, wherein the composition comprises 60-180 mg/mL of glucocerebrosidase and wherein isofagomine is present in at least about a 3-fold molar excess to the glucocerebrosidase.

10. The pharmaceutical composition of claim 6, comprising glucocerebrosidase and isofagomine in a molar ratio of about 1:3, wherein the composition further comprises a sodium citrate buffer, sucrose and one or more surfactant selected from PS20, PS80 and poloxamer 188.

11. A method of preparing a pharmaceutical composition according to claim 5 comprising combining isofagomine and a pharmaceutically acceptable carrier.

12. A method of treating Gaucher disease, comprising administering to a patient in need of such a treatment a therapeutically effective amount of an isofagomine salt or formulation thereof according to claim 1.

13. A method of producing an isofagomine salt comprising the steps of:
  i) dissolving an organic acid in a polar protic solvent to produce a solution 1;
  ii) dissolving isofagomine free base in a polar protic solvent to produce a solution 2;
  iii) combining solution 1 and solution 2, thereby forming a precipitate; and
  iv) isolating the precipitate corresponding to the isofagomine salt;
  wherein the organic acid is selected from quinic acid, fumaric acid, oxalic acid, malonic acid, D-tartaric acid, L-tartaric acid, succinic acid, cyclamic acid and ascorbic acid.

14. A composition comprising an isofagomine salt according to claim 1 wherein the isofagomine salt is at least about 95% pure.

15. A method of treating Gaucher disease, comprising administering to a patient in need of such a treatment a therapeutically effective amount of a pharmaceutical composition according to claim 5.

16. A method of treating Gaucher disease, comprising administering to a patient in need of such a treatment a therapeutically effective amount of an isofagomine salt or formulation thereof according claim 4.

17. A method of treating Gaucher disease, comprising administering to a patient in need of such a treatment a therapeutically effective amount of a pharmaceutical composition according to claim 10.

18. A pharmaceutical composition comprising at least one isofagomine salt according to claim 4 and a pharmaceutically acceptable carrier.

* * * * *